United States Patent
Boyne et al.

(10) Patent No.: US 12,416,018 B2
(45) Date of Patent: *Sep. 16, 2025

(54) REGULATION OF GENE EXPRESSION BY APTAMER-MEDIATED MODULATION OF ALTERNATIVE SPLICING

(71) Applicant: MEIRAGTX GENE REGULATION LIMITED, London (GB)

(72) Inventors: Alex R. Boyne, Jersey City, NJ (US); Olivier F. Danos, New York, NY (US); Michael J. Volles, Cambridge, MA (US); Xuecui Guo, Oyster Bay, NY (US)

(73) Assignee: MEIRAGTX GENE REGULATION LIMITED, London (GB)

( * ) Notice: Subject to any disclaimer, the term of this patent is extended or adjusted under 35 U.S.C. 154(b) by 598 days.

This patent is subject to a terminal disclaimer.

(21) Appl. No.: 17/671,048

(22) Filed: Feb. 14, 2022

(65) Prior Publication Data
US 2022/0282278 A1   Sep. 8, 2022

Related U.S. Application Data

(60) Continuation of application No. 16/692,928, filed on Nov. 22, 2019, now Pat. No. 11,248,239, which is a division of application No. 15/548,043, filed as application No. PCT/US2016/016234 on Feb. 2, 2016, now Pat. No. 10,494,646.

(60) Provisional application No. 62/110,919, filed on Feb. 2, 2015.

(51) Int. Cl.
| | |
|---|---|
| *C12N 15/113* | (2010.01) |
| *A61K 9/00* | (2006.01) |
| *A61K 38/44* | (2006.01) |
| *A61K 48/00* | (2006.01) |
| *C12N 9/06* | (2006.01) |
| *C12N 15/115* | (2010.01) |
| *C12N 15/63* | (2006.01) |
| *C12N 15/86* | (2006.01) |

(52) U.S. Cl.
CPC ............ *C12N 15/86* (2013.01); *A61K 9/0048* (2013.01); *A61K 38/44* (2013.01); *A61K 48/0033* (2013.01); *A61K 48/0066* (2013.01); *A61K 48/0075* (2013.01); *C12N 9/003* (2013.01); *C12N 15/115* (2013.01); *C12N 15/63* (2013.01); *C12Y 105/01003* (2013.01); C12N 2310/16 (2013.01); C12N 2310/3519 (2013.01); C12N 2320/32 (2013.01); C12N 2320/33 (2013.01); C12N 2750/14143 (2013.01); C12N 2750/14171 (2013.01); C12N 2840/002 (2013.01); C12N 2840/44 (2013.01)

(58) Field of Classification Search
CPC .............. A61K 48/0066; C12N 15/115; C12N 2310/16; C12N 2310/3519; C12N 2320/33; C12N 15/11
See application file for complete search history.

(56) References Cited

U.S. PATENT DOCUMENTS

| | | | |
|---|---|---|---|
| 10,494,646 B2* | 12/2019 | Boyne ................. | C12N 15/115 |
| 11,248,239 B2* | 2/2022 | Boyne ................ | A61K 48/0033 |
| 2004/0126882 A1 | 7/2004 | Ellington et al. | |
| 2005/0197311 A1 | 9/2005 | Cooper et al. | |
| 2006/0088864 A1 | 4/2006 | Smolke et al. | |
| 2008/0124760 A1 | 5/2008 | Enenkel et al. | |
| 2009/0143327 A1 | 6/2009 | Smolke et al. | |
| 2009/0170793 A1 | 7/2009 | Gaur | |
| 2010/0184810 A1 | 7/2010 | Breaker et al. | |
| 2010/0221821 A1 | 9/2010 | Breaker et al. | |
| 2010/0223694 A1 | 9/2010 | Lutfiyya et al. | |
| 2011/0111411 A1 | 5/2011 | Smolke et al. | |
| 2013/0291226 A1 | 10/2013 | Hammond et al. | |
| 2015/0175981 A1 | 6/2015 | Olsen | |

FOREIGN PATENT DOCUMENTS

| | | |
|---|---|---|
| CN | 101517085 A | 8/2009 |
| CN | 101801185 A | 8/2010 |
| JP | 2003527856 A | 9/2003 |
| WO | 01/70949 A1 | 9/2001 |

(Continued)

OTHER PUBLICATIONS

Han, X. et al., "Riboswitch in Gene Expression Regulation", Chinese Journal of Biochemistry and Molecular Biology (2011), vol. 27:12, pp. 1094-1100.
Knowles, J. K. et al., "A Small Molecule p75NTR Ligand Prevents Cognitive Deficits and Neurite Degeneration in an Alzheimer's Mouse Model", Neurobiology of Aging (2013), vol. 34, pp. 2052-2063.
Berens, C. et al., "RNA Aptamers as Genetic Control Devices: The Potential of Riboswitches as Synthetic Elements for Regulating Gene Expression"; Biotechnol. J. (2015); vol. 10, pp. 246-257.
Breaker, R.R., "Riboswitches and the RNA World", Cold Spring Harb Perspect Biol (2015), vol. 2012: 4:a003566.

(Continued)

*Primary Examiner* — J. E. Angell
(74) *Attorney, Agent, or Firm* — Fox Rothschild LLP

(57) ABSTRACT

The invention provides a platform and methods of using the platform for the regulation of the expression of a target gene using exposure to an aptamer ligand (for example, a small molecule). The platform features a polynucleotide gene regulation cassette that is placed in the target gene and includes a synthetic riboswitch positioned in the context of a 5' intron-alternative exon-3' intron. The riboswitch comprises an effector region and a sensor region (e.g., an aptamer that binds a small molecule ligand) such that the alternative exon is spliced into the target gene mRNA when the ligand is not present thereby preventing expression of the target gene. When the ligand is present, the alternative exon is not spliced into the target gene mRNA thereby providing expression of the target gene.

43 Claims, 29 Drawing Sheets
Specification includes a Sequence Listing.

(56) References Cited

FOREIGN PATENT DOCUMENTS

| WO | 2013176772 A1 | 11/2013 |
| WO | 2016/166303 A1 | 10/2016 |

OTHER PUBLICATIONS

Culler, S. J. et al., "Functional Selection and Systematic Analysis of Intronic Splicing Elements Identify Active Sequence Motifs and Associated Splicing Factors"; Nucleic Acids Res. (2010); vol. 38:15; pp. 5152-5165.

Culler, S. J. et al., "Reprogramming Cellular Behavior with RNA Controllers Responsive to Endogenous Proteins"; Science (2010); vol. 330; pp. 1251-1255.

Garst, A.D. et al., "Riboswitches: Structures and Mechanisms"; Cold Spring Harb Perspect Biol. (2011); vol. 3:a003533 (13 pgs).

Gusti, V., "Sequestering of the 3? Splice Site in a Theophylline-Responsive Riboswitch Allows Ligand-Dependent Control of Alternative Splicing"; Oligonucleotides (2008); vol. 18, pp. 93-99.

Hang, J. et al., "Structural basis of pre-mRNA splicing"; Science (2015), vol. 349:6253, pp. 1191-1198.

Hickey, S. F. et al., "Transgene Regulation in Plants By Alternative Splicing O\of A Suicide Exon", Nucleic Acids Res. (2012); vol. 40, pp. 4701-4710.

Kim, D. S. et al., "An Artificial Riboswitch for Controlling Pre-mRNA Splicing", RNA (2015); vol. 11, pp. 1667-1677.

Kim, D. S. et al., Ligand-Induced Sequestering of Branchpoint Sequence Allows Conditional Control of Splicing ; BMC Mol. Biol. (2008); vol. 9:23 (15 pgs.).

Liang, J. C. et al., "Engineering Biological Systems with Synthetic RNA Molecules"; Molecular Cell (2011); vol. 43; pp. 915-926.

Serganov, A. et al., "A Decade of Riboswitches" Cell (2013); vol. 152, pp. 17-24.

Wang Z. et al., "Systemic Identification and Analysis of Exonic Splicing Silencers"; Cell (2004); vol. 119; pp. 831-845.

Weigand, J. E. et al., "Tetracycline Aptamer-Controlled Regulation of Pre-Mrna Splicing in Yeast"; Nucleic Acids Res. (2007); vol. 35:12, pp. 4179-4185.

* cited by examiner

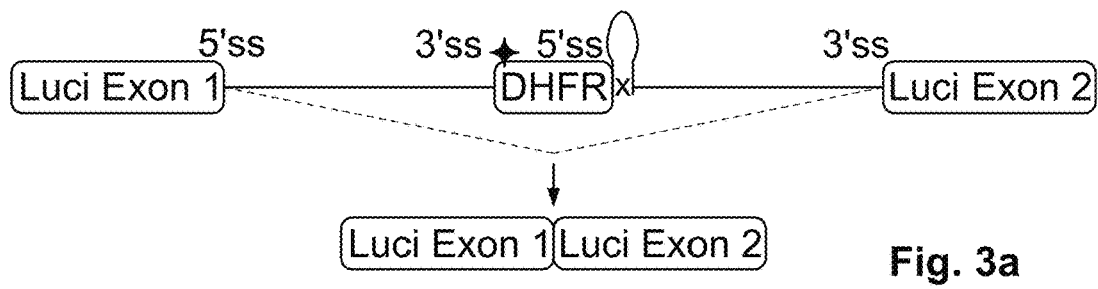
Fig. 3a
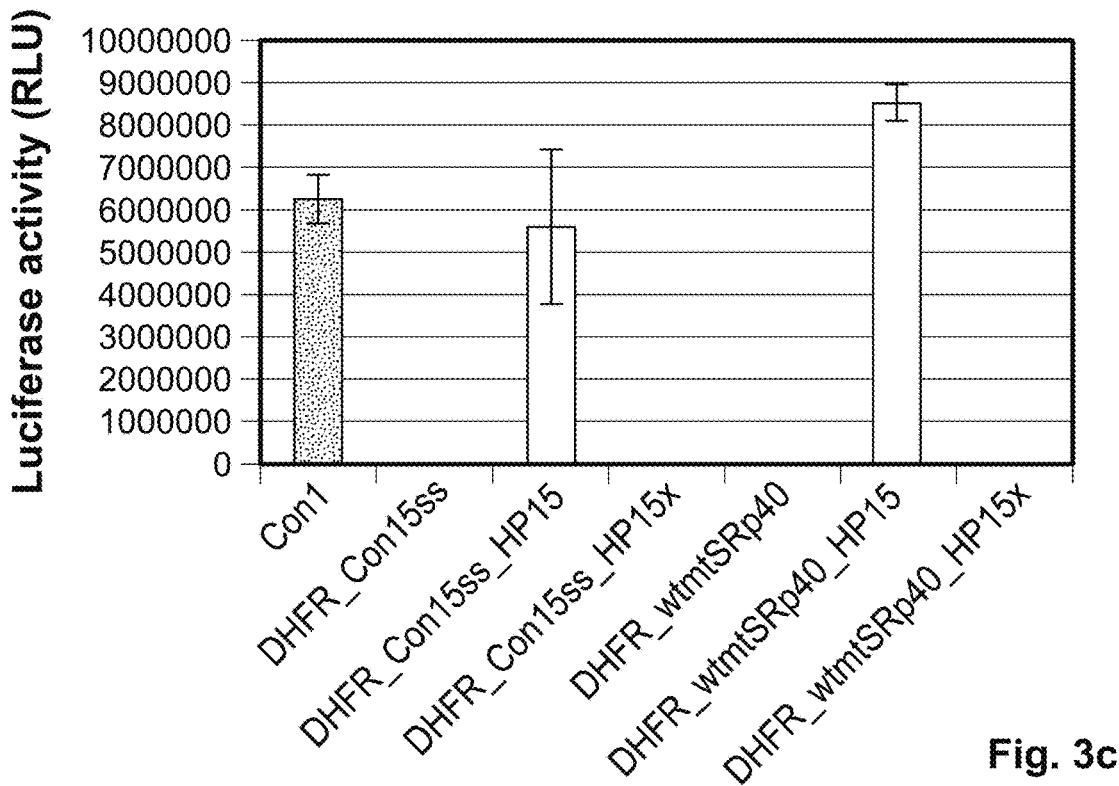
Fig. 3b
Fig. 3c

REGULATION OF GENE EXPRESSION BY APTAMER-MEDIATED MODULATION OF ALTERNATIVE SPLICING

CROSS REFERENCE TO RELATED APPLICATIONS

This application is a Continuation of U.S. application Ser. No. 16/692,928, filed Nov. 22, 2019, issuing Feb. 15, 2022 as U.S. Pat. No. 11,248,239, which is a Divisional of U.S. application Ser. No. 15/548,043, filed Aug. 1, 2017, now U.S. Pat. No. 10,494,646, issued Dec. 3, 2019, which is a 371 PCT/US2016/016234, filed Feb. 2, 2016, which claims the benefit of priority to U.S. Application No. 62/110,919 filed Feb. 2, 2015, all which are incorporated herein by reference in their entireties.

REFERENCE TO A SEQUENCE LISTING

This application contains a Sequence Listing, which has been submitted electronically in ASCII format and is hereby incorporated by reference in its entirety. Said file, created on Sep. 18, 2024, is named SeqList2-162027-46103.txt and is 51,926 bytes in size.

FIELD OF THE INVENTION

The invention provides a platform and methods of using the platform for the regulation of the expression of a target gene using exposure to a small molecule. The platform features a polynucleotide cassette that is placed in the target gene and includes a synthetic riboswitch positioned in the context of a 5' intron-alternative exon-3' intron. The riboswitch comprises an effector region and an aptamer that binds a ligand (e.g., a small molecule) and provides control of target gene expression by exposure to the ligand.

BACKGROUND OF THE INVENTION

Splicing refers to the process by which intronic sequence is removed from the nascent pre-messenger RNA (pre-mRNA) and the exons are joined together to form the mRNA. Splice sites are junctions between exons and introns, and are defined by different consensus sequences at the 5' and 3' ends of the intron (i.e., the splice donor and splice acceptor sites, respectively). Alternative pre-mRNA splicing, or alternative splicing, is a widespread process occurring in most human genes containing multiple exons. It is carried out by a large multi-component structure called the spliceosome, which is a collection of small nuclear ribonucleoproteins (snRNPs) and a diverse array of auxiliary proteins. By recognizing various cis regulatory sequences, the spliceosome defines exon/intron boundaries, removes intronic sequences, and splices together the exons into a final translatable message (i.e., the mRNA). In the case of alternative splicing, certain exons can be included or excluded to vary the final coding message thereby changing the resulting expressed protein.

Regulation of the expression of a target gene (e.g., a therapeutic transgene) is necessary in a variety of situations. In the context of the therapeutic expression of genes, techniques that enable regulated expression of transgenes have the potential to enhance safety by regulating the level of expression and its timing. A regulated system to control protein expression has practical and, in some cases, essential roles for safe and effective therapeutic applications.

SUMMARY OF THE INVENTION

In one aspect, the invention provides a polynucleotide cassette for the regulation of the expression of a target gene comprising (a) a riboswitch and (b) an alternatively-spliced exon, flanked by a 5' intron and a 3' intron, wherein the riboswitch comprises (i) an effector region comprising a stem that includes the 5' splice site of the 3' intron, and (ii) an aptamer, wherein the alternatively-spliced exon comprises a stop codon that is in-frame with the target gene when the alternatively-spliced exon is spliced into the target gene mRNA. In one embodiment, the aptamer specifically binds a small molecule ligand.

In one embodiment, the polynucleotide for the regulation of the expression of a target gene ("gene regulation cassette" "regulatory cassette" or "polynucleotide cassette") contains 5' and 3' introns that are derived from an endogenous intron from the target gene. In one embodiment, the 5' and 3' introns are exogenous to the target gene. In one embodiment, the 5' and 3' introns are derived from intron 2 of the human β-globin gene. In one embodiment, the 5' intron comprises a stop codon in-frame with the target gene. In one embodiment, the 5' and 3' introns are each independently from about 50 to about 300 nucleotides in length. In one embodiment, the 5' and 3' introns are each independently from about 125 to about 240 nucleotides in length. In one embodiment, the 5' and/or 3' introns have been modified to include, or alter the sequence of, an intron splice enhancer, an intron splice enhancer, a 5' splice site, a 3' splice site, or the branch point sequence.

In one embodiment, the effector region stem of the riboswitch is about 7 to about 20 base pairs in length. In one embodiment, the effector region stem is 8 to 11 base pairs in length.

In one embodiment, the alternatively-spliced exon is derived from exon 2 of the human dihydrofolate reductase gene (DHFR), mutant human Wilms tumor 1 exon 5, mouse calcium/calmodulin-dependent protein kinase II delta exon 16, or SIRT1 exon 6. In one embodiment, the alternatively-spliced exon is the modified DHFR exon 2 from SEQ ID NO: 15. In one embodiment, the alternatively-spliced exon has been modified in one or more of the group consisting of altering the sequence of an exon splice silencer, altering the sequence of an exon splice enhancer, adding an exon splice enhancer, and adding an exon splice donor. In one embodiment, the alternatively-spliced exon is synthetic (i.e., not derived from a naturally-occurring exon).

In another aspect the invention provides a method of modulating the expression of a target gene comprising (a) inserting the polynucleotide cassette of the present invention (as, e.g., described above and herein) into the target gene, (b) introducing the target gene comprising the polynucleotide cassette into a cell, and (c) exposing the cell to a small molecule ligand that specifically binds the aptamer in an amount effective to induce expression of the target gene.

In one embodiment, expression of the target gene is greater than about 5-fold higher when the small molecule ligand is present than the expression levels when the small molecule ligand is absent. In one embodiment, the expression of the target gene is greater than about 10-fold higher when the small molecule ligand is present than the expression levels when the small molecule ligand is absent.

In one embodiment, the polynucleotide cassette is inserted into the protein coding region of the target gene. In one embodiment, two or more of the polynucleotide cassettes are inserted into the target gene. In one embodiment, the two or more polynucleotide cassettes comprise different aptamers that specifically bind to different small molecule ligands. In another embodiment, the two or more polynucleotide cassettes comprise the same aptamer of different aptamers that specifically bind the same ligand.

In one embodiment, the target gene comprising the polynucleotide cassette is incorporated in a vector for the expression of the target gene. In one embodiment, the vector is a viral vector. In further embodiments, the viral vector is selected from the group consisting of adenoviral vector, adeno-associated virus vector, and lentiviral vector.

In another aspect the invention provides a method of modulating expression of a target gene in the eye of a mammal comprising (a) introducing into the eye a vector comprising a target gene that contains a polynucleotide cassette comprising (i) a riboswitch and (ii) an alternatively-spliced exon flanked by a 5' intron and a 3' intron, wherein the synthetic riboswitch comprises an effector region comprising a stem that includes the 5' splice site of the 3' intron, and an aptamer that specifically binds a ligand, wherein the alternatively-spliced exon comprises a stop codon that is in-frame with the target gene when the alternatively-spliced exon is spliced into the target gene mRNA; and (b) providing to the mammal the ligand in an amount effective to induce expression of the target gene. In one embodiment, the ligand is a small molecule.

In one embodiment, the vector is introduced into the eye by intraocular injection. In one embodiment, the vector is a viral vector. In one embodiment, the viral vector is selected from the group consisting of adenoviral vector, adeno-associated virus vector, and lentiviral vector.

In one embodiment, the polynucleotide for the regulation of the expression of a target gene in the eye contains 5' and 3' introns that are derived from an endogenous intron from the target gene. In one embodiment, the 5' and 3' introns are exogenous to the target gene. In one embodiment, the 5' and 3' introns are derived from intron 2 of the human β-globin gene. In one embodiment, the 5' intron comprises a stop codon in-frame with the target gene. In one embodiment, the 5' and 3' introns are each independently from about 50 to about 300 nucleotides in length. In one embodiment, the 5' and 3' introns are each independently from about 125 to about 240 nucleotides in length. In one embodiment, the 5' and/or 3' introns have been modified to include, or alter the sequence of, an intron splice enhancer, an intron splice enhancer, a 5' splice site, a 3' splice site, or the branch point sequence. In one embodiment, the effector region stem of the riboswitch is about 7 to about 20 base pairs in length. In one embodiment, the effector region stem is 8 to 11 base pairs in length. In one embodiment, the alternatively-spliced exon is derived from exon 2 of the human dihydrofolate reductase gene (DHFR) mutant human Wilms tumor 1 exon 5, mouse calcium/calmodulin-dependent protein kinase II delta exon 16, or SIRT1 exon 6. In one embodiment, the alternatively-spliced exon is the modified DHFR exon 2 from SEQ ID NO: 15, a modified exon 2 from human DHFR. In one embodiment, the alternatively-spliced exon has been modified in one or more of the group consisting of altering the sequence of an exon splice silencer, altering the sequence of an exon splice enhancer, adding an exon splice enhancer, and adding an exon splice donor. In one embodiment, the alternatively-spliced exon is synthetic (i.e., not derived from a naturally-occurring exon).

In one aspect, the invention provides a recombinant polynucleotide comprising a target gene containing the polynucleotide cassette for regulating expression of the target gene (as, e.g., described above). In one embodiment, the polynucleotide cassette is located in the protein coding sequence of the target gene.

In one aspect, the invention provides a vector comprising a target gene that contains a polynucleotide cassette for regulating expression of the target gene (as, e.g., described above). In one embodiment, the vector is a viral vector. In one embodiment, the viral vector is selected from the group consisting of adenoviral vector, adeno-associated virus vector, and lentiviral vector.

DESCRIPTION OF THE FIGURES

FIG. 3a. Schematic diagram of the Intron-Exon-Intron cassette containing a hairpin structure at the 5'ss of the alternative DHFR exon 2. When the DHFR 5'ss is embedded within the hairpin structure the DHFR exon will not be included in the transcript, thus allowing luciferase to be expressed (x represents the DHFR exon 5'ss buried in the hairpin).

FIG. 3b. Sequences and structures of four different hairpins tested in the Intron-Exon-Intron cassette illustrated in FIG. 3a. Con1 5ss_15HP (SEQ ID NO:66); Con1 5ss_15HPx (SEQ ID NO:67); Wt mtSRp40_15HP (SEQ ID NO:68); Wt mtSRp40_15HPx (SEQ ID NO:69).

FIG. 3c. Effect of hairpin structure at the 5'ss of DHFR exon 2 on target gene expression. The construct containing the DHFR exon with the Con 1 5'ss sequence efficiently suppresses luciferase expression due to DHFR exon inclusion in the spliced mRNA (DHFR_Con15ss, FIG. 3c). However, embedding the 5'ss of the DHFR exon in a hairpin structure, efficiently prevents the inclusion of the DHFR exon and allows luciferase expression (DHFR_Con15ss_HP15 FIG. 3c). A hairpin sequence with a disrupted stem does not restore luciferase expression (FIG. 3c. DHFR_Con15ss_HP15x). The DHFR_wtmtSRp40 construct (Example 2) does not express luciferase unless the 5'ss of the DHFR exon is stably sequestered in a hairpin structure (DHFR_wtmtSRp40_HP15). Destabilization of the hairpin prevents expression of luciferase, even in the context of a mutant SRp40 binding site with strong splicing activity (DHFR_wtmtSRp40_HP15x).

FIG. 4a.

FIG. 5d shows the basal and induced level of luciferase relative to Con1. In the absence of guanine, constructs G14 through G17 demonstrate clear regulation of luciferase expression by the aptamer ligand (in this case guanine). In the absence of guanine, luciferase expression levels are low. In the presence of guanine, luciferase expression is significantly activated. FIG. 5d shows the % of Con 1 control expression achieved for these regulated constructs on induction with guanine.

FIG. 6b. Guanine aptamer containing regulatory cassettes response to guanine.

FIG. 6c. Guanine aptamer containing regulatory cassettes response to guanosine.

FIG. 6d. Guanine aptamer containing regulatory cassettes response to 2'dG.

FIG. 6e. Adenine aptamer containing regulatory cassettes response to adenine.

FIG. 9a shows the fold induction, and 9b shows the percent of luciferase expression compared to Con 1.

FIG. 9d shows fold induction, whereas FIG. 9e shows absolute level of protein expression relative to Con 1 control.

FIG. 10a shows that constructs with different exons have various un-induced baseline and induced (500 µM guanine) levels of luciferase expression. FIG. 10b shows the induction fold with these constructs, with CaMKIId-e16 generating equivalent fold induction to the DHFR exon with SRp40 activating mutation (mtDHFR).

Figure 11A:
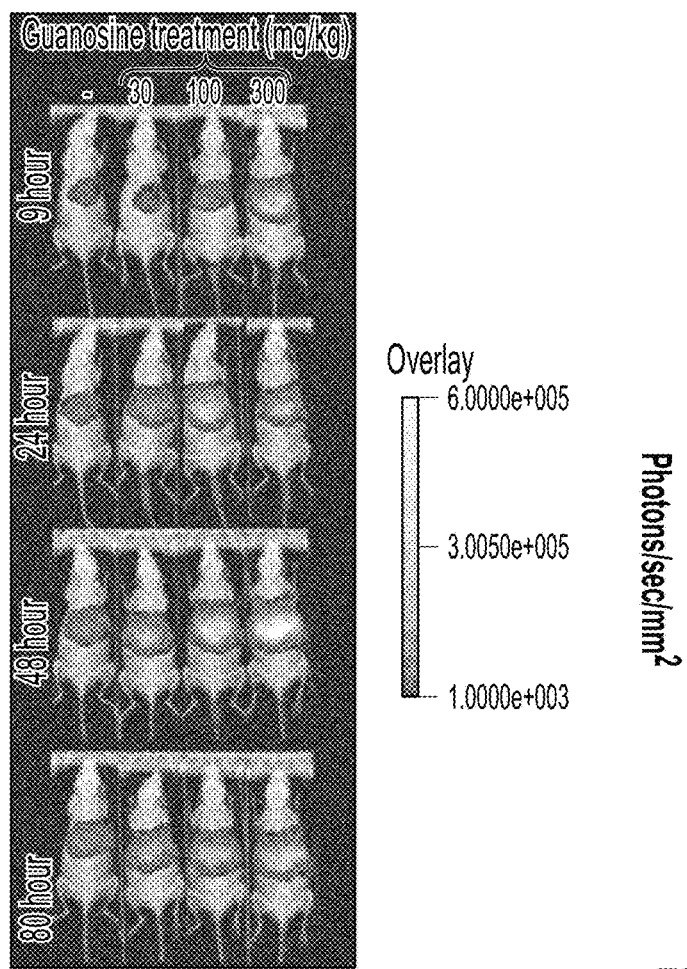
Figure 11B:
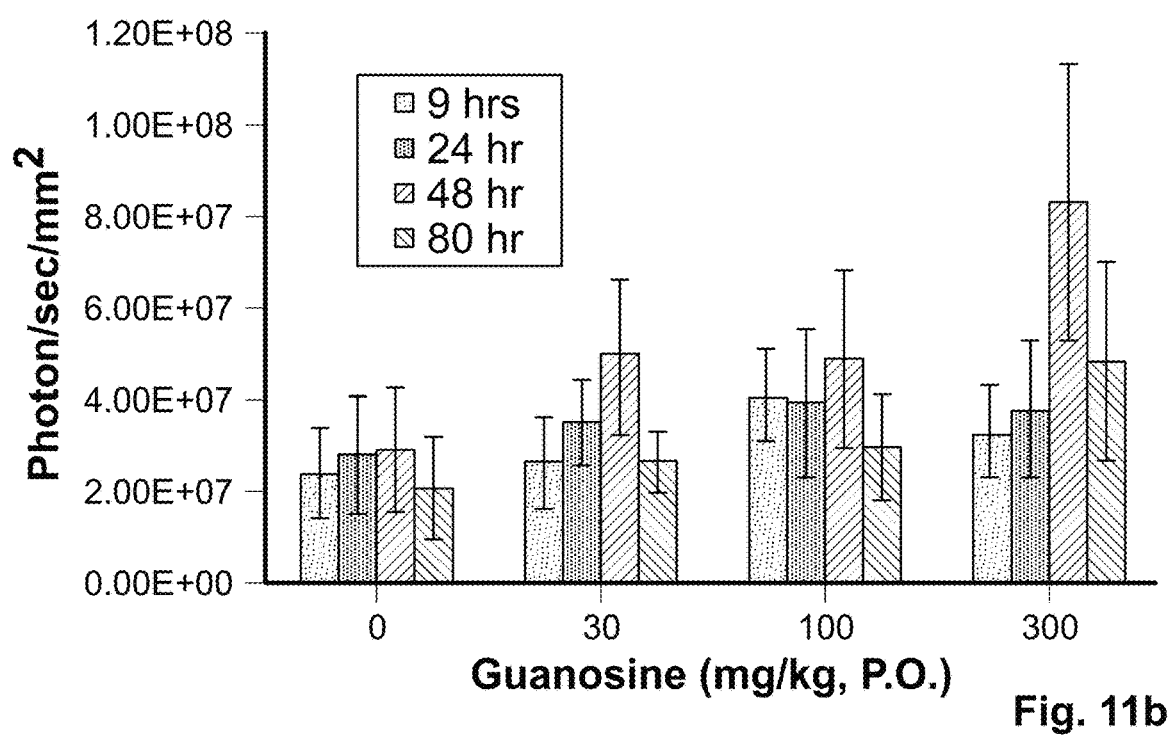

FIGS. 11a-c. Regulation of luciferase expression in vivo in mice. The construct containing two copies of the xpt-G15 regulatory cassette (xpt-G15 double, Example 8, FIG. 8a) was delivered to the liver of mice by hydrodynamic injection. Mice were dosed orally with different doses of guanosine at 2 hr and 12 hr after DNA delivery, and then were imaged. Oral dosing of the ligand resulted in dose related activation of expression of the regulated target gene in the liver of the mice (FIG. 11a and FIG. 11b).

Figure 11C:
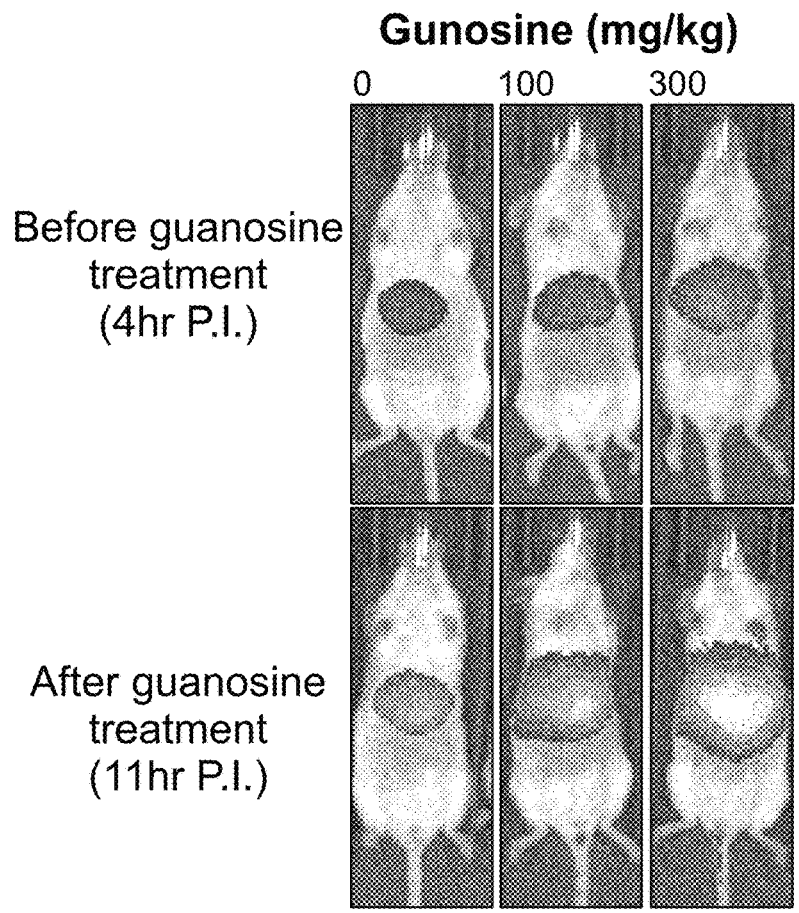
Figure 11D:
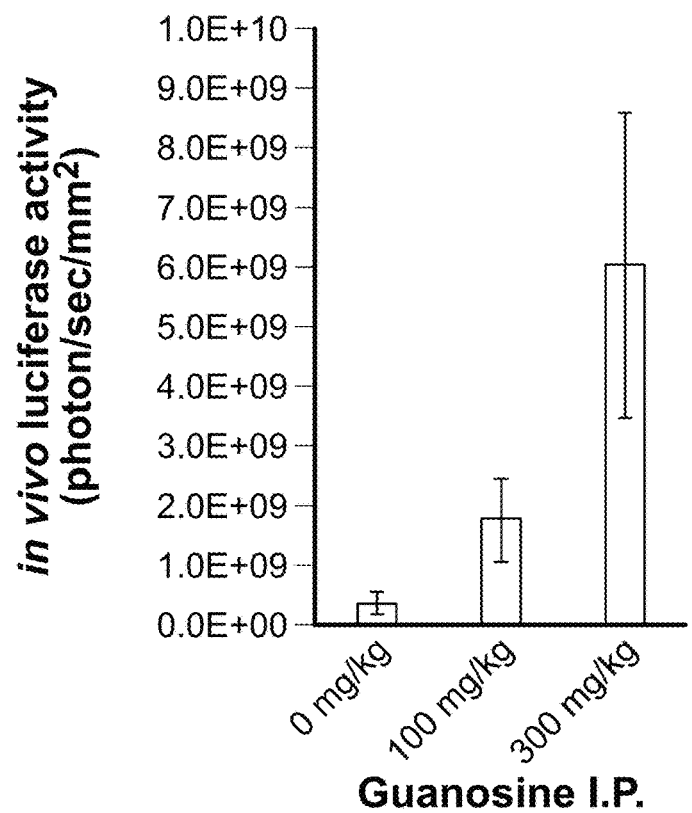

In another experiment, guanosine was administered intraperitoneally (FIG. 11c). Images show luciferase expression before and after guanosine treatment with either 100 mg/kg or 300 mg/kg dose. In the graph (FIG. 11d), the luciferase activity was expressed as mean photon/see/mm$^2$±s.d. (n=5).

Figure 12:
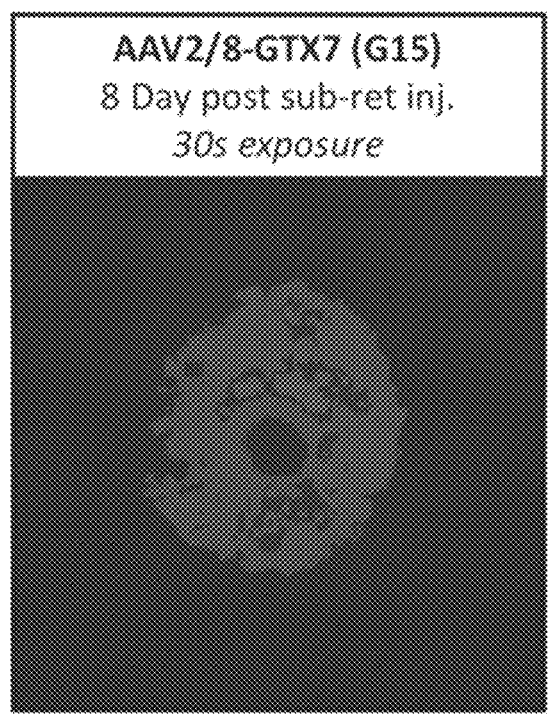

FIG. 12. EGFP transgene expression mediated by riboswitch-based AAV vectors in the murine retina. Fluorescent fundus photography showing EGFP transgene expression in the retina mediated by AAV2/8-GTX7, 8 days post subretinal injection (exposure time: 30 s).

Figure 13A:
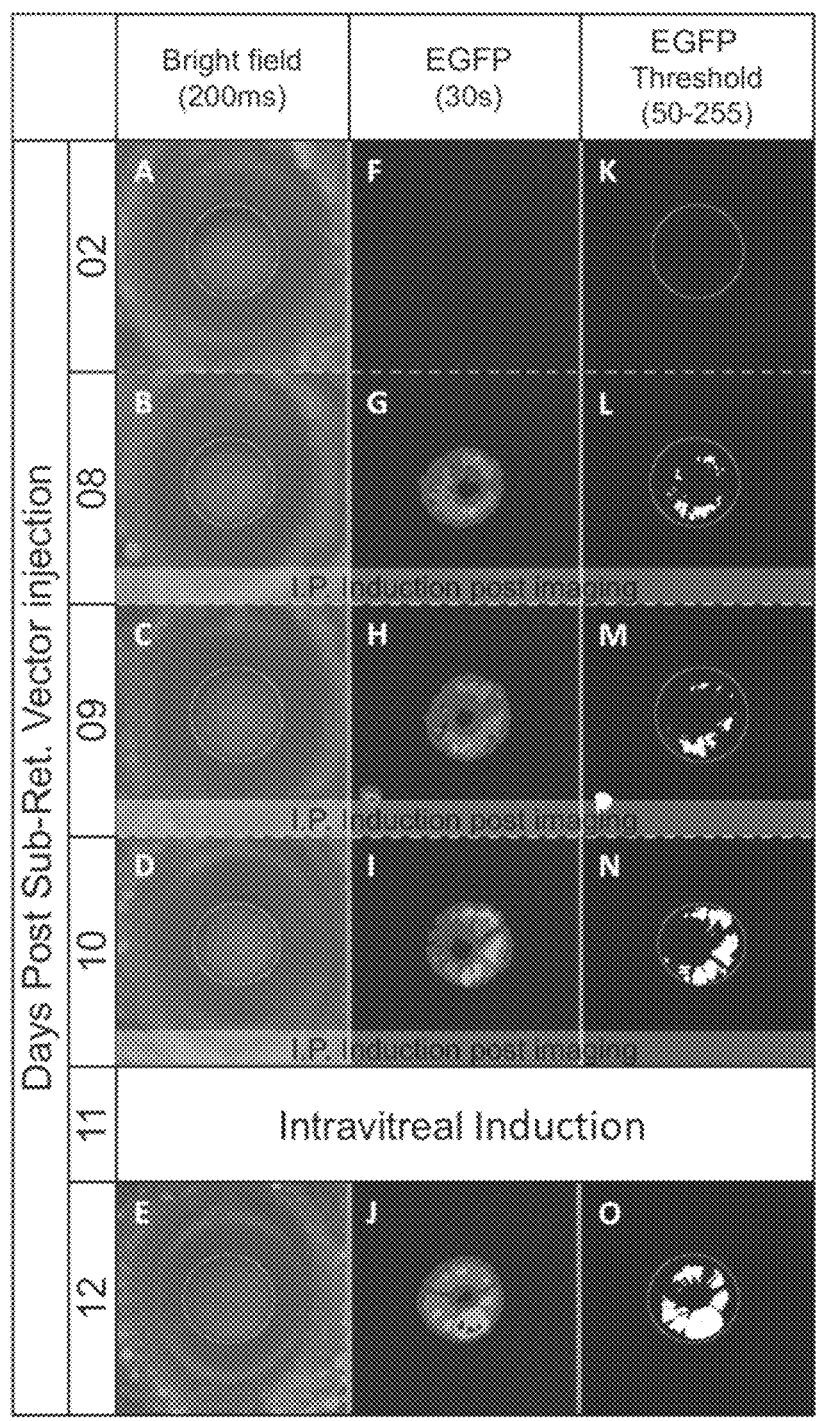
Figure 13B:
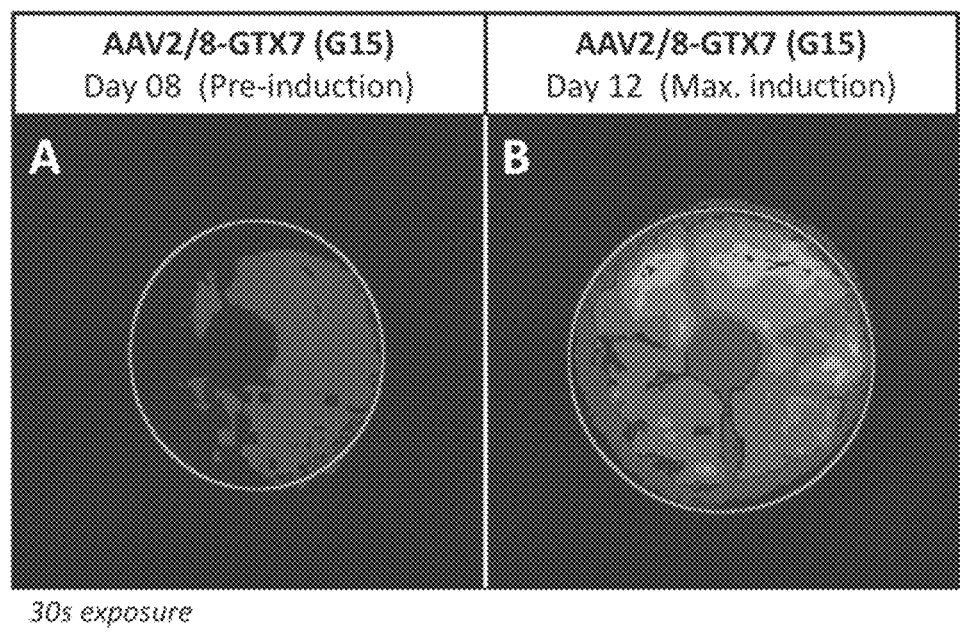

FIGS. 13a and 13b. Representative fundus images of a single murine eye subretinally injected with AAV2/8-GTX7 showing variation in EGFP transgene expression in the retina over time. A-E: Images taken under white light illumination with an exposure time of 200 ms at 2, 8, 9, 10 and 12 days post vector injection. Circle shows area of retina visible through the pupil that was taken as the ROI for quantification. F-J: Images taken under 475±25 nm light illumination with an exposure time of 30 s. showing eGFP fluorescence at 2, 8, 9, 10 and 12 days post vector injection. K-O: Images taken under 475±25 nm light illumination with an exposure time of 30 s at 2, 8, 9, 10 and 12 days post vector injection highlighting pixels above an intensity threshold of 50 within the ROI (circle). FIG. 13b shows high-resolution images pre (A) and post (B) induction.

Figure 13C:
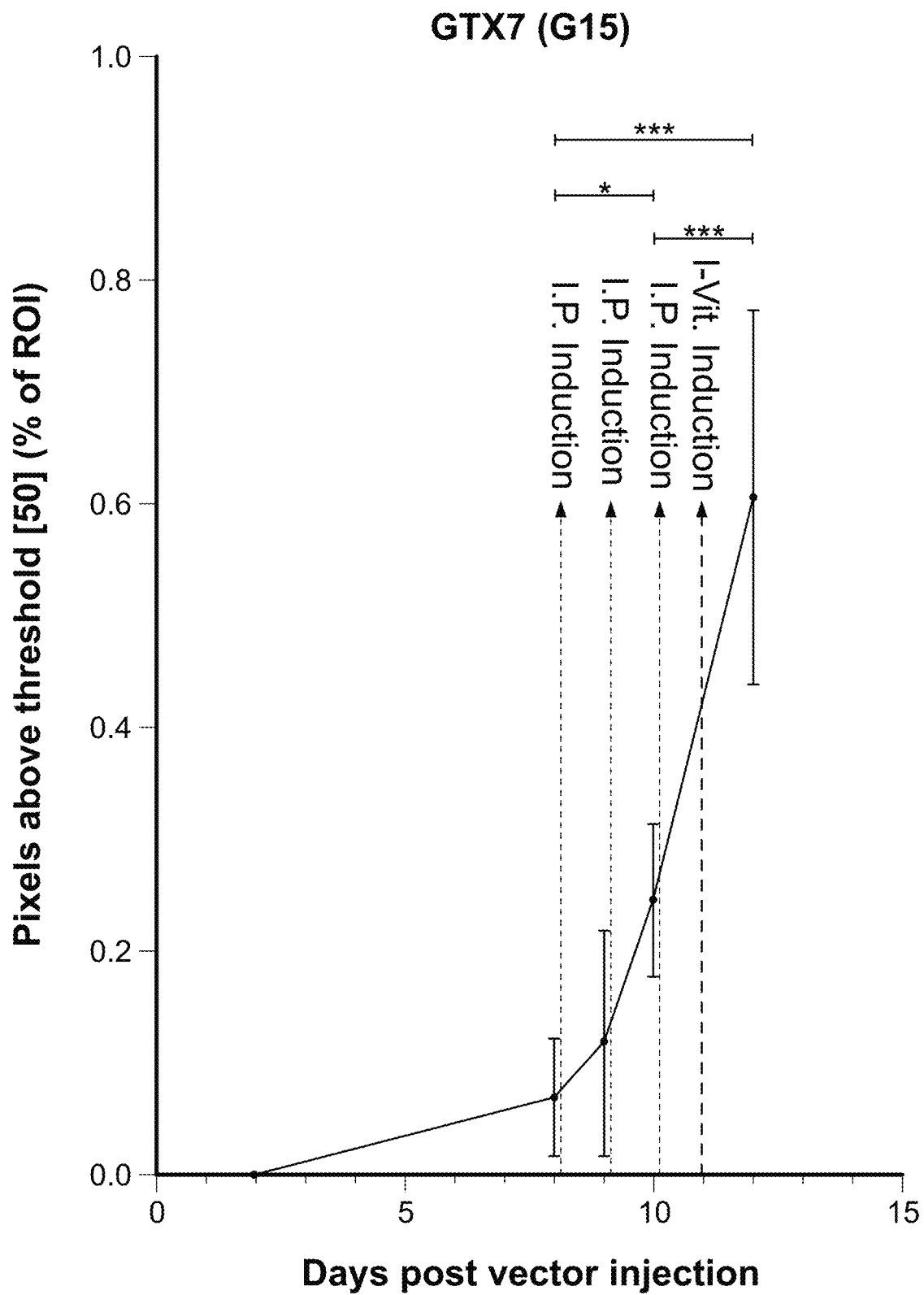

FIG. 13c. EGFP transgene expression in the murine retina quantified over time after subretinal injection of AAV2/8-GTX7. Fluorescent fundus photographs were taken at the following time points: 2, 8, 9, 10 and 12 days post subretinal injection of AAV2/8-GTX7. Exposure time: 30 s, pixel intensity threshold for analysis: 50. Intraperitoneal induction was carried out after imaging at 8, 9 and 10 days post subretinal injection of AAV2/8-GTX7. In addition, intravitreal induction was carried out at 11 days post subretinal injection of AAV2/8-GTX7. Statistical significance shown based upon 1-way ANOVA with Dunnetts correction and 8 days post injection as the control point.

Figure 13D:
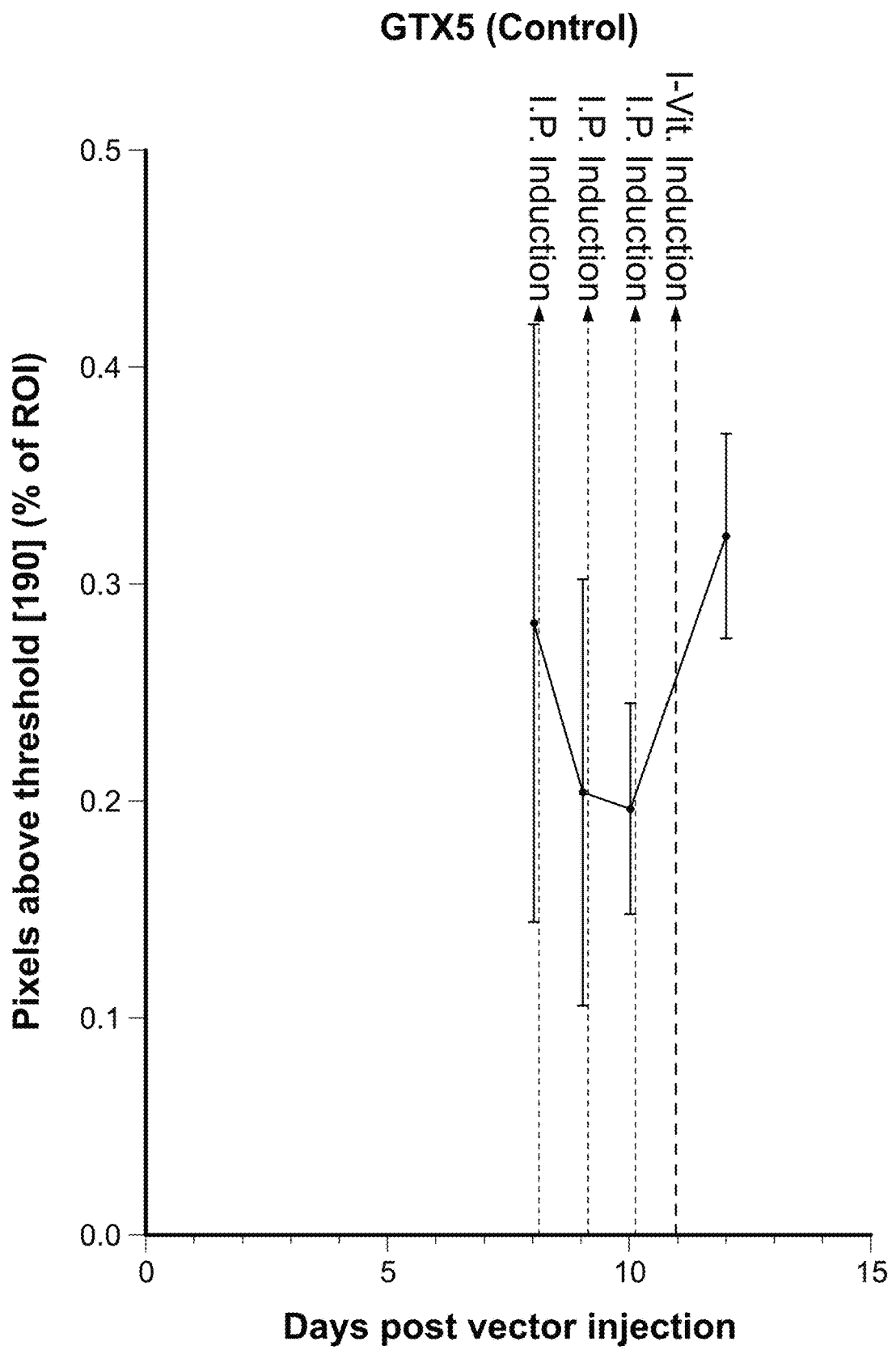

FIG. 13d. EGFP transgene expression in the murine retina quantified over time post subretinal injection of AAV2/8-GTX5 (positive control). Fluorescent fundus photographs were taken at the following time points: 2, 8, 9, 10 and 12 days post subretinal injection of AAV2/8-GTX5. Exposure time: 10 s, pixel intensity threshold for analysis: 190. Intraperitoneal administration of guanosine was carried out after imaging at 8, 9 and 10 days post subretinal injection of AAV2/8-GTX5. In addition, intravitreal administration of guanosine was carried out at 11 days post subretinal injection of AAV2/8-GTX5. One-way ANOVA with Bonferroni correction was applied, and no statistically significant differences in expression of EGFP were found on treatment with guanosine.

DETAILED DESCRIPTION

The present invention provides a gene regulation cassette that comprises a riboswitch in the context of a 5' intron-alternative exon-3' intron. The gene regulation cassette refers to a recombinant DNA construct that when incorporated into the DNA of a target gene provides the ability to regulate expression of the target gene by aptamer/ligand mediated alternative splicing of the resulting pre-mRNA. The riboswitch in the context of the present invention contains a sensor region (e.g., an aptamer) and an effector region that together are responsible for sensing the presence of a small molecule ligand and altering splicing to an alternative exon. In one embodiment, the target gene's expression is increased when the aptamer ligand is present and decreased when the ligand is absent.

Riboswitch

The term "riboswitch" as used herein refers to a regulatory segment of a RNA polynucleotide. A riboswitch in the context of the present invention contains a sensor region (e.g., an aptamer) and an effector region that together are responsible for sensing the presence of a ligand (e.g., a small molecule) and altering splicing to an alternative exon. In one embodiment, the riboswitch is recombinant, utilizing polynucleotides from two or more sources. The term "synthetic" as used herein in the context of a riboswitch refers to a riboswitch that is not naturally occurring. In one embodiment, the sensor and effector regions are joined by a polynucleotide linker. In one embodiment, the polynucleotide linker forms a RNA stem (i.e., a region of the RNA polynuceotide that is double-stranded).

Effector Region

Figure 4A:
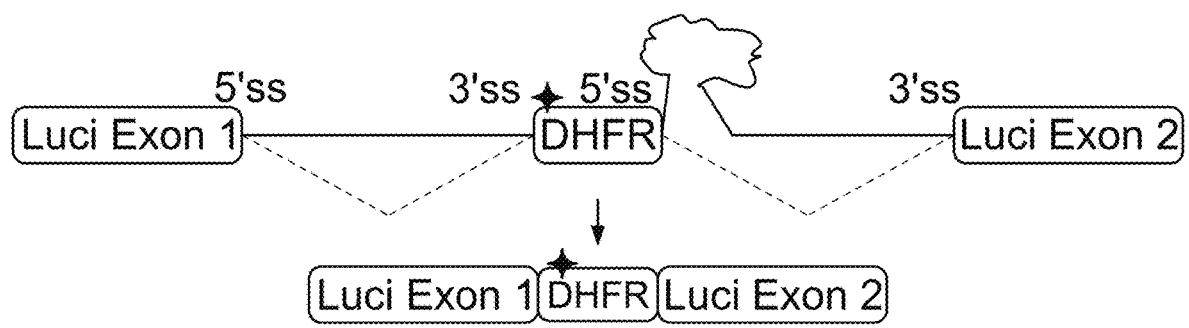
Figure 4B:
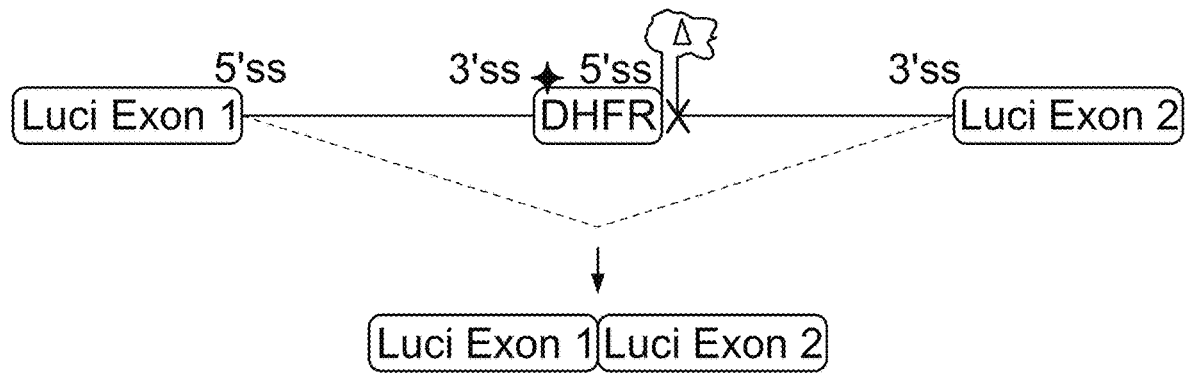
FIG. 4b. Schematic diagram of gene regulation by the Intron-Exon-Intron regulatory cassette containing synthetic riboswitch. In the absence of aptamer/ligand binding, the aptamer sequence disrupts hairpin stem formation, leaving the DHFR exon 5'ss accessible and leading to inclusion of the DHFR exon, thus preventing translation and blocking protein expression (FIG. 4a). When aptamer/ligand binding occurs, ligand-dependent conformational changes in the aptamer stabilize stem formation, sequestering the DHFR exon 5'ss, resulting in DHFR exon exclusion and luciferase gene expression (FIG. 4b).
Figure 4C:
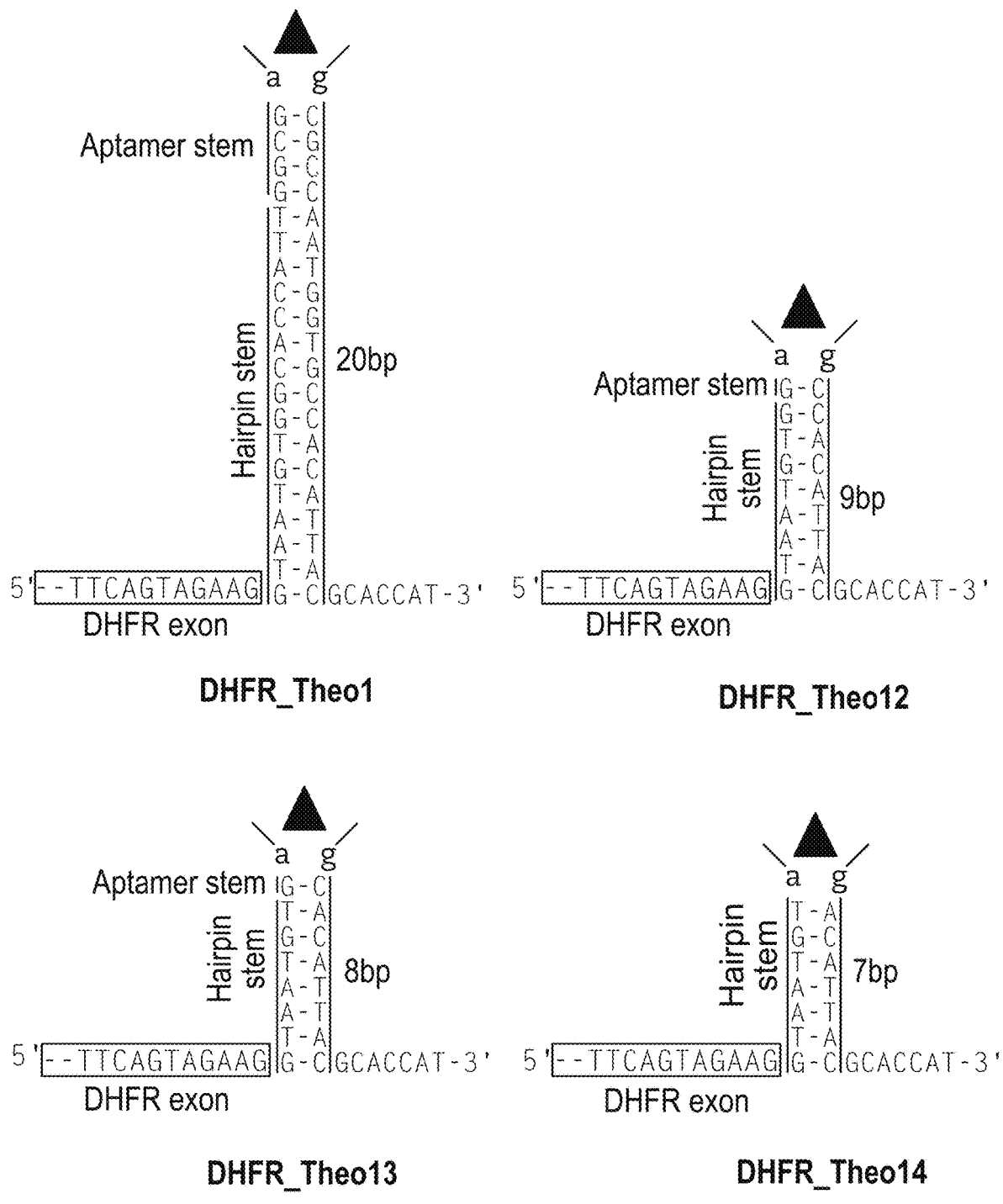
FIG. 4c. Hairpin stem and theophylline aptamer configurations with different connecting stem lengths. The stem of the theophylline aptamer was directly linked to the stem of the hairpin sequestering the DHFR exon 5'ss, generating a 20 bp synthetic stem. The stem sequence was truncated, generating a series of hairpins with different stem lengths. Shown are the stem structures for DHFR_Theo1, 12, 13 and 14 with stem lengths of 20 bp, 9 bp, 8 bp and 7 bp respectively. Theophylline is symbolized as (▲). DHFR_Theo1 (SEQ ID NO: 70 and SEQ ID NO:71); DHFR_Theo12 (SEQ ID NO:72 and SEQ ID NO:73); DHFR_Theo13 (SEQ ID NO: 74 and SEQ ID NO:75); DHFR_Theo14 (SEQ ID NO:76 and SEQ ID NO:77).
Figure 4D:
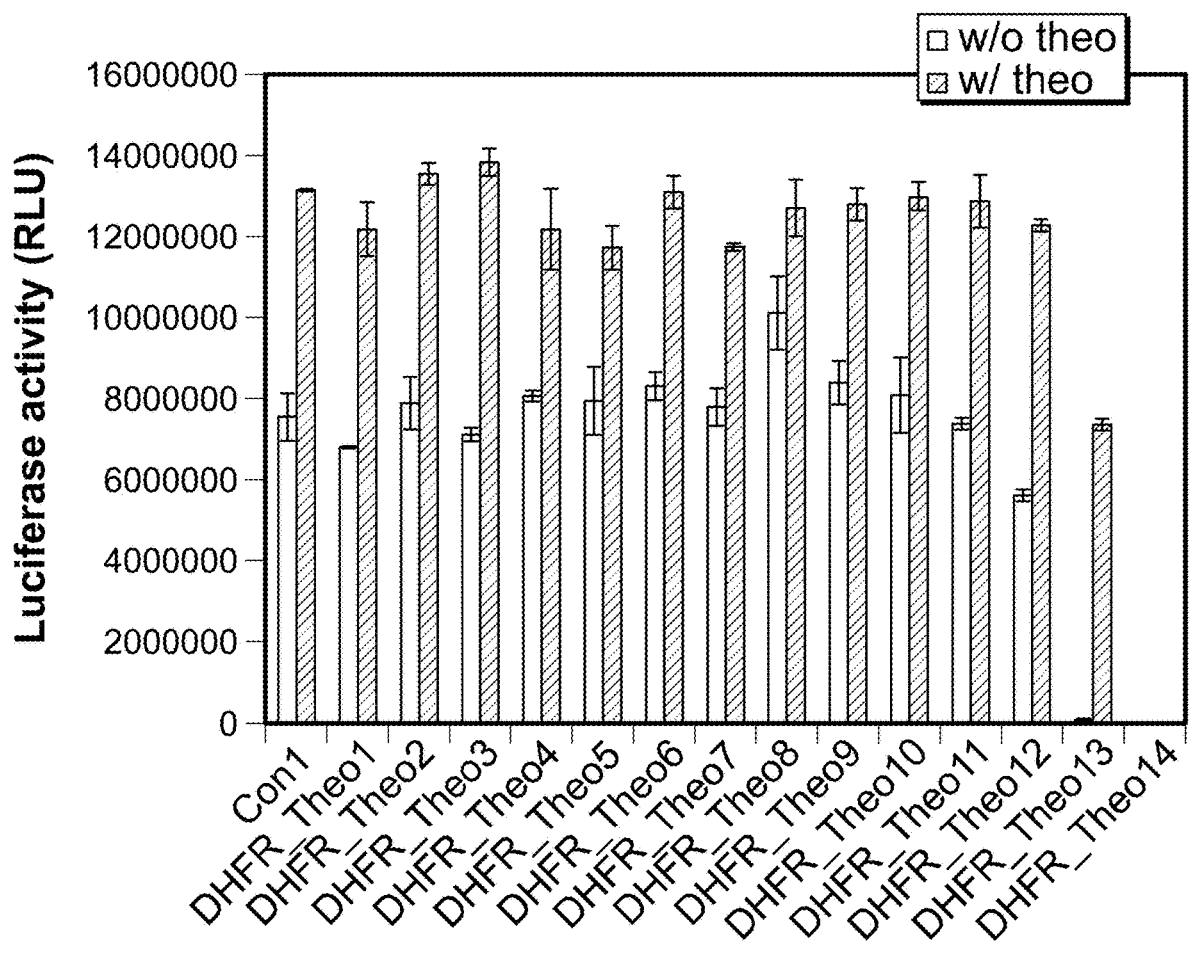
FIG. 4d. Effect of different stem lengths using the theophylline aptamer on target gene expression in the presence and absence of theophylline. Graph showing luciferase expression regulated by theophylline aptamer containing regulatory cassettes that were generated as described in Example 4 (FIG. 4c). In constructs Theo 1 through 12, with stem lengths of 20 bp down to 9 bp, the hairpin stem was of sufficient length to form a stable structure in the absence of aptamer/ligand binding. DHFR_Theo13, does not form a stable hairpin stem in the absence of ligand, thus the DHFR exon 5'ss is not hidden resulting in inclusion of DHFR exon, blocking luciferase expression. In the presence of theophylline the hairpin is stabilized and the DHFR exon 5'ss is inaccessible to splicing machinery. This results in exclusion of the DHFR exon allowing luciferase expression. In the presence of 3 mM theophylline, DHFR_Theo_13 demonstrates 43-fold induction over the un-induced baseline level of expression. DHFR_Theo_14 shows no luciferase expression either with or without theophylline present, suggesting that this 7 bp stem is too short to form a stable hairpin even when the aptamer binds to its ligand. As a result, the DHFR exon is spliced into the transcript and luciferase expression is blocked.

In one embodiment, the effector region comprises the 5' splice site ("5'ss") sequence of the 3' intron (i.e., the intronic splice site sequence that is immediately 3' of the alternative exon). The effector region comprises the 5' ss sequence of the 3' intron and sequence complimentary to the 5' ss sequence of the 3' intron. When the aptamer binds its ligand, the effector region forms a stem and thus prevents splicing to the splice donor site at the 3' end of the alternative exon (see, e.g., FIG. 4b). Under certain conditions (for example, when the aptamer is not bound to its ligand), the effector region is in a context that provides access to the splice donor site at the 3' end of the alternative exon leading to inclusion of the alternative exon in the target gene mRNA (see, e.g., FIG. 4a).

The stem portion of the effector region should be of a sufficient length (and GC content) to substantially prevent alternative splicing of the alternative exon upon ligand binding the aptamer, while also allowing access to the splice site when the ligand is not present in sufficient quantities. In embodiments of the invention, the stem portion of the effector region comprises stem sequence in addition to the 5' ss sequence of the 3' intron and its complementary sequence. In embodiments of the invention, this additional stem sequence comprises sequence from the aptamer stem. The length and sequence of the stem portion can be modified using known techniques in order to identify stems that allow acceptable background expression of the target gene when no ligand is present and acceptable expression levels of the target gene when the ligand is present (see, e.g., Examples 4 and 5 and FIGS. 4c and 4d, 5a, 5b, 5c, 5d). If the stem is, for example, too long it may hide access to the 5' ss sequence of the 3' intron in the presence or absence of ligand. If the stem is too short, it may not form a stable stem capable of sequestering the 5' ss sequence of the 3' intron, in which case the alternative exon will be spliced into the target gene message in the presence or absence of ligand. In one embodiment, the total length of the effector region stem is between about 7 base pairs to about 20 base pairs. In some embodiments, the length of the stem is between about 8 base pairs to about 11 base pairs. In some embodiments, the length of the stem is 8 base pairs to 11 base pairs. In addition to the length of the stem, the GC base pair content of the stem can be altered to modify the stability of the stem.

Aptamer/Ligand

The term "aptamer" as used herein refers to an RNA polynucleotide that specifically binds to a ligand. The term "ligand" refers to a molecule that is specifically bound by the aptamer. In one embodiment, the ligand is a low molecular weight (less than about 1,000 Daltons) molecule including, for example, lipids, monosaccharides, second messengers, other natural products and metabolites, nucleic acids, as well as most therapeutic drugs In one embodiment the ligand is a polynucleotide with 2 or more nucleotide bases.

Aptamers have binding regions, which are capable of forming complexes with an intended target molecule (i.e., the ligand). The specificity of the binding can be defined in terms of the comparative dissociation constants (Kd) of the aptamer for its ligand as compared to the dissociation constant of the aptamer for unrelated molecules. Thus, the ligand is a molecule that binds to the aptamer with greater affinity than to unrelated material. Typically, the Kd for the aptamer with respect to its ligand will be at least about 10-fold less than the Kd for the aptamer with unrelated molecules. In other embodiments, the Kd will be at least about 20-fold less, at least about 50-fold less, at least about 100-fold less, and at least about 200-fold less. An aptamer will typically be between about 15 and about 200 nucleotides in length. More commonly, an aptamer will be between about 30 and about 100 nucleotides in length.

The aptamers that can be incorporated as part of the riboswitch can be a naturally occurring aptamer, or modifications thereof, or aptamers that are designed de novo or synthetic screened through systemic evolution of ligands by exponential enrichment (SELEX). Examples of aptamers that bind small molecule ligands include, but are not limited to theophylline, dopamine, sulforhodamine B, and cellobiose kanamycin A, lividomycin, tobramycin, neomycin B, viomycin, chloramphenicol, streptomycin, cytokines, cell surface molecules, and metabolites. For a review of aptamers that recognize small molecules, see, e.g., Famulok, Science 9:324-9 (1999) and Mckeague, M. & DeRosa, M. C. J. Nuc. Aci. 2012. In another embodiment, the aptamer is a complementary polynucleotide.

In one embodiment, the aptamer is designed to bind a particular small molecule ligand. Methods for designing aptamers include for example SELEX. Methods for designing aptamers that selectively bind a small molecule using SELEX are disclosed in, e.g., U.S. Pat. Nos. 5,475,096, 5,270,163, and Abdullah Ozer, et al. Nuc. Aci. 2014, which are incorporated herein by reference. Modifications of the SELEX process are described in U.S. Pat. Nos. 5,580,737 and 5,567,588, which are incorporated herein by reference.

Selection techniques for identifying aptamers generally involve preparing a large pool of DNA or RNA molecules of the desired length that contain a region that is randomized or mutagenized. For example, an oligonucleotide pool for aptamer selection might contain a region of 20-100 randomized nucleotides flanked by regions of defined sequence that are about 15-25 nucleotides long and useful for the binding of PCR primers. The oligonucleotide pool is amplified using standard PCR techniques, or other means that allow amplification of selected nucleic acid sequences. The DNA pool may be transcribed in vitro to produce a pool of RNA transcripts when an RNA aptamer is desired. The pool of RNA or DNA oligonucleotides is then subjected to a selection based on their ability to bind specifically to the desired ligand. Selection techniques include, for example, affinity chromatography, although any protocol which will allow selection of nucleic acids based on their ability to bind specifically to another molecule may be used. Selection techniques for identifying aptamers that bind small molecules and function within a cell may involve cell based screening methods. In the case of affinity chromatography, the oligonucleotides are contacted with the target ligand that has been immobilized on a substrate in a column or on magnetic beads. The oligonucleotide is preferably selected for ligand binding in the presence of salt concentrations, temperatures, and other conditions which mimic normal physiological conditions. Oligonucleotides in the pool that bind to the ligand are retained on the column or bead, and nonbinding sequences are washed away. The oligonucleotides that bind the ligand are then amplified (after reverse transcription if RNA transcripts were utilized) by PCR (usually after elution). The selection process is repeated on the selected sequences for a total of about three to ten iterative rounds of the selection procedure. The resulting oligonucleotides are then amplified, cloned, and sequenced using standard procedures to identify the sequences of the oligonucleotides that are capable of binding the target ligand. Once an aptamer sequence has been identified, the aptamer may be further optimized by performing additional rounds of selection starting from a pool of oligonucleotides comprising a mutagenized aptamer sequence.

In vivo aptamer screening may be used following one or more rounds of in vitro selection (e.g., SELEX). For example, Konig, J. et al. (RNA. 2007, 13 (4): 614-622, incorporated herein by reference) describe combining SELEX and a yeast three-hybrid system for in vivo selection of aptamer.

The Alternative Exon

The alternative exon that is part of the gene regulation polynucleotide cassette of the present invention can be any polynucleotide sequence capable of being transcribed to a pre-mRNA and alternatively spliced into the mRNA of the target gene. The alternative exon that is part of the gene regulation cassette of the present invention contains at least one sequence that inhibits translation such that when the alternative exon is included in the target gene mRNA, expression of the target gene from that mRNA is prevented or reduced. In a preferred embodiment, the alternative exon contains a stop codon (TGA, TAA, TAG) that is in frame with the target gene when the alternative exon is included in the target gene mRNA by splicing. In embodiments, the alternative exon comprises, in addition to a stop codon, or as an alternative to a stop codon, other sequence that reduces or substantially prevents translation when the alternative exon is incorporated by splicing into the target gene mRNA including, e.g., a microRNA binding site, which leads to degradation of the mRNA. In one embodiment, the alternative exon comprises a miRNA binding sequence that results in degradation of the mRNA. In one embodiment, the alternative exon encodes a polypeptide sequence which reduces the stability of the protein containing this polypeptide sequence. In one embodiment, the alternative exon encodes a polypeptide sequence which directs the protein containing this polypeptide sequence for degradation.

The basal or background level of splicing of the alternative exon can be optimized by altering exon splice enhancer (ESE) sequences and exon splice suppressor (ESS) sequences and/or by introducing ESE or ESS sequences into the alternative exon. Such changes to the sequence of the alternative exon can be accomplished using methods known in the art, including, but not limited to site directed mutagenesis. Alternatively, oligonucleotides of a desired sequence (e.g., comprising all or part of the alternative exon) can be obtained from commercial sources and cloned into the gene regulation cassette. Identification of ESS and ESE sequences can be accomplished by methods known in the art, including, for example using ESEfinder 3.0 (Cartegni, L. et al. ESEfinder: a web resource to identify exonic splicing enhancers. Nucleic Acid Research, 2003, 31 (13): 3568-3571) and/or other available resources.

In one embodiment, the alternative exon is exogenous to the target gene, although it may be derived from a sequence originating from the organism where the target gene will be expressed. In one embodiment the alternative exon is a synthetic sequence (see Example 10).

In one embodiment, the alternative exon is a naturally-occurring exon (see Example 10). In another embodiment, the alternative exon is derived from all or part of a known exon (see Example 10). In this context, "derived" refers to the alternative exon containing sequence that is substantially homologous to a naturally occurring exon, or a portion thereof, but may contain various mutations, for example, to introduce a stop codon that will be in frame with the target gene sequence, or to introduce or delete an exon splice enhancer, and/or introduce delete an exon splice suppressor. In one embodiment, the alternative exon is derived from exon 2 of the human dihydrofolate reductase gene (DHFR), mutant human Wilms tumor 1 exon 5, mouse calcium/calmodulin-dependent protein kinase II delta exon 16, or SIRT1 exon 6.

5' and 3' Intronic Sequences

The alternative exon is flanked by 5' and 3' intronic sequences. The 5' and 3' intronic sequences that can be used in the gene regulation cassette of the present invention can be any sequence that can be spliced out of the target gene creating either the target gene mRNA or the target gene comprising the alternative exon in the mRNA, depending upon the presence or absence of a ligand that binds the aptamer. The 5' and 3' introns each has the sequences necessary for splicing to occur, i.e., splice donor, splice acceptor and branch point sequences. In one embodiment, the 5' and 3' intronic sequences of the gene regulation cassette are derived from one or more naturally occurring introns or a portion thereof. In one embodiment, the 5' and 3' intronic sequences are derived from a truncated human beta-globin intron 2 (IVS2Δ). In other embodiements the 5' and 3' intronic sequences are derived from the SV40 mRNA intron (used in pCMV-LacZ vector from Clonetech), intron 6 of human triose phosphate isomerase (TPI) gene (Nott Ajit, et al. RNA. 2003, 9:6070617), or an intron from human factor IX (Sumiko Kurachi et al. J. Bio. Chem. 1995, 270 (10), 5276), the target gene's own endogenous intron, or any genomic fragment or synthetic introns (Yi Lai, et al. Hum Gene Ther. 2006: 17 (10): 1036) that contain elements that are sufficient for regulated splicing (Thomas A. Cooper, Methods 2005 (37): 331).

In one embodiment, the alternative exon and riboswitch of the present invention are engineered to be in an endogenous intron of a target gene. That is, the intron (or substantially similar intronic sequence) naturally occurs at that position of the target gene. In this case, the intronic sequence immediately upstream of the alternative exon is referred to as the 5' intron or 5'intronic sequence, and the intronic sequence immediately downstream of the alternative exon is referred to as the 3' intron or 3' intronic sequence. In this case, the endogenous intron is modified to contain a splice acceptor sequence and splice donor sequence flanking the 5' and 3' ends of the alternative exon.

The splice donor and splice acceptor sites in the gene regulation cassette of the present invention can be modified to be strengthened or weakened. That is, the splice sites can be modified to be closer to the consensus for a splice donor or acceptor by standard cloning methods, site directed mutagenesis, and the like. Splice sites that are more similar to the splice consensus tend to promote splicing and are thus strengthened. Splice sites that are less similar to the splice consensus tend to hinder splicing and are thus weakened. The consensus for the splice donor of the most common class of introns (U2) is A/C A G∥GT A/G A G T (where ∥ denotes the exon/intron boundary). The consensus for the splice acceptor is C A G∥G (where ∥ denotes the exon/intron boundary). The frequency of particular nucleotides at the splice donor and acceptor sites are described in the art (see, e.g., Zhang, M. Q., Hum Mol Genet. 1988. 7 (5): 919-932). The strength of 5'ss and 3' splice sites can be adjusted to modulate splicing of the alternative exon.

Additional modifications to 5' and 3' introns in the gene regulation cassette can be made to modulate splicing including modifying, deleting, and/or adding intronic splicing enhancer elements and/or intronic splicing suppressor elements, and/or modifying the branch site sequence.

In one embodiment, the 5' intron has been modified to contain a stop codon that will be in frame with the target gene. The 5' and 3' intronic sequences can also be modified to remove cryptic slice sites, which can be identified with publicly available software (see, e.g., Kapustin, Y. et al. Nucl. Acids Res. 2011. 1-8). The lengths of the 5' and 3' intronic sequences can be adjusted in order to, for example, meet the size requirements for viral expression constructs. In one embodiment, the 5' and 3' intronic sequences are independently from about 50 to about 300 nucleotides in length. In one embodiment, the 5' and 3' intronic sequences are independently from about 125 to about 240 nucleotides in length.

Target Genes

The gene regulation cassette of the present invention is a platform that can be used to regulate the expression of any target gene that can be expressed in a target cell, tissue or organism. The term "target gene" refers to a polynucleotide that is introduced into a cell and is capable of being transcribed into RNA and translated and/or expressed under appropriate conditions. Alternatively, the target gene is endogenous to the target cell and the gene regulation cassette of the present invention is positioned into the target gene (for example into an existing intron of the endogenous target gene). An example of a target gene is a polynucleotide encoding a therapeutic polypeptide. In one embodiment, when the target gene is expressed using the gene regulation cassette of the present invention, the target gene is not expressed as a fusion protein comprising the alternative exon. Inclusion of the alternative exon minimizes translation of the mRNA by, e.g., causing degradation of the message containing the alternative exon, or otherwise prevents expression of a functional target gene due, e.g., to its premature truncation. In one embodiment, the target gene is exogenous to the cell in which the recombinant DNA construct is to be transcribed. In another embodiment, the target gene is endogenous to the cell in which the recombinant DNA construct is to be transcribed. The alternative exon, in one embodiment, may contain a stop codon in frame with the coding sequence of the target gene. In other embodiments, the alternative exon may contain other sequences that drive transcript degradation and/or block translation of the target gene.

The target gene according to the present invention may be a gene encoding a protein, or a sequence encoding a non-protein coding RNA. The target gene may be, for example, a gene encoding a structural protein, an enzyme, a cell signaling protein, a mitochondrial protein, a zinc finger protein, a hormone, a transport protein, a growth factor, a cytokine, an intracellular protein, an extracellular protein, a transmembrane protein, a cytoplasmic protein, a nuclear protein, a receptor molecule, an RNA binding protein, a DNA binding protein, a transcription factor, translational machinery, a channel protein, a motor protein, a cell adhesion molecule, a mitochondrial protein, a metabolic enzyme, a kinase, a phosphatase, exchange factors, a chaperone protein, and modulators of any of these. In embodiments, the target gene encodes erythropoietin (Epo), human growth hormone (hGH), transcription activator-like effector nucleases (TALEN), human insulin, CRISPR associated protein 9 (cas9), or an immunoglobulin (or portion thereof), including, e.g., a therapeutic antibody.

Expression Constructs

The present invention contemplates the use of a recombinant vector for introduction into target cells a polynucleotide encoding a target gene and containing the gene regulation cassette of the present invention. In many embodiments, the recombinant DNA construct of this invention includes additional DNA elements including DNA segments that provide for the replication of the DNA in a host cell and expression of the target gene in that cell at appropriate levels. The ordinarily skilled artisan appreciates that expression control sequences (promoters, enhancers, and the like) are selected based on their ability to promote expression of the target gene in the target cell. "Vector" means a recombinant plasmid, yeast artificial chromosome (YAC), mini chromosome, DNA mini-circle or virus (including virus derived sequences) that comprises a polynucleotide to be delivered into a host cell, either in vitro or in vivo. In one embodiment, the recombinant vector is a viral vector or a combination of multiple viral vectors.

Viral vectors for the expression of a target gene in a target cell, tissue, or organism are known in the art and include adenoviral (AV) vectors, adeno-associated virus (AAV) vectors, retroviral and lentiviral vectors, and Herpes simplex type 1 (HSV1) vectors.

Adenoviral vectors include, for example, those based on human adenovirus type 2 and human adenovirus type 5 that have been made replication defective through deletions in the E1 and E3 regions. The transcriptional cassette can be inserted into the E1 region, yielding a recombinant E1/E3-deleted AV vector. Adenoviral vectors also include helper-dependent high-capacity adenoviral vectors (also known as high-capacity, "gutless" or "gutted" vectors), which do not contain viral coding sequences. These vectors, contain the cis-acting elements needed for viral DNA replication and packaging, mainly the inverted terminal repeat sequences (ITR) and the packaging signal (Y'). These helper-dependent AV vector genomes have the potential to carry from a few hundred base pairs up to approximately 36 kb of foreign DNA.

Recombinant adeno-associated virus "rAAV" vectors include any vector derived from any adeno-associated virus serotype, including, without limitation, AAV-1, AAV-2, AAV-3, AAV-4, AAV-5, AAV-7 and AAV-8, AAV-9, AAV-10, and the like. rAAV vectors can have one or more of the AAV wild-type genes deleted in whole or in part, preferably the Rep and/or Cap genes, but retain functional flanking ITR sequences. Functional ITR sequences are retained for the rescue, replication, packaging and potential chromosomal integration of the AAV genome. The ITRs need not be the wild-type nucleotide sequences, and may be altered (e.g., by the insertion, deletion or substitution of nucleotides) so long as the sequences provide for functional rescue, replication and packaging.

Alternatively, other systems such as lentiviral vectors can be used in embodiments of the invention. Lentiviral-based systems can transduce nondividing as well as dividing cells making them useful for applications targeting, for examples, the non-dividing cells of the CNS. Lentiviral vectors are derived from the human immunodeficiency virus and, like that virus, integrate into the host genome providing the potential for very long-term gene expression.

Polynucleotides, including plasmids, YACs, minichromosomes and minicircles, carrying the target gene containing the gene regulation cassette can also be introduced into a cell or organism by nonviral vector systems using, for example, cationic lipids, polymers, or both as carriers. Conjugated poly-L-lysine (PLL) polymer and polyethylenimine (PEI) polymer systems can also be used to deliver the vector to cells. Other methods for delivering the vector to cells includes hydrodynamic injection and electroporation and use of ultrasound, both for cell culture and for organisms. For a review of viral and non-viral delivery systems for gene delivery see Nayerossadat, N. et al. (Adv Biomed Res. 2012; 1:27) incorporated herein by reference.

Methods of Modulating Expression of a Target Gene

In one aspect, this invention provides a method of modulating expression of a target gene (e.g., a therapeutic gene), by (a) inserting the gene regulation cassette of the present invention into a target gene; (b) introducing the target gene comprising the gene regulation cassette into a cell; and (c) exposing the cell to a ligand that binds the aptamer. In one embodiment, the ligand is a small molecule. In aspects, expression of the target gene in target cells confers a desired property to a cell into which it was introduced, or otherwise leads to a desired therapeutic outcome.

In a preferred embodiment, the gene regulation cassette is inserted into the protein coding sequence of the target gene (rather than in the 5' or 3' untranslated regions). In one embodiment, a single gene regulation cassette is inserted into the target gene. In other embodiments 2, 3, 4, or more gene regulation cassettes are inserted in the target gene. In one embodiment, two gene regulation cassettes are inserted into the target gene. When multiple gene regulation cassettes are inserted into a target gene, they each can contain the same aptamer such that a single ligand can be used to modulate alternative splicing at the multiple cassettes and thereby modulate target gene expression. In other embodiments, multiple gene regulation cassettes are inserted into a target gene, each can contain a different aptamer so that exposure to multiple different small molecule ligands modulates target gene expression. In other embodiments, multiple gene regulation cassettes are inserted into a target gene, each containing different 5' intron, alternative exon, and 3' intron sequences. This may be useful in reducing recombination and improving ease of incorporation into viral vectors.

Methods of Treatment and Pharmaceutical Compositions

One aspect of the invention provides a method of regulating the level of a therapeutic protein delivered by gene therapy. In this embodiment, the "target gene" may encode the therapeutic protein. The "target gene" may encode a protein that is endogenous or exogenous to the cell.

The therapeutic gene sequence containing the regulatory cassette with aptamer-driven riboswitch is delivered to the target cells in the body, e.g., by a vector. The cell specificity of the "target gene" may be controlled by promoter or other elements within the vector. Delivery of the vector construct containing the target gene, and the transfection of the target tissues resulting in stable transfection of the regulated target gene, is the first step in producing the therapeutic protein.

However, due to the presence of the regulatory cassette within the target gene sequence, the target gene is not expressed at significant levels, i.e., it is in the "off state" in the absence of the specific ligand that binds to the aptamer contained within in the regulatory cassette riboswitch. Only when the aptamer specific ligand is administered is the target gene expression activated.

The delivery of the vector construct containing the target gene and the delivery of the activating ligand generally are separated in time. The delivery of the activating ligand will control when the target gene is expressed, as well as the level of protein expression. The ligand may be delivered by a number of routes including, but not limited to, oral, intramuscular (IM), intravenous (IV), intraocular, or topically.

The timing of delivery of the ligand will depend on the requirement for activation of the target gene. For example, if the therapeutic protein encoded by the target gene is required constantly, an oral small molecule ligand may be delivered daily, or multiple times a day, to ensure continual activation of the target gene, and thus continual expression of the therapeutic protein. If the target gene has a long acting effect, the inducing ligand may be dosed less frequently.

This invention allows the expression of the therapeutic transgene to be controlled temporally, in a manner determined by the temporal dosing of the ligand specific to the aptamer within the regulatory cassette. The expression of the therapeutic transgene only on ligand administration, increases the safety of a gene therapy treatment by allowing the target gene to be off in the absence of the ligand.

Different aptamers can be used to allow different ligands to activate target genes. In certain embodiments of the invention, each therapeutic gene containing a regulatory cassette will have a specific aptamer within the cassette that will be activated by a specific small molecule. This means that each therapeutic gene can be activated only by the ligand specific to the aptamer housed within it. In these embodiments, each ligand will only activate one therapeutic gene. This allows for the possibility that several different "target genes" may be delivered to one individual and each will be activated on delivery of the specific ligand for the aptamer contained within the regulatory cassette housed in each target gene.

This invention allows any therapeutic protein whose gene can be delivered to the body (such as erythropoietin (EPO) or a therapeutic antibody) to be produced by the body when the activating ligand is delivered. This method of therapeutic protein delivery may replace the manufacture of such therapeutic proteins outside of the body which are then injected or infused, e.g., antibodies used in cancer or to block inflammatory or autoimmune disease. The body containing the regulated target gene becomes the biologics manufacturing factory, which is switched on when the gene-specific ligand is administered.

Dosing levels and timing of dosing of a therapeutic protein may be critical to therapeutic effect. For example in the delivery of AVASTIN® (anti-VEGF antibody) for cancer. The present invention increases the ease of dosing in response to monitoring for therapeutic protein levels and effects.

In one embodiment, the target protein may be a nuclease that can target and edit a particular DNA sequence. Such nucleases include Cas9, zinc finger containing nucleases, or TALENs. In the case of these nucleases, the nuclease protein may be required for only a short period of time that is sufficient to edit the target endogenous genes.

However, if an unregulated nuclease gene is delivered to the body, this protein may be present for the rest of the life of the cell. In the case of nucleases, there is an increasing risk of off-target editing the longer the nuclease is present. Regulation of expression of such proteins has a significant safety advantage. In this case, vector containing the nuclease target gene containing a regulatory cassette could be delivered to the appropriate cells in the body. The target gene is in the "off" state in the absence of the cassette-specific ligand, so no nuclease is produced. Only when the activating ligand is administered, is the nuclease produced. When sufficient time has elapsed allowing sufficient editing to occur, the ligand will be withdrawn and not administered again. Thus the nuclease gene is thereafter in the "off" state and no further nuclease is produced and editing stops. This approach may be used to correct genetic conditions, including a number of inherited retinopathies such as LCA10 caused by mutations in CEP290 and Stargardts disease caused by mutations in ABCA4.

Administration of a regulated target gene encoding a therapeutic protein which is activated only on specific ligand administration may be used to regulate therapeutic genes to treat many different types of diseases, e.g., cancer with therapeutic antibodies, immune disorders with immune modulatory proteins or antibodies, metabolic diseases, rare diseases such as PNH with anti-C5 antibodies or antibody fragments as the regulated gene, or ocular angiogenesis with therapeutic antibodies, and dry AMD with immune modulatory proteins.

A wide variety of specific target genes, allowing for the treatment of a wide variety of specific diseases and conditions, are suitable for use in the present invention. For example, insulin or an insulin analog (preferably human insulin or an analog of human insulin) may be used as the target gene to treat type I diabetes, type II diabetes, or metabolic syndrome; human growth hormone may be used as the target gene to treat children with growth disorders or growth hormone-deficient adults; erythropoietin (preferably human erythropoietin) may be used as the target gene to treat anemia due to chronic kidney disease, anemia due to myelodysplasia, or anemia due to cancer chemotherapy.

The present invention may be especially suitable for treating diseases caused by single gene defects such as cystic fibrosis, hemophilia, muscular dystrophy, thalassemia, or sickle cell anemia. Thus, human $\beta$-, $\gamma$-, $\delta$-, or $\zeta$-globin may be used as the target gene to treat $\beta$-thalassemia or sickle cell anemia; human Factor VIII or Factor IX may be used as the target gene to treat hemophilia A or hemophilia B.

The ligands used in the present invention are generally combined with one or more pharmaceutically acceptable carriers to form pharmaceutical compositions suitable for administration to a patient. Pharmaceutically acceptable carriers include solvents, binders, diluents, disintegrants, lubricants, dispersion media, coatings, antibacterial and antifungal agents, isotonic and absorption delaying agents, and the like, generally used in the pharmaceutical arts. Pharmaceutical compositions may be in the form of tablets, pills, capsules, troches, and the like, and are formulated to be compatible with their intended route of administration. Examples of routes of administration include parenteral, e.g., intravenous, intradermal, intranasal, subcutaneous, oral, inhalation, transdermal (topical), transmucosal, and rectal.

The pharmaceutical compositions comprising ligands are administered to a patient in a dosing schedule such that an amount of ligand sufficient to desirably regulate the target gene is delivered to the patient. When the ligand is a small molecule and the dosage form is a tablet, pill, or the like, preferably the pharmaceutical composition comprises from 0.1 mg to 10 g of ligand; from 0.5 mg to 5 g of ligand; from 1 mg to 1 g of ligand; from 2 mg to 750 mg of ligand; from 5 mg to 500 mg of ligand; or from 10 mg to 250 mg of ligand.

The pharmaceutical compositions may be dosed once per day or multiple times per day (e.g., 2, 3, 4, 5, or more times per day). Alternatively, pharmaceutical compositions may be dosed less often than once per day, e.g., once every 2, 3, 4, 5, 6, 7, 8, 9, 10, 11, 12, 13, or 14 days, or once a month or once every few months. In some embodiments of the invention, the pharmaceutical compositions may be administered to a patient only a small number of times, e.g., once, twice, three times, etc.

The present invention provides a method of treating a patient in need of increased expression of a therapeutic protein encoded by a target gene, the method comprising administering to the patient a pharmaceutical composition comprising a ligand for an aptamer, where the patient previously had been administered a recombinant DNA comprising the target gene, where the target gene contains a gene regulation cassette of the present invention that provides the ability to regulate expression of the target gene by the ligand of the aptamer by alternative splicing of pre-mRNA of the target gene, thereby increasing expression of the therapeutic protein.

Articles of Manufacture and Kits

Also provided are kits or articles of manufacture for use in the methods described herein. In aspects, the kits comprise the compositions described herein (e.g., for compositions for delivery of a vector comprising the target gene containing the gene regulation cassette) in suitable packaging. Suitable packaging for compositions (such as ocular compositions for injection) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present invention also provides kits comprising compositions described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing the administration, including e.g., any methods described herein. For example, in some embodiments, the kit comprises rAAV for expression of the target gene comprising the gene regulation cassette of the present invention, a pharmaceutically acceptable carrier suitable for injection, and one or more of: a buffer, a diluent, a filter, a needle, a syringe, and a package insert with instructions for performing the injections. In some embodiments the kit is suitable for intraocular injection, intramuscular injection, intravenous injection and the like.

"Homology" and "homologous" as used herein refer to the percent of identity between two polynucleotide sequences or between two polypeptide sequences. The correspondence between one sequence to another can be determined by techniques known in the art. For example, homology can be determined by a direct comparison of two polypeptide molecules by aligning the sequence information and using readily available computer programs. Alternatively, homology can be determined by hybridization of polynucleotides under conditions which form stable duplexes between homologous regions, followed by digestion with single-stranded-specific nuclease(s), and size determination of the digested fragments. Two polynucleotide or two polypeptide sequences are "substantially homologous" to each other when, after optimally aligned with appropriate insertions or deletions, at least about 80%, at least about 85%, at least about 90%, and at least about 95% of the nucleotides or amino acids, respectively, match over a defined length of the molecules, as determined using the methods above.

"Percent sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity. Alignment for purposes of determining percent amino acid or nucleic acid sequence identity can be achieved in ways known to the ordinarily-skilled artisan, for example, using publicly available computer software programs including BLAST, BLAST-2, ALIGN or Megalign (DNASTAR) software.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases.

"Heterologous" or "exogenous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector is a heterologous nucleotide sequence with respect to the vector.

It is to be understood and expected that variations in the principles of invention herein disclosed can be made by one skilled in the art and it is intended that such modifications are to be included within the scope of the present invention. The following Examples further illustrate the invention, but should not be construed to limit the scope of the invention in any way. All references cited herein are hereby incorporated by reference in their entirety.

EXAMPLES

Example 1. Effects of Splice Site Strength on the Expression of Regulated Genes

Experimental Procedures

Plasmid constructs: Luci-BsaI-acceptor: A DNA fragment containing a CMV promoter was released from pHAGE-CMV-eGFP-W (Harvard University) vector by restriction enzymes SpeI and NotI, and this fragment was cloned into pHDM-G (Harvard University) vector digested with SpeI and NotI. A fragment containing SV40 Ori sequence in the resulting vector was deleted by digesting with BsmI and BstXI, removing the 3' overhang and ligating. The subsequent vector was subjected to site directed mutagenesis (Agilent) to delete the BsaI site in the AmpR gene. The resulting vector was then digested with NotI and BamHI, and ligated with a fragment containing NotI-BsaI-BamHI sites to generate the final Luci-BsaI-acceptor vector.

pHDM-G was used as template for the human beta-globin intron 2 ("IVS2Δ") containing a deletion of the middle portion considered non-crucial to splicing (see Table 5, SEQ ID NO:1). pGL3-promoter (Promega) was used as template for the firefly luciferase gene. Construct 8: Luciferase gene was amplified by PCR using primers Luc-For-BsaI and Luci-Rev-BsaI. The PCR products were digested with BsaI and cloned into BsaI-digested Luci-BsaI-acceptor vector. Splicing Constructs 1-7 (Con 1-7, SEQ ID NOS. 1-7) expressing the luciferase gene inserted with intron IVS2Δ that has different 5'ss and 3'ss at each end of the intron sequence were made by ligating 3 BsaI-digested PCR products into BsaI-digested Luci-BsaI-acceptor. pGL3-promoter vector was used as Luciferase template, and pHDM-G was used as template for IVS2Δ. Primer pairs used to amplify PCR fragments for Con 1-7 are as follows: Con 1: Luci-For-BsaI/Luci-Splice-Rev_1, IVS2-BsaI-For/IVS2-BsaI-Rev_1 and Luci-Splice-For_1/Luci-Rev-BsaI; Con 2: Luci-For-BsaI/Luci-Splice-Rev_2, IVS2-BsaI-For/IVS2-BsaI-Rev_2, and Luci-Splice-For 2/Luci-Rev-BsaI; Con 3: Luci-For-BsaI/Luci-Splice-Rev_3, IVS2-BsaI-For/IVS2-BsaI-Rev_3, and Luci-Splice-For_3/Luci-Rev-BsaI; Con 4: Luci-For-BsaI/Luci-Splice-Rev_4, IVS2-BsaI-For/IVS2-BsaI-Rev_1, and Luci-Splice-For_4/Luci-Rev-BsaI; Con 5: Luci-For-BsaI/Luci-Splice-Rev_1, IVS2-BsaI-For/IVS2-BsaI-Rev_1 and Luci-Splice-For_5/Luci-Rev-BsaI; Con 6: Luci-For-BsaI/Luci-Splice-Rev_1, IVS2-BsaI-For/IVS2-BsaI-Rev 1 and Luci-Splice-For61/Luci-Rev-BsaI; Con 7: Luci-For-BsaI/Luci-Splice-Rev_1, IVS2-BsaI-For/IVS2-BsaI-Rev_1 and Luci-Splice-For71/Luci-Rev-BsaI. All constructs were verified by DNA sequencing.

TABLE 1

Splice sites of the splicing constructs (Con 1-7). The intron/exon boundaries are marked by ‖.

| Construct | 5' splice site | 3' splice site |
|---|---|---|
| Con 1 | AGG‖GTGAGT | TCTTATCTTCCTCCCACAG‖C (SEQ ID NO: 110) |
| Con 2 | AAA‖GTAAGC | TCTTATCTTCCTCCCACAG‖C (SEQ ID NO: 111) |
| Con 3 | GCA‖GTAAGT | TCTTATCTTCCTCCCACAG‖C (SEQ ID NO: 112) |
| Con 4 | GAG‖GTGTGG | TCTTATCTTCCTCCCACAG‖C (SEQ ID NO: 113) |
| Con 5 | AGG‖GTGAGT | CTTTACTTCTATGACTGTAG‖C (SEQ ID NO: 114) |
| Con 6 | AGG‖GTGAGT | GTGACTGTGTGTATGCACAG‖C (SEQ ID NO: 115) |
| Con 7 | AGG‖GTGAGT | ATTGTGATCGCAGCCAATAG‖C (SEQ ID NO: 116) |

Transfection: 3.5×10^4 HEK 293 cells were plated in 96-well flat bottom plate the day before transfection. Plasmid DNA (500 ng) was added to a tube or a 96-well U-bottom plate. Separately, TransIT-293 reagent (Mirus; 1.4 uL) was added to 50 μL Opti-mem I media (Life Technologies), and allowed to sit for 5 minutes at room temperature (RT). Then, 50 μL of this diluted transfection reagent was added to the DNA, mixed, and incubated at room temperature ("RT") for 20 min. Finally, 7 μL of this solution was added to a well of cells in the 96-well plate.

Firefly luciferase assay of cultured cells: 24 hours after media change, plates were removed from the incubator, and equilibrated to RT for several minutes on a lab bench, then aspirated. Glo-lysis buffer (Promega, 100 μL, RT) was added, and the plates allowed to remain at RT for at least 5 minutes. Then, the well contents were mixed by 50 μL trituration, and 20 μL of each sample was mixed with 20 μL of bright-glo reagent (Promega) that had been diluted to 10% in glo-lysis buffer. 96 wells were spaced on an opaque white 384-well plate. Following a 5 min incubation at RT, luminescence was measured using Tecan machine with 500 mSec read time. The luciferase activity was expressed as mean relative light unit (RLU)±S.D.

Results

Figure 1A:
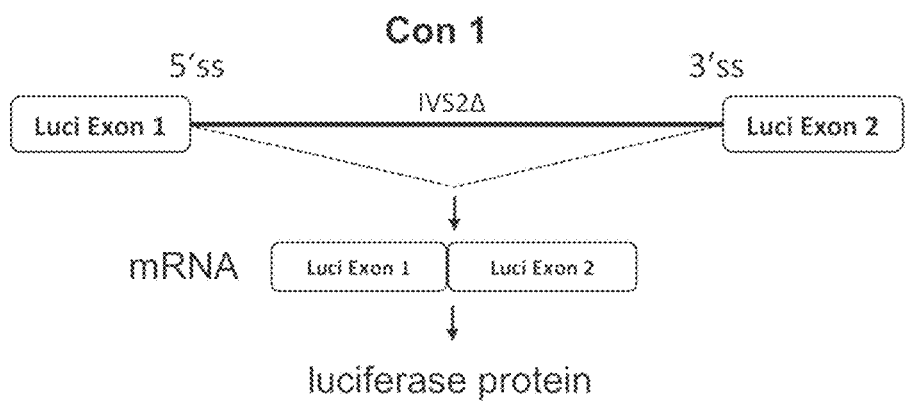
FIG. 1a. Schematic view of the splicing construct "Con 1" with the truncated human beta-globin intron 2 (IVS2Δ) inserted in the coding sequence of the luciferase gene. The designations "Luci Exon 1" and "Luci Exon 2" refer to the division of the luciferase gene into 5' and 3' coding sequences. Splicing of the inserted intron sequence IVS2Δ results in full length mRNA which is translated into full-length protein.
Figure 1B:
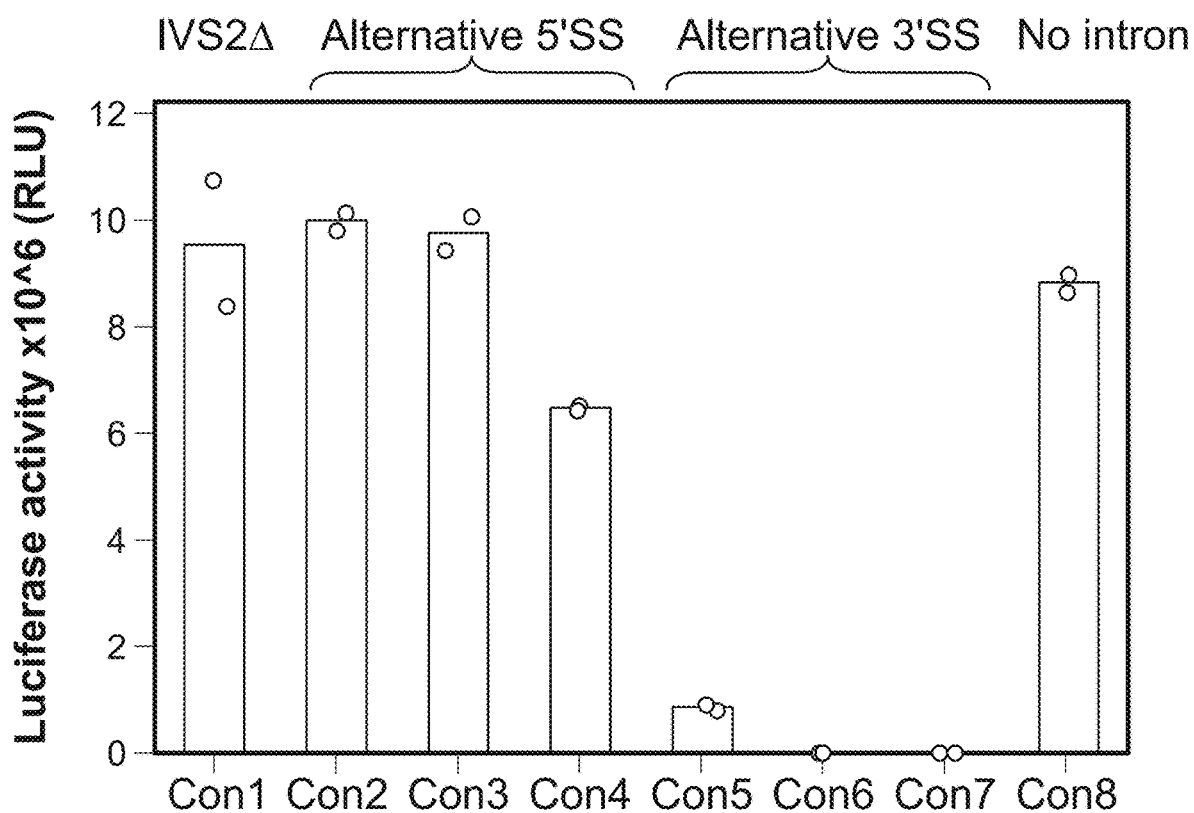
FIG. 1b. The effect of intron insertion and splice site sequence on luciferase expression. Con 1 through Con 7 have different intronic splice sites (see Table 1). Con 1 has IVS2Δ with its original IVS2 5' splice site and 3' splice site ("5'ss" and "3'ss" respectively). Con 2 to Con 7 have IVS2Δ inserted but with 5'ss and 3'ss sequence differences as listed in Table 1. Con 8 has no IVS2Δ intron. Con1 through Con 3 demonstrated no effects with intron insertion on luciferase expression compared to a luciferase control with no intron inserted (Con 8). Con 4 to Con 7, with weaker splice sites, displayed reduced luciferase expression.

In order to build a splicing-based gene regulation platform, we first tested (i) the effect of inserting an intron into the coding sequence (CDS) of a gene of interest, in this case the firefly luciferase gene (FIG. 1a), and (ii) the effects of different 5' ss and 3' ss on gene expression. The truncated human beta-globin intron 2 (IVS2Δ) with different 5' ss and 3' ss at each end was inserted in the coding sequence of the firefly luciferase gene to test efficiency of splicing. Construct Con 8 has no IVS2Δ intron, and Con 1 (SEQ ID No.: 1) has IVS2Δ with its original IVS2 5' and 3' ss sequences. Constructs Con 2 to Con 7 (SEQ ID No.: 2-7) have IVS2Δ with different 5' and 3' ss sequences as listed in Table 1. As shown in FIG. 1b, insertion of IVS2Δ with native IVS2 splice sites into the luciferase gene did not affect gene expression (compare Con 1 vs Con 8). However, replacement of IVS2 splice sites in IVS2Δ with splice site sequences having different strength significantly impaired luciferase expression. As shown in FIG. 1b, Con 2 and Con 3 with altered 5' ss have expression levels similar to Con 1 and Con 8, however the 5'ss changes in Con 4, and 3' ss changes in Con 5 through Con 7, did significantly reduce luciferase expression (compare Con 4 to Con 7 with Con 8). Therefore, differences in splice sites affect target gene expression. Con 1 was used for further development.

Example 2. An Intron-Exon-Intron Cassette and the Effect of Cis-Elements on Splicing in Modulating Target Gene Expression Experimental Procedures Putative exon splice enhancer (ESE) sequences were predicted using ESEfinder 3.0. The wild type human dihydrofolate reductase (DHFR) exon 2 with intronic flanking sequences, either with native 5'ss (DHFR-wt; (Table 2); SEQ ID NO.: 47), native 5'ss with four nucleotides mutated to C (DHFR-wt5ssC; (Table 2); SEQ ID NO.: 48), 5'ss sequences from Con 1 (DHFR-Con 15ss; Table 2 SEQ ID NO.: 49) or Con4 (DHFR-Con45ss, SEQ ID NO.: 50) were synthesized (IDT). To test the effect of ESE and exon splice suppressor (ESS) sequences within the DHFR exon 2, different DHFR exon 2 mutants were synthesized (listed in Table 2).

All of these different DHFR exon 2 sequences were cloned into the approximate center of the IVS2Δ intron in the Con 1 construct using the Golden Gate cloning strategy (NEB).

The constructs were verified by DNA sequencing (Genewiz). DNA was transfected in HEK 293 cells and assayed for luciferase activity as described in Example 1.

TABLE 2

DHFR exon 2 containing modified splice regulatory sequences. The underlined sequence indicates the modified splicing regulatory sequences within the DHFR exon 2.

| | | |
|---|---|---|
| DHFR-wt | GAATGAATTCAGATATTTCCAGAGA ATGACCACAACCTCTTCAGTAGAAG | SEQ ID NO: 117 |
| mtSRp40 | GAATGAATTCAGATATTTCCAGAGA ATGA<u>AAAAAAAAA</u>TCTTCAGTAGAAG | SEQ ID NO: 118 |
| StrSC35 | GAAT<u>GGCCCCT</u>GATATTTCCAGAGA ATGAC<u>C</u>ACAACCTCTTCAGTAGAAG | SEQ ID NO: 119 |
| SC35hnRNPA1 | GAATG<u>T</u>AGGGAGATATTTCCAGAGA ATGAC<u>C</u>ACAACCTCTTCAGTAGAAG | SEQ ID NO: 120 |

Results

Figure 2A:
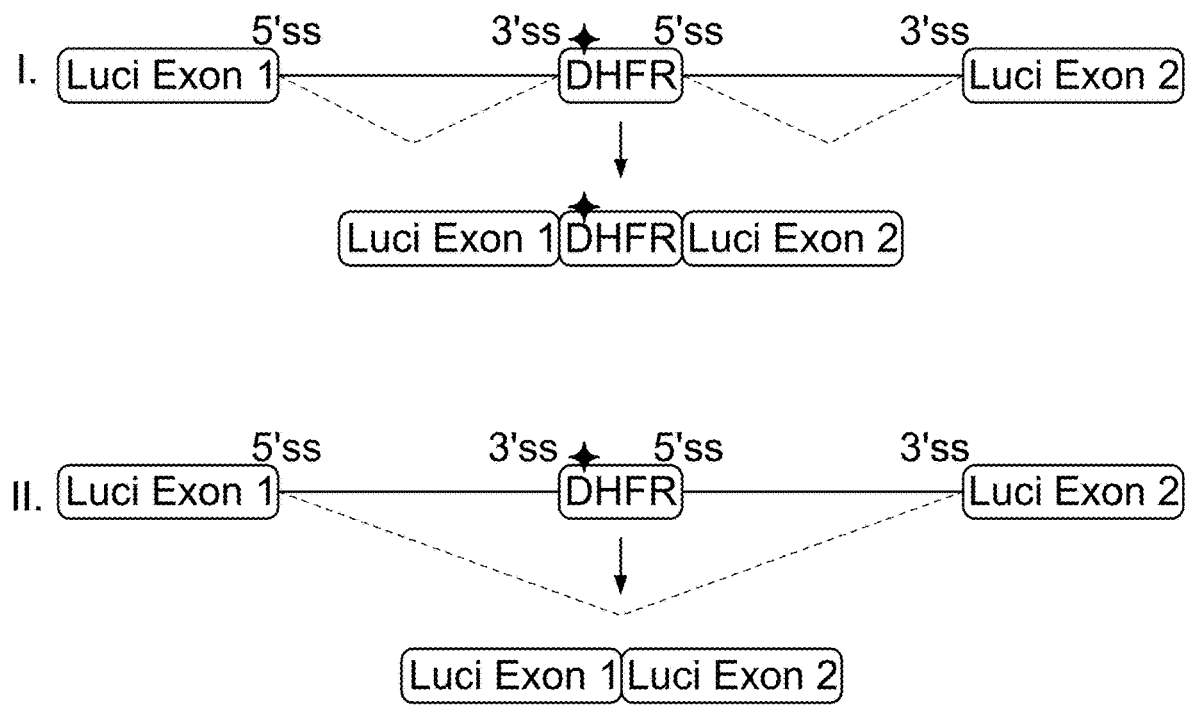
FIG. 2a. Schematic diagram of the Intron-Exon-Intron cassette with exon inclusion (I) and exclusion (II) splicing patterns depicted. The star (♦) denotes a stop codon in DHFR exon 2. When the alternative DHFR exon is included in the target gene (luciferase) mRNA by splicing (I), the resulting transcript contains an in-frame stop codon, which blocks luciferase gene expression. Only when the alternative DHFR exon containing the stop codon is excluded from the final mRNA is the target gene expressed (II).

The wild type human DHFR exon 2 and adjacent intronic sequences (SEQ ID NO.: 8) was inserted into the approximate center of the IVS2Δ intron in the Con 1 construct. This configuration generates a platform in which an exogenous exon in the intron sequence of a target gene can serve as an alternative exon allowing the expression of the target gene to be regulated through modulating alternative exon splicing. In this configuration (FIG. 2a), splicing events presumably occur between the 5' portion of the target gene and the DHFR exon, as well as between the DHFR exon and the 3' portion of target gene, resulting in inclusion of the DHFR exon into the target gene mRNA. As the alternative DHFR exon contains an in-frame premature stop codon when the DHFR exon is included in the mRNA, thereby reducing luciferase gene expression. However, when the 5' ss of the alternative DHFR exon (i.e., the splice donor site at the 5' end of the 3' intron) is mutated or inaccessible preventing splicing at this site, the DHFR exon is excluded from the mRNA, and the mRNA is efficiently translated and the target gene protein is expressed (FIG. 2a).

Figure 2B:
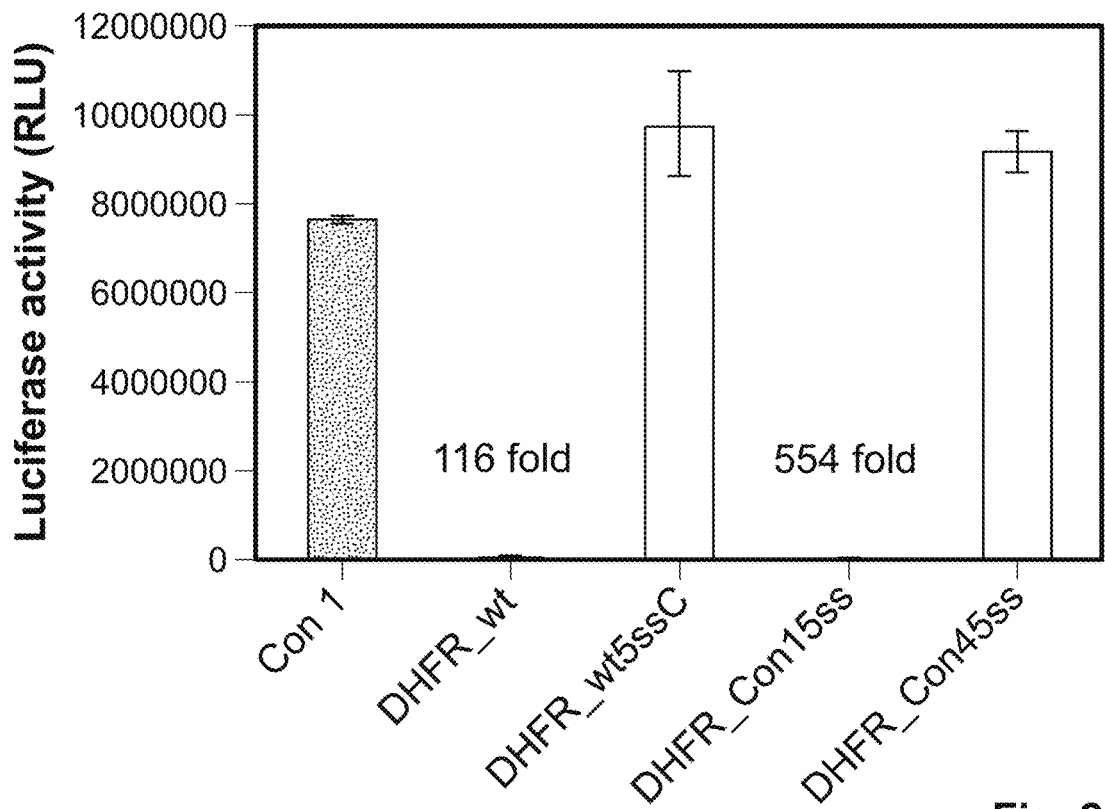
FIG. 2b. The effect of inclusion or exclusion of the DHFR alternative exon on expression of the luciferase gene. A luciferase assay was performed on HEK 293 cells transfected with different luciferase reporter constructs containing an Intron-Exon-Intron cassette as shown in FIG. 2a. The DHFR exon 2 with wild-type splice sites sequences (DHFR_wt) was compared to the DHFR exon containing mutations in the 5' ss (DHFR_wt5ssC) or with the native 5' ss replaced with the stronger Con 1 5'ss (DHFR_Con15ss), or with the weak 5'ss from Con 4 (DHFR_Con45ss). The construct used in lane 1 in 2b and 2c is Con 1, which is shown in FIG. 1 and Example 1. Insertion of DHFR exon 2 into the luciferase mRNA caused a decrease in luciferase expression, which did not occur when the 5'ss (i.e., the splice donor) of DHFR exon 2 was mutated (compare DHFR_wt to DHFR_wt5ssC). When the 5'ss of the DHFR exon was replaced with the stronger 5' ss from Con 1 (construct DHFR-Con1 5'ss) the inclusion of the DHFR exon was enhanced, leading to a 545-fold lower luciferase expression compared with Con 1. When a weak 5'ss (from Con 4 in Example 1) was used to replace the wild type 5'ss reduced splicing at this site prevented DHFR exon inclusion, thereby allowing increased luciferase expression.

We first tested the splicing of DHFR exon 2 with its native cis-elements unchanged, as well as various other versions in which the 5' ss sequences were either strengthened or weakened. Insertion of the DHFR exon with native 5'ss and 3'ss (SEQ ID NO.: 8) into the intronic sequence in Con 1 to create DHFR_wt, significantly decreased luciferase expression compared to Con1 which contains no alternative DHFR exon. Expression from the DHFR_wt construct is 116-fold lower than Con 1 (FIG. 2b).

When the 5' ss of the DHFR exon is mutated to a non-functional sequence (DHFR_wt5ssC; SEQ ID NO.: 48), DHFR exon inclusion is blocked and luciferase expression is restored to the level of Con 1 (FIG. 2aII, 2b, 2c)

When the 5' ss of the DHFR exon is replaced with the stronger 5' ss, in this case the 5'ss from Con 1 (DHFR_Con1 5ss; SEQ ID NO.: 49), the inclusion of the DHFR exon is increased, leading to a 545-fold decrease in luciferase gene expression compared with Con 1 (FIG. 2b). However, when the weak 5'ss from Con 4 was used (DHFR_Con4 5ss; SEQ ID NO.: 50), the DHFR exon is not included and luciferase expression is increased (FIG. 2b).

Figure 2C:
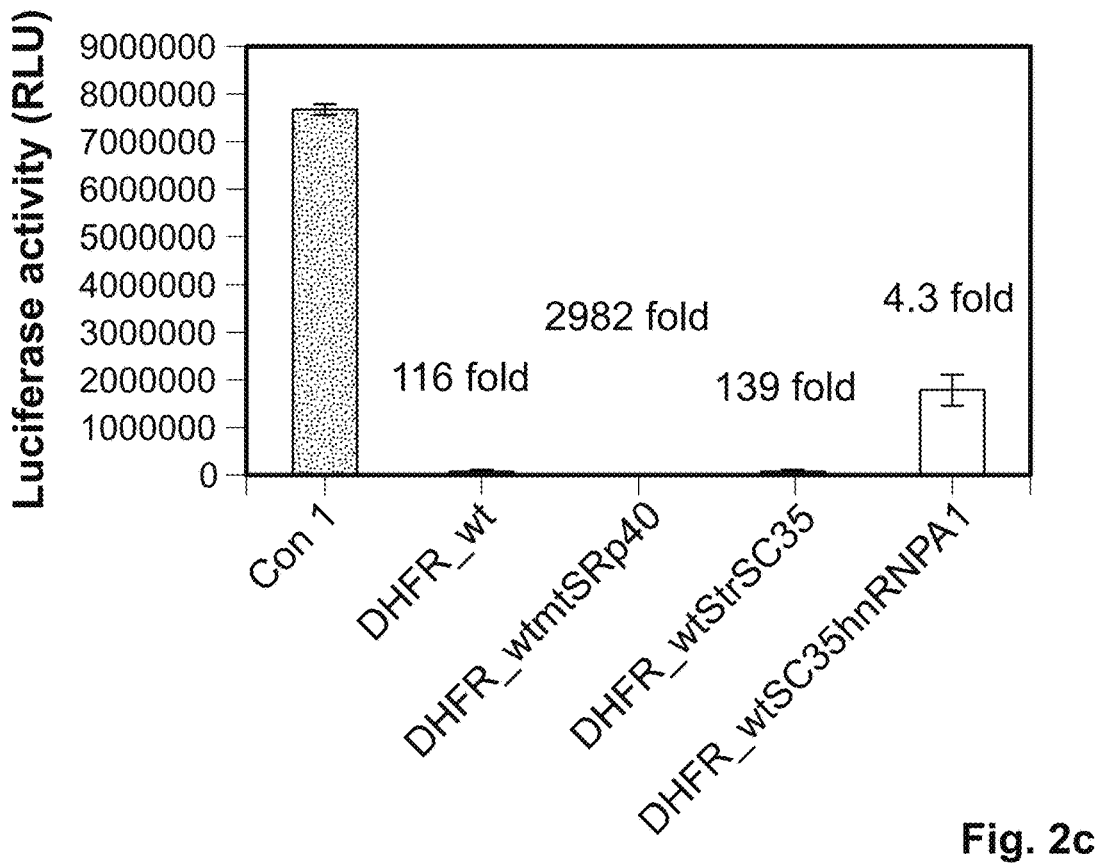
FIG. 2c. Exonic splicing enhancer (ESE) or suppressor (ESS) elements within the DHFR exon sequence influence splicing of the alternative DHRF exon and modulate expression of the target gene. Mutation of the SRp40 binding site within the DHFR exon 2 resulted in dramatic decrease in luciferase expression: 2,982-fold difference between DHFR_wtmtSRp40 expression and that of Con 1 (FIG. 2c DHFR_wtmtSRp40; Table 2). Mutation of a putative binding site for the splicing enhancer SC35, to generate a stronger SC35 binding site (Table 2, StrSC35), further decreased luciferase expression (139-fold) compared to Con 1 (FIG. 2c, DHFR_wtStrSC35), presumably due to increased efficiency of inclusion of the DHFR exon. Replacing the binding site for the splicing enhancer SC35 with that of the splicing inhibitor hnRNP A1 (Table 2, SC35hnRNPA1), led to a 4.3-fold increase in luciferase expression compared to the wild type DHFR exon 2 (FIG. 2c, DHFR_wt SC35hnRNPA1).

Exonic splicing enhancer (ESE) or suppressor (ESS) elements play crucial roles in splicing, and their functions often are context dependent. The effect of putative splicing regulatory sequences located within the DHFR exon were tested. When a putative splicing enhancer, the SRp40 binding site located within the DHFR exon was mutated (Table 2, DHFR_mtSRp40; SEQ ID NO.: 51), DHFR exon inclusion was dramatically enhanced, resulting in a 2982-fold decrease in luciferase expression compared to Con 1 (FIG. 2c, DHFR_wt and DHFR mtSRp40).

When another splicing enhancer, the SC35 binding site within the DHFR exon (predicted by ESE finder) was mutated to a stronger SC35 binding sequence (Table 2, DHFR_StrSC35; SEQ ID NO.: 52), DHFR exon inclusion was enhanced, decreasing luciferase expression by 139-fold compared to Con1 (FIG. 2c, DHFR_wtStrSC35). This is a slightly greater decrease than was seen with the construct containing the native DHFR exon (DHFR_wt FIG. 2b)

When the splicing enhancer, SC35 binding site was mutated to a splicing inhibitor (hnRNP A1 binding site) (Table 2, DHFR_wtSC35hnRNPA1; SEQ ID NO.: 53), the inclusion of the DHFR exon was less efficient leading to increased luciferase expression (FIG. 2c, DHFR_wt and DHFR_wtSC35hnRNPA1).

An Intron-Exon-Intron cassette has been created in which the expression of the target gene, in this case luciferase, can be switched on or off depending on the inclusion or exclusion of an alternative exon, in this case the alternative DHFR exon containing an in-frame stop codon. Splicing that results in inclusion of the alternative exon reduces gene expression, while gene expression increases when splicing excludes the alternative exon. The strength or weakness of the alternative exon 5' ss as well as sequences within the exon that modulate splicing alter the level of target expression via their impact on the inclusion or exclusion of the exogenous exon.

Example 3. The Effects of Hairpin Formation at the Alternative Exon 5' Splice Site on Regulating Target Gene Expression Experimental Procedures Sequences containing the DHFR exon 2 with native 3' and 5' ss sequences, in which the 5'ss was embedded in a hairpin structure were synthesized (IDT), and cloned into the indicated vector using Golden Gate cloning strategy (NEB). Constructs were transfected into HEK 293 cells and assayed for luciferase activity as described in Example 1.

Results

We tested whether embedding the 5' ss of the DHFR exon into a hairpin stem structure could affect splicing and inclusion of the alternative DHFR exon and thus alter target gene expression (illustrated in FIG. 3a).

Inclusion of alternative DHFR exon with Con1 5' splice site (DHFR_Con15ss; SEQ ID NO.: 49) sequences abolishes luciferase expression compared to Con 1 (FIG. 3c, DHFR_Con15ss). A 15 base pair (bp) hairpin structure embedding the entire sequence of the 5' ss was engineered into DHFR_Con 15ss to create DHFR_Con 15ss_HP15 (SEQ ID NO.: 54) (FIG. 3a). The presence of the 15 bp hairpin structure completely restores luciferase expression to the level of Con 1, indicating that the hairpin has abolished accessibility of the 5' ss and thereby abolished inclusion of the alternative DHFR exon. (FIG. 3c, Con 1, DHFR Con15ss and DHFR_Con15ss_HP15)

In contrast, a 15 bp hairpin with a "broken stem" (FIG. 3b, Con15ss_15HPx; SEQ ID NO.: 55) was not able to restore luciferase expression (FIG. 3c, DHFR_Con15ss_HP15x), indicating the intact stem is an important component of the RNA secondary structure in regulating the accessibility of 5' splice site and thereby determining the inclusion or exclusion of the alternative exon.

The same experiments were carried out using the construct containing the DHFR exon with mutant SRp40 binding site that has increased splicing efficiency (DHFR_wtmtSRp40, see Example 2). Embedding the 5' ss in a hairpin restored luciferase expression, whereas breaking the hairpin blocked luciferase expression (FIG. 3c, DHFR_wtmtSRp40, DHFR_wtmtSRp40_HP15 and DHFR_wtmtSRp40_HP15x)

Thus, embedding the 5'ss of an alternative exon in a hairpin structure can restore target gene expression by blocking accessibility of that 5' ss and, thereby preventing inclusion of the alternative exon into the mRNA, and allowing target gene protein expression. A gene expression platform was created in which target gene protein expression can be modulated by altering availability of the 5' ss of an exogenous alternative exon through secondary RNA structure.

The construct DHFR_wtmtSRp40 (SEQ ID NO.: 58) (referred to as "mtDHFR" below) was used for further riboswitch development.

Example 4. Use of a Theophylline Aptamer to Regulate Target Gene Expression Via Alternative Splicing Experimental Procedures A DHFR-acceptor vector was constructed to facilitate the cloning of an aptamer sequence attached to the hairpin stems with different length. The theophylline aptamer sequence used was: ggcgatacCAGCCGAAAGGCCCTTGgcagegtc (SEQ ID NO:9). Theophylline aptamer oligonucleotides ("oligos") with 4 nucleotide overhang at 5' end were synthesized (IDT), annealed and ligated to BsaI-digested DHFR-acceptor vector. HEK 293 cells were transfected with the luciferase reporter constructs with the regulation cassette containing the theophylline aptamer, as described in Example 1. Four hours after transfection, the media was aspirated, and new media with or without 3 mM theophylline was added, and luciferase was assayed 20 to 24 hours after theophylline treatment. The fold induction was expressed as the quotient of luciferase activity obtained in the presence of aptamer ligand divided by the value obtained in the absence of the aptamer ligand. The level of the luciferase activity was expressed as percent of level of luciferase activity (referred as maximal expression) produced by Con1 construct that does not IVS2Δ intron in the CDS of luciferase gene.

Results

In order to regulate the accessibility of the 5' splice site of the stop codon-containing alternative exon, and thereby regulate target gene protein expression, aptamer sequences were attached to the stem of a hairpin structure that embeds the intronic portion of the DHFR 5' ss and its complementary sequence In this configuration, insertion of aptamer sequences disrupts the formation of the hairpin stem, leaving DHFR 5' ss accessible, thus resulting in the inclusion of alternative DHFR exon and preventing target gene protein expression (FIG. 4*a*). When aptamer/ligand binding occurs, as depicted in FIG. 4*b*, conformational change in aptamer triggered by ligand binding brings together the DHFR 5' ss and its complementary sequence for stable stem formation, thus hiding the DHFR 5' ss and resulting in DHFR exon exclusion and target gene protein expression.

A theophylline aptamer was tested by linking the lower stem of theophylline aptamer directly to the hairpin stem (FIG. 4*c*, DHFR_Theo1). If the stem is too long, it may form a stable structure in the absence of aptamer/ligand binding, while if it is too short it may never form a stable stem, even when the ligand is present. Therefore the length of the stem needs to be optimized such that a stable secondary structure is only formed on aptamer/ligand binding. To determine the optimal stem length that allows stem formation in the presence but not absence of the ligand, a number of constructs were made in which the theophyline aptamer was cloned into mtDHFR (described in Example 2, Table 2) and serial truncations of the stem were carried out. FIG. 4*c* shows four constructs from this serial truncation.

FIG. 4*d* shows the expression of luciferase from this deletion series of constructs in the presence and absence of theophylline. In constructs Theo 1 through Theo 12 with stem lengths from 20 bp down to 9 bp, the stem length was sufficient to form a stable secondary structure even in the absence of aptamer/ligand binding. Thus luciferase expression is seen at levels similar to Con 1 in both the absence and the presence of thyophylline.

With construct DHFR_Theo13, luciferase expression is suppressed in the absence of theophylline. This indicates the availability of the mtDHFR exon 5'ss, leading to inclusion of the alternative DHFR exon and suppression of gene expression. However, in the presence of theophylline, luciferase expression was switched on, resulting in a 43-fold induction over the expression level without theophylline, and about 56% of the luciferase level expressed by the Con1 control vector. Therefore, a mammalian on-riboswitch was generated, which turns on target gene protein expression in the presence of the aptamer ligand, theophylline.

Example 5. Use of Xpt Guanine Aptamer to Regulate Target Gene Expression Via Alternative Splicing Experimental Procedures Xpt-guanine aptamer with the following sequence: cactcatataatCGCGTGGATATGGCACGCAAGTTTC-TACCGGGCACCGTAAATGTCcgact atgggtg (SEQ ID NO.: 10), was used to construct a riboswitch. Oligos containing the sequence of guanine aptamer and hairpin stem with 4 nucleotide 5' overhang were synthesized (IDT), annealed and then ligated to BsaI-digested DHFR-acceptor vector. HEK 293 cells were transfected as described in Example 1. Four hours after transfection, the media was aspirated, and new media with or without 500 μM guanine was added. Luciferase expression was assayed 20 to 24 hrs after guanine treatment as described in Example 1 and Example 4. HepG2, AML12, RD and C2C12 (ATCC) were cultured using the protocol recommended by ATCC. The intron-exon-intron cassette containing the xpt-G17 riboswitch (SEQ ID NO.: 15) was inserted in the leader peptide sequences of the anti-KDR antibody gene and into the StuI site in mouse erythropoietin gene using Gibson cloning strategy (NEB). Constructs containing mouse erythropoietin (Epo) or anti-KDR antibody were transfected into HEK 293 cells. Four hour after transfection, the media was aspirated, and new media with or without 500 µM guanine was added. Supernatants were subjected to ELISA assay for the production of either anti-KDR antibody or the production of mouse Epo (R&D Systems).

Results

Figure 5A:
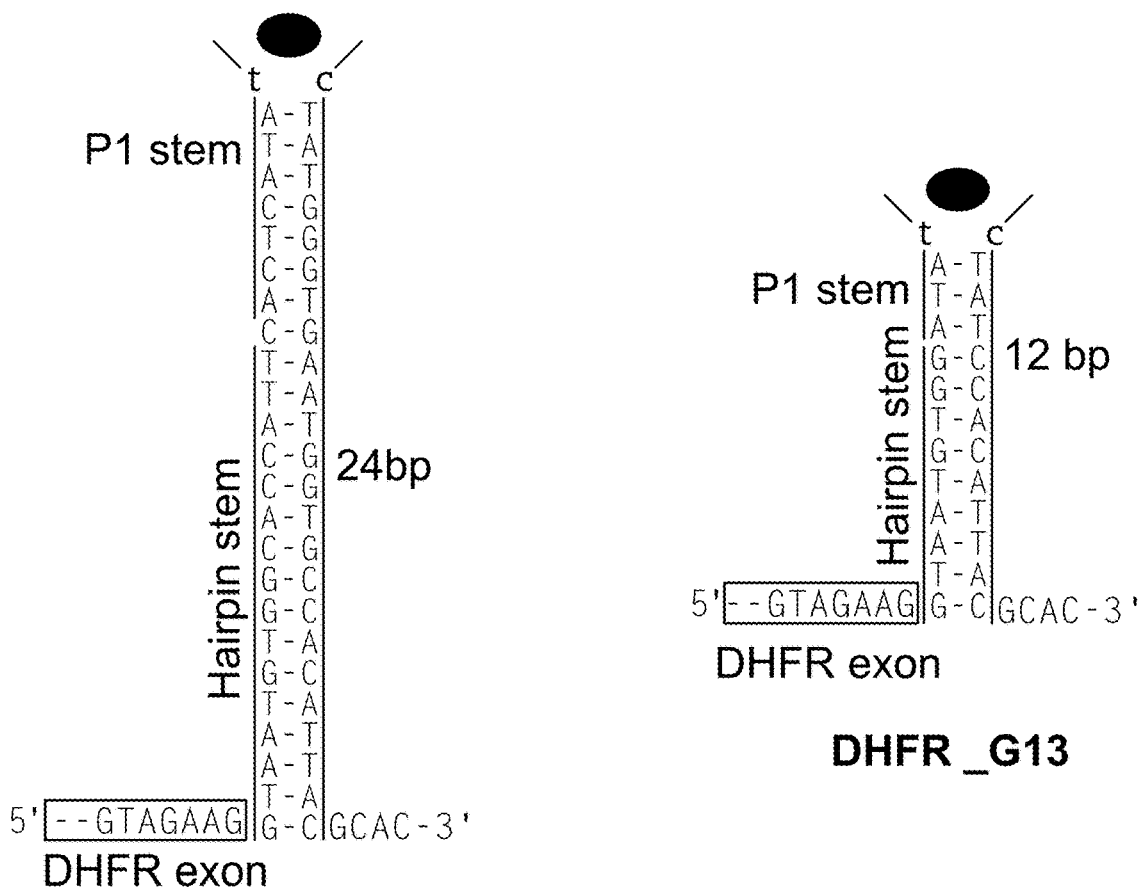
FIG. 5a. Sequences of synthetic stems connecting xpt-guanine aptamer and DHFR exon 5'ss sequence generated by serial truncation of the hairpin stem and the aptamer P1 stem. Guanine is symbolized as (•). DHFR_G1 (SEQ ID NO: 78 and SEQ ID NO:79); DHFR_G13 (SEQ ID NO:80 and SEQ ID NO:81); DHFR_G14 (SEQ ID NO:82 and SEQ ID NO: 83); DHFR_G15 (SEQ ID NO:84 and SEQ ID NO:85); DHFR_G16 (SEQ ID NO: 86 and SEQ ID NO:87); DHFR_G17 (SEQ ID NO:88 and SEQ ID NO:89); DHFR_G18 (SEQ ID NO:90 and SEQ ID NO:91).
Figure 5A:
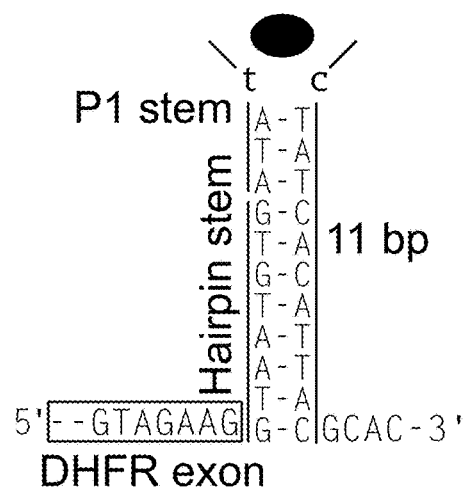
Figure 5A:
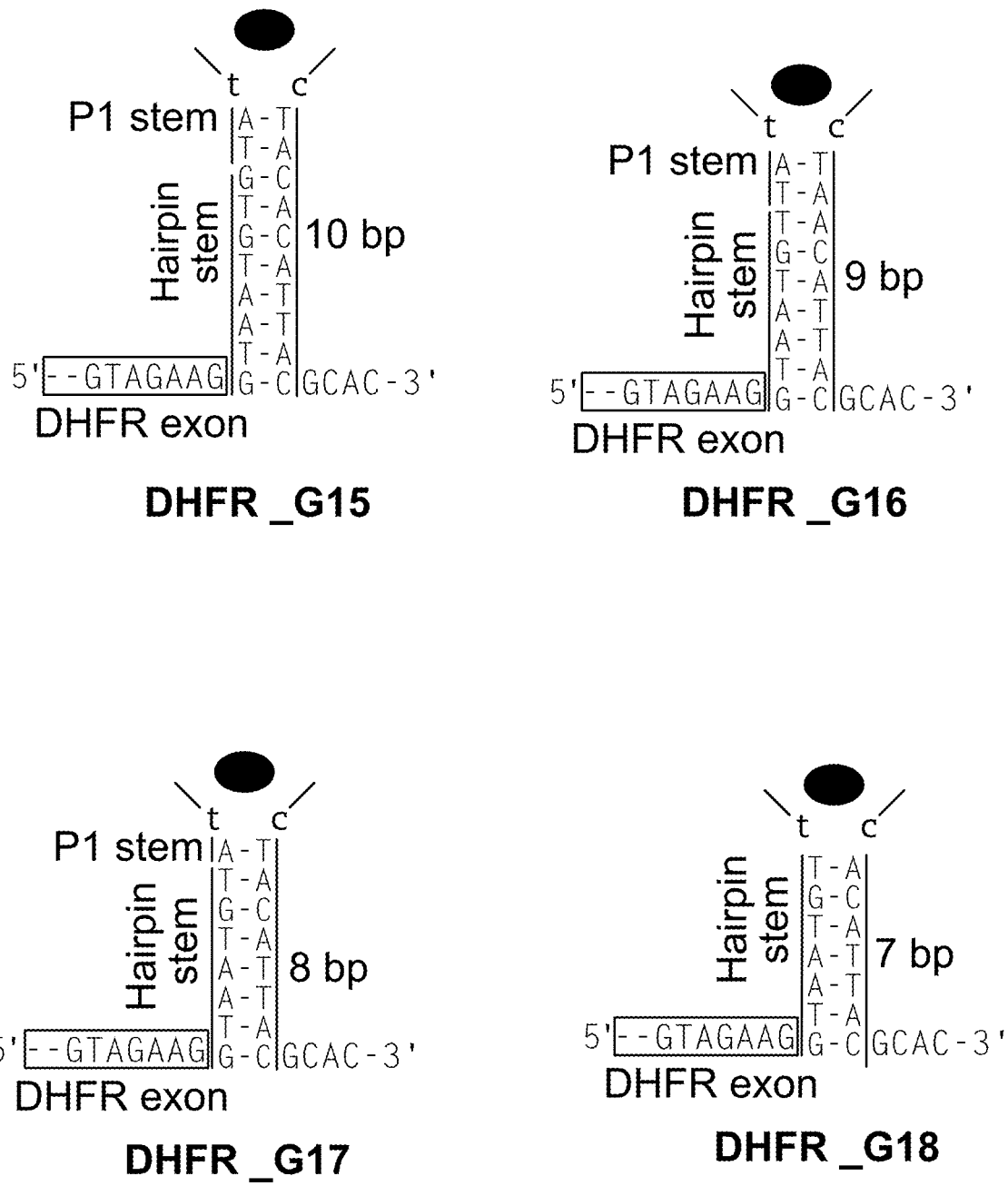
Figure 5B:
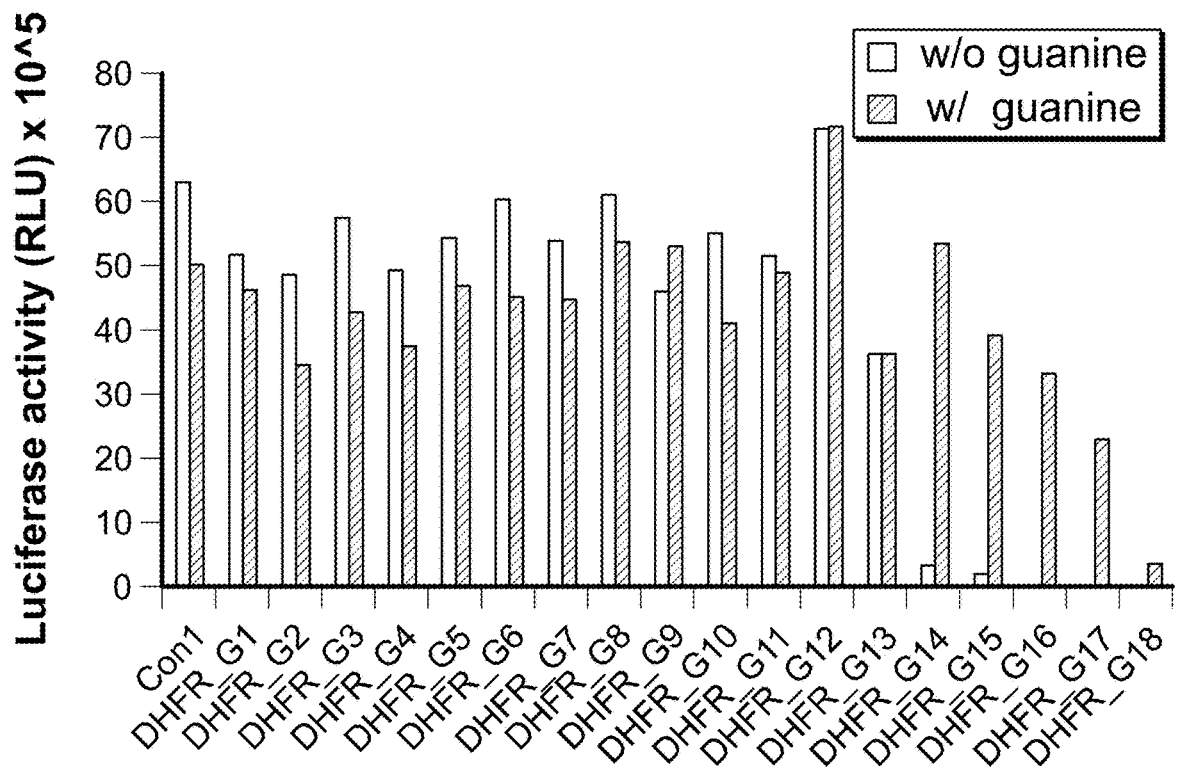
FIG. 5b. Effect of the stem length on the ability of a riboswitch to regulate luciferase expression in response to aptamer ligand binding. Eighteen riboswitches of different stem lengths were inserted into the regulatory cassette and the constructs were transfected into HEK 293 cells which were grown in the presence or absence of 500 μM guanine. In the absence of guanine, constructs G14 through G18 demonstrate reduced luciferase expression compared to the unregulated Con 1 control. In the presence guanine, luciferase expression was restored to varying extents.

The use of additional aptamer/ligands to control target gene expression by aptamer-mediated modulation of alternative splicing was studied by attaching an xpt-guanine aptamer, derived from *Bacillus subtilis*, through stem P1 to the hairpin stem (FIG. 5a, DHFR_G1). Similar to Example 4, 18 constructs were made by serial truncation of the connecting stem (FIGS. 5a and 5b; DHFR-G1 through G18, also referred to as xpt-G1 through G18 containing regulatory cassettes) to obtain the optimal length of hairpin stem in connection with the guanine aptamer, thus allowing the communication of aptamer/ligand binding to 5'ss accessibility and exon splicing. As shown in FIG. 5b, with constructs DHFR-G1 through G13, with stem lengths from 24 bp down to 12 bp, luciferase expression is not affected by the insertion of the alternative DHFR exon and xpt-guanine aptamer in the presence or absence of the aptamer ligand guanine. This suggests that the length of the stem is sufficient to form a stable structure in both the absence and the presence of the ligand, preventing inclusion of the alternative exon in the mRNA. However, in constructs DHFR_G14 through DHFR_G18, luciferase expression was suppressed in the absence of added guanine. When µM guanine was added, luciferase expression from these constructs was induced (FIG. 5b).

Figure 5C:
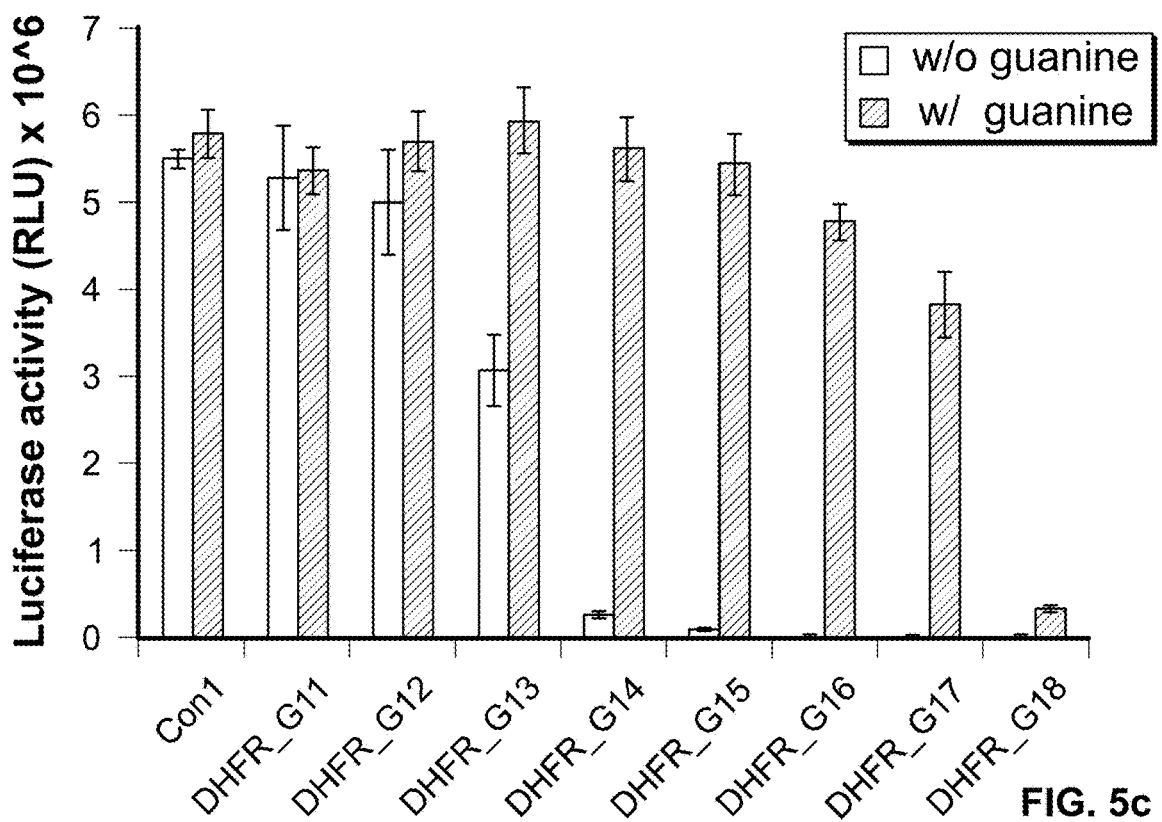
FIGS. 5c and 5d. Further analysis of effect of the stem length on ability of riboswitch to regulate luciferase expression in response to aptamer ligand binding. Construct G11 through G18 were validated using luciferase assay.
Figure 5D:
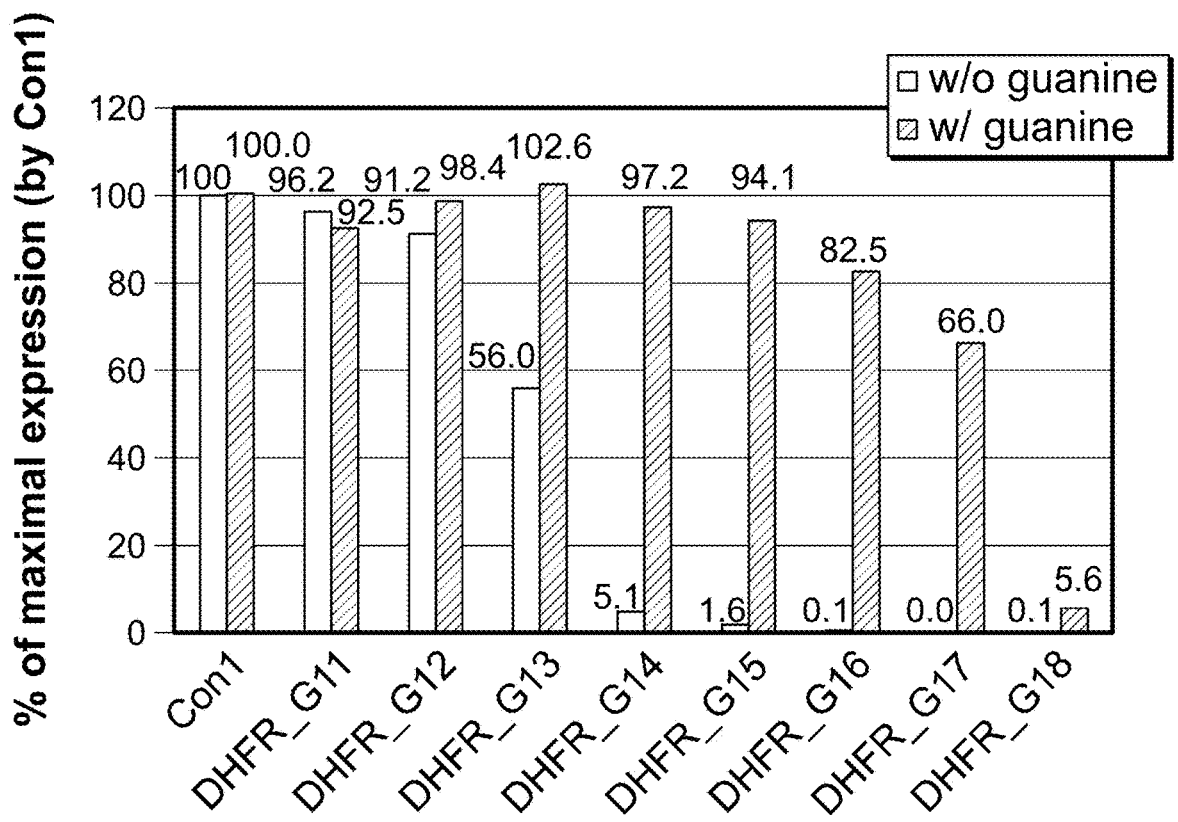

A further stringent validation of constructs G11 through G18 again showed clear regulation of luciferase expression upon guanine treatment (FIG. 5c). Construct DHFR_G17 containing xpt-G17 (SEQ ID NO.: 15) (FIG. 5a) gave 2000-fold induction of expression, resulting in about 65% of the level of luciferase expressed by Con1 (referred as maximal expression). This high dynamic range of induction resulted from activation of expression from a very low un-induced baseline level in the absence of the ligand. Construct DHFR_G16 (FIG. 5a) gave about 800-fold induction over un-induced baseline expression to a level that was 83% of maximal expression (FIGS. 5c and 5d). In addition, constructs DHFR G14 and G15 showed nearly 100% of maximal expression with a lower fold induction due to higher un-induced baseline expression of luciferase.

Figure 5E:
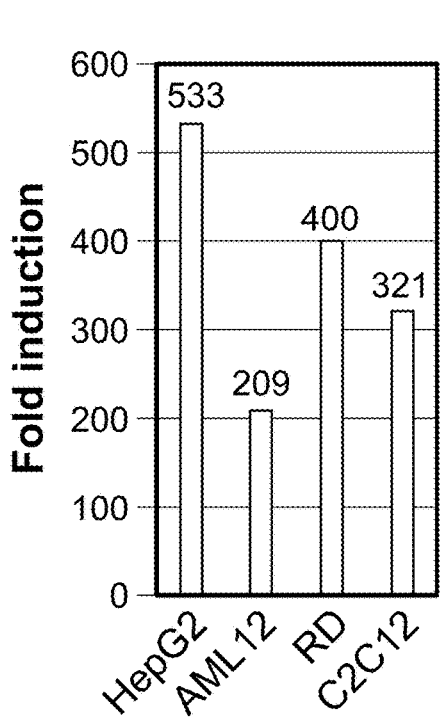
FIG. 5e. The regulatory cassette containing xpt-G17 riboswitch allowed regulation of gene expression in response to ligand in a number of different mammalian cell types. DHFR_G17 was transfected into HepG2, AML12, RD and C2C12 cell lines, and assayed for induced luciferase expression on treatment with guanine. The fold induction of luciferase expression when the cells were grown in the presence of ligand compared to the un-induced baseline level of expression when no guanine was added to the cell culture media is shown.
Figure 5F:
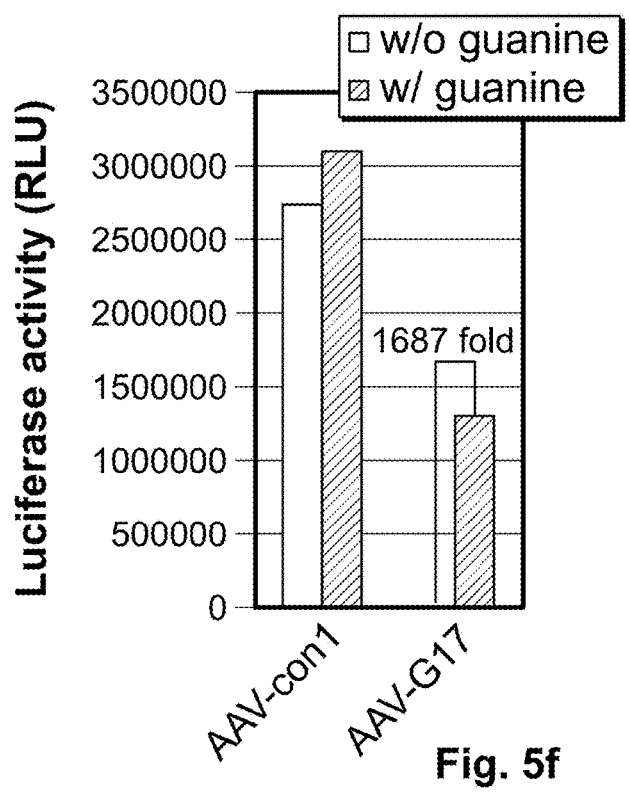
FIG. 5f. Regulation of luciferase by the xpt-G17 containing regulatory cassette in the context of a viral vector. A construct with the luciferase gene containing the xpt-G17 regulatory cassette was transferred to an AAV vector backbone and used to transfect cells. Cells were grown in the presence and absence of guanine. The fold induction of luciferase in the presence of the guanine is shown, 1687 fold induction of expression was seen on treatment with guanine.

To test the general functionality and applicability of the synthetic riboswitch in the Intron-Exon-Intron cassette, we transfected the xpt-G17 containing construct (DHFR_G17) into multiple human and mouse cell lines. In these different cell lines, guanine treatment generated significant induction of gene expression, more than 500-fold induction in HepG2 cells, with lower fold induction in other cell lines (FIG. 5e). The different fold induction in different cell lines may reflect differences in transfection efficiency as well as in the cell-type specific splicing regulator expression profile. Further, the luciferase gene with the regulatory cassette containing the xpt-G17 riboswitch (DHFR_G17) yielded similar level of induction when transferred to an AAV backbone (FIG. 5f), indicating that the gene regulating effect is not vector backbone dependent.

Figure 5G:
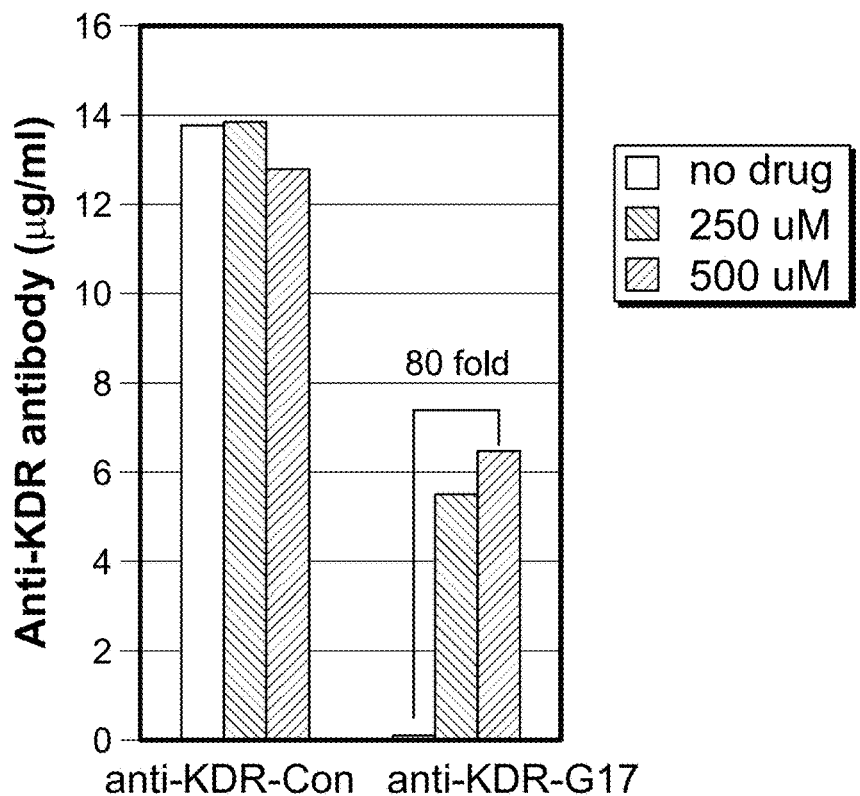
FIG. 5g. Regulation of antibody by the regulatory cassette in response to the aptamer binding ligand. The Intron-Exon-Intron regulatory cassette with the xpt-G17 riboswitch was inserted into the leader peptide sequence of the anti-KDR antibody sequence, and the resulting construct was transfected into HEK 293 cells. As assayed by ELISA, there was an 80-fold induction of antibody protein expression upon treatment of the transfected cells with ligand, compared to untreated cells. The induced level of expression reached about 40% of control construct containing the Con 1 intron sequences.
Figure 5H:
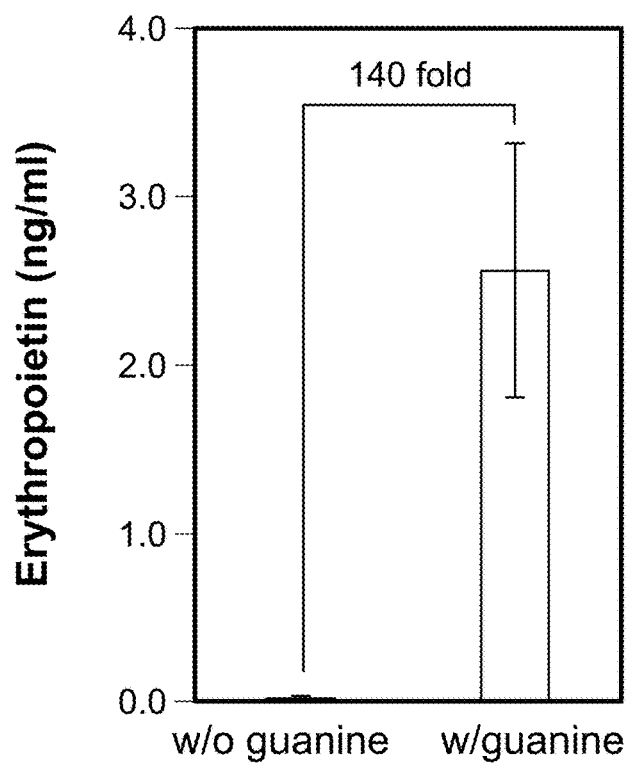
FIG. 5h. Regulation of secreted erythropoietin protein (EPO) by the regulatory cassette in response to the aptamer/ligand binding. The Intron-Exon-Intron regulatory cassette with the xpt-G17 riboswitch was inserted in the murine erythropoietin (Epo) gene and the resulting construct was transfected into HEK 293 cells. Low level expression of EPO was observed in the absence of guanine, as assayed by ELISA. In the presence of guanine, 140-fold induction of EPO expression was observed.

In addition to regulating the luciferase gene, the xpt-G17 containing regulatory cassette was also tested in regulating secreted proteins, anti-KDR antibody and erythropoietin (Epo). The xpt-G17 containing regulatory cassette was inserted into the coding sequence of anti-KDR antibody and of erythropoietin. As shown in FIGS. 5g and 5h, guanine treatment yielded 80-fold induction in anti-KDR antibody production and 140-fold induction in Epo production, when compared to the production of each molecule from cells in the absence of ligand.

These results demonstrate the general functionality and applicability in regulating protein expression of a potential therapeutic target gene, as well as the application of this gene regulation cassette in AAV-mediated gene delivery. Thus, we have created a synthetic mammalian "on"-riboswitch which is capable of switching on target gene protein expression in response to the presence of an aptamer specific ligand in mammalian cells.

Example 6. Different Purine Aptamers May be Used to Regulate Target Gene Expression Via Alternative Splicing Experimental Procedures The following aptamer sequences, listed in Table 3, were used to build riboswitches:

TABLE 3

| | |
|---|---|
| Ydh1-G<br>SEQ ID NO.: 11 | ttgtataacctcaat<br>aatatggtttgaggg<br>tgtctaccaggaacc<br>gtaaaatcctgacta<br>caa |
| Ydh1-A<br>SEQ ID NO.: 12 | ttgtataacctcaat<br>aatatggtttgaggg<br>tgtctaccaggaacc<br>gtaaaatcctgatta<br>caa |
| addA-G<br>SEQ ID NO.: 13 | tcatataatcctaat<br>gatatggtttgggag<br>tttctaccaagagcc<br>ttaaactcttgacta<br>tga |
| addA-A<br>SEQ ID NO.: 14 | tcatataatcctaat<br>gatatggtttgggag<br>tttctaccaagagcc<br>ttaaactcttgatta<br>tga |

Results

Figure 6A:
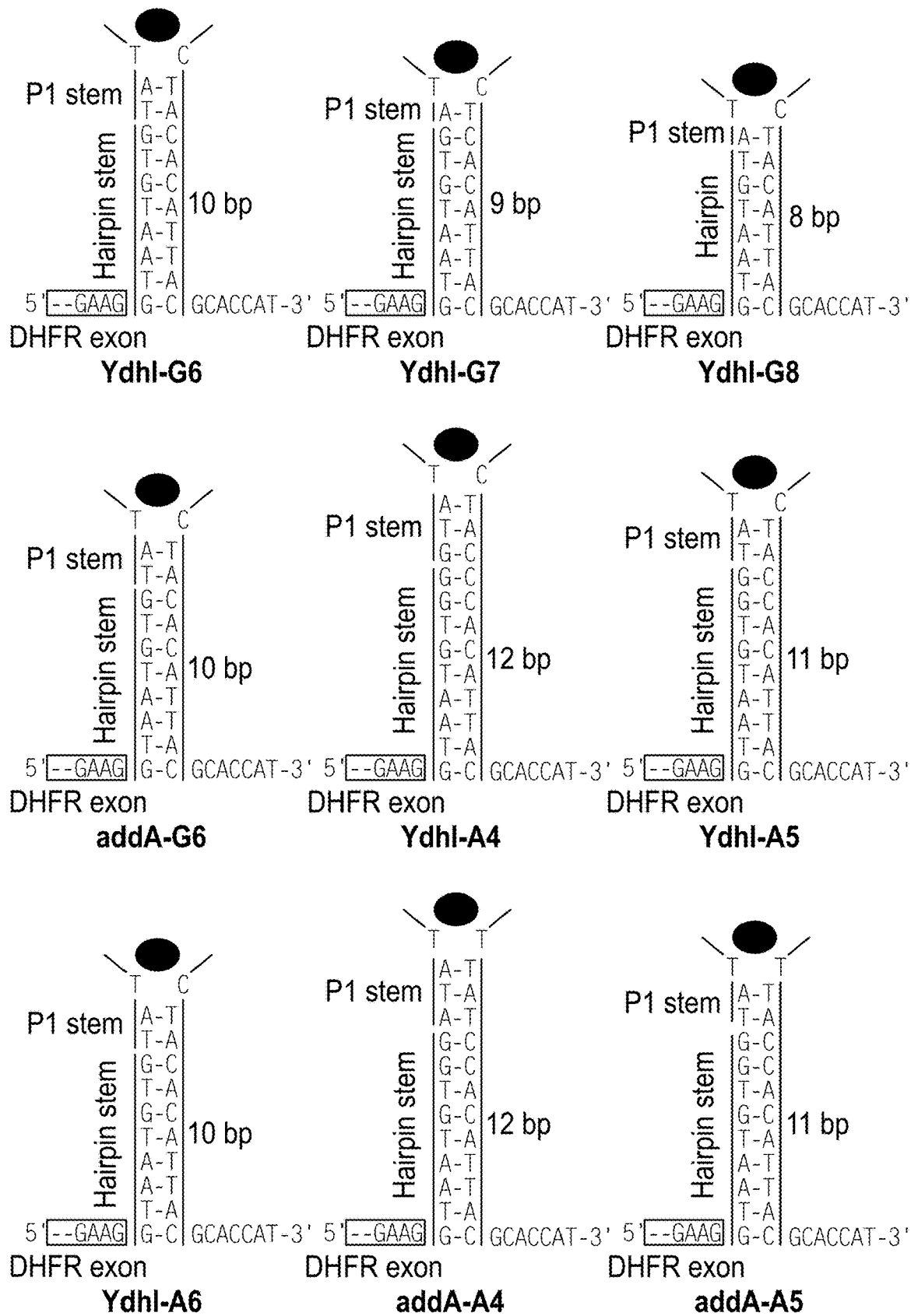
FIG. 6a Structures of the different purine riboswitch stems tested in the regulatory cassette. Purine is symbolized as •. Ydhl-G6 (SEQ ID NO:92 and SEQ ID NO: 93); Ydhl-G7 (SEQ ID NO:94 and SEQ ID NO:95); Ydhl-G8 (SEQ ID NO:96 and SEQ ID NO: 97); addA-G6 (SEQ ID NO:98 and SEQ ID NO:99); Ydhl-A4 (SEQ ID NO:100 and SEQ ID NO:101); Ydhl-A5 (SEQ ID NO:102 and SEQ ID NO:103); Ydhl-A6 (SEQ ID NO: 104 and SEQ ID NO:105); addA-A4 (SEQ ID NO:106 and SEQ ID NO:107); addA-A5 (SEQ ID NO:108 and SEQ ID NO:109).
Figure 6B:
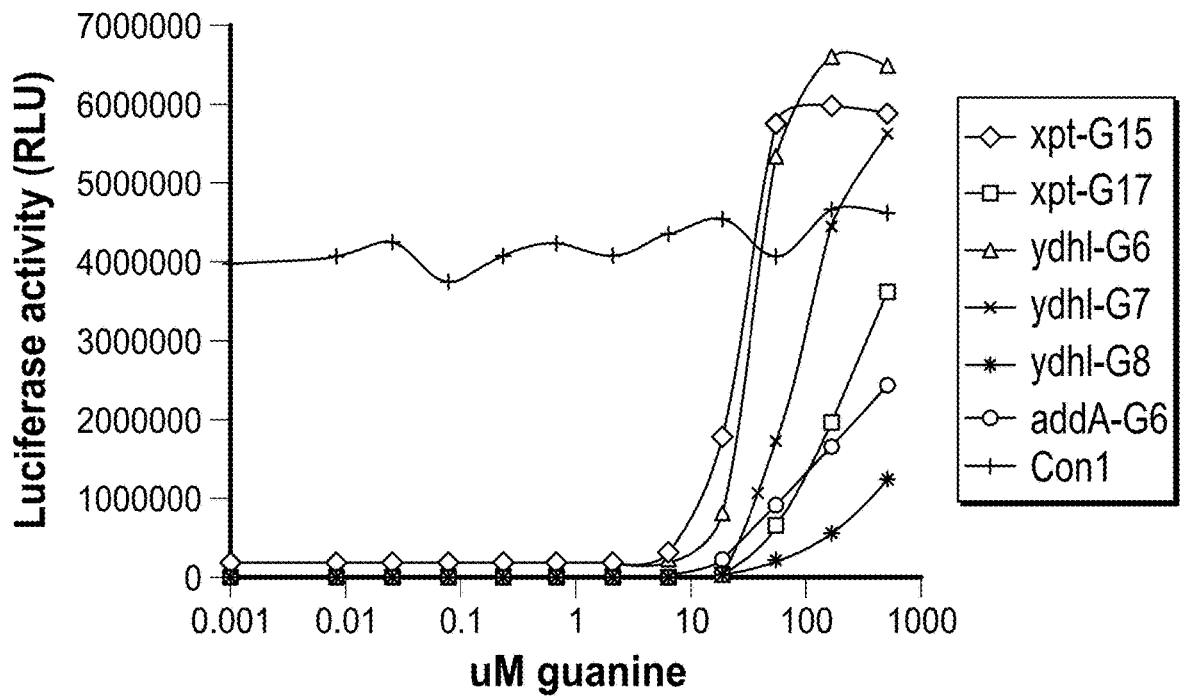
FIG. 6b-6e. Dose responses of constructs with regulatory cassettes containing different aptamer based riboswitches (the riboswitch stems illustrated in FIG. 6a).
Figure 6C:
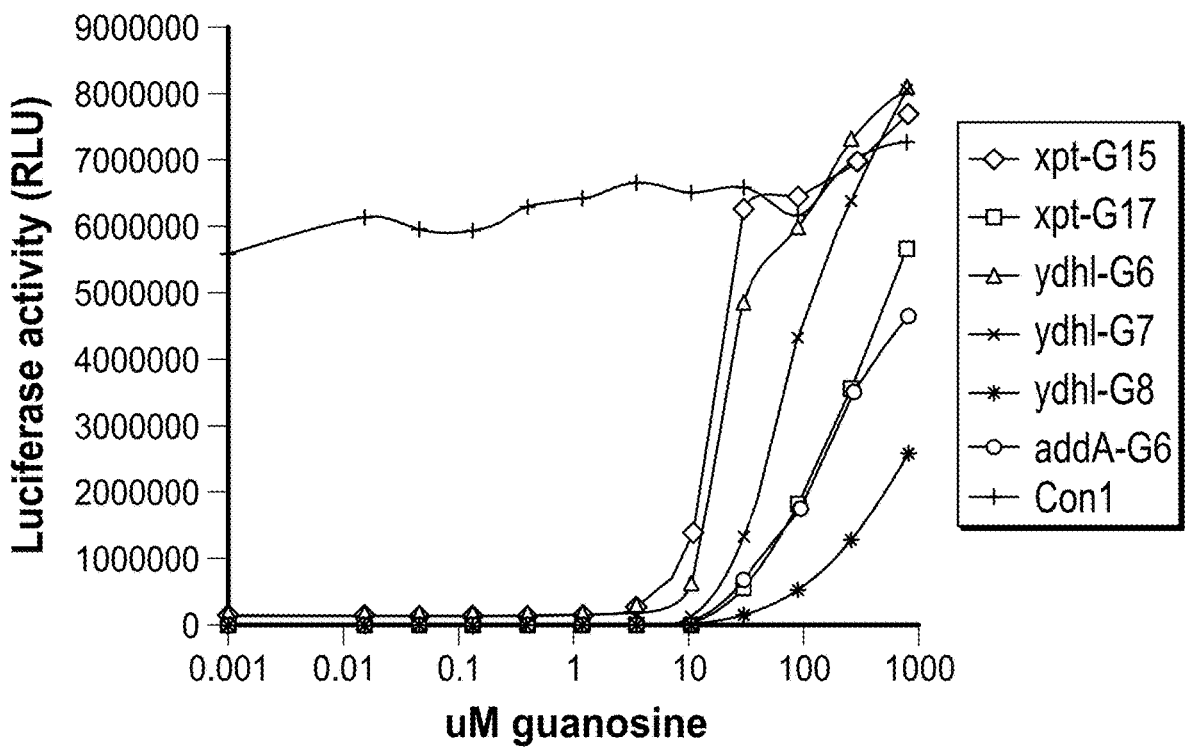
Figure 6D:
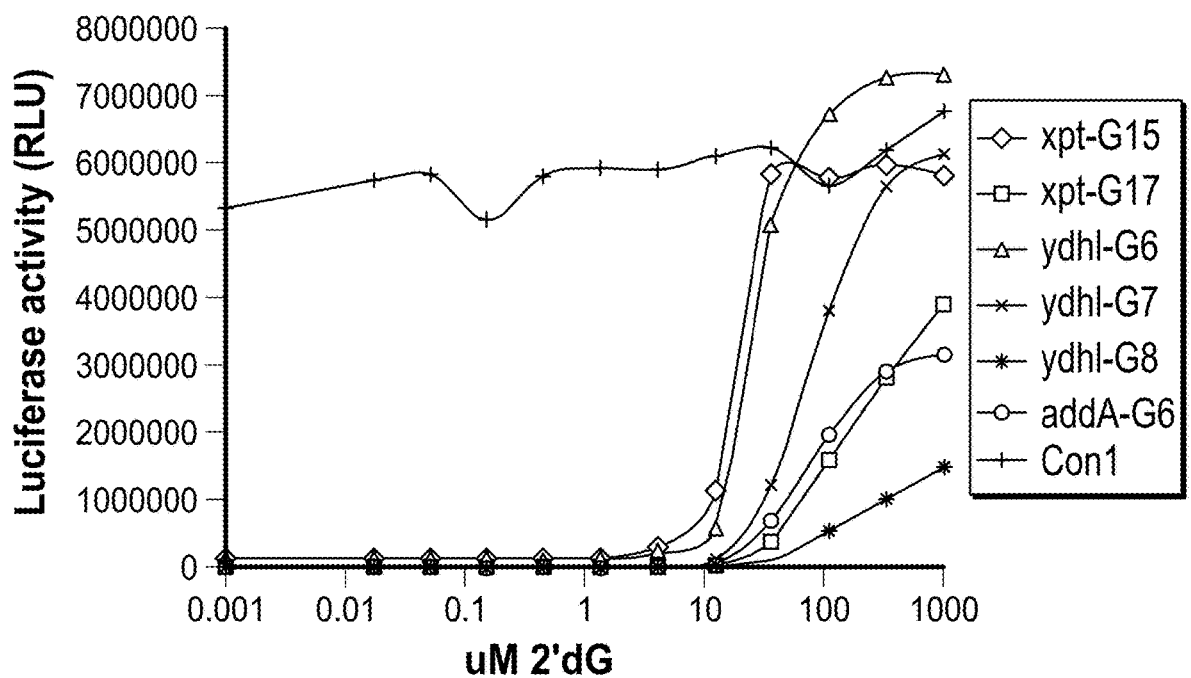

To test additional aptamers in our gene regulation system, we used the same strategy and method as described in previous Examples to generate multiple guanine and adenine responsive riboswitches by linking different guanine and adenine aptamers to the intron-mtDHFR-intron cassette (FIG. 6a). The guanine riboswitches that were tested efficiently regulated the expression of the luciferase gene in response to guanine (FIG. 6b). Additionally, we discovered that these guanine riboswitches regulated the expression of the target gene in response not only to guanine (FIG. 6b), but also to guanosine (FIGS. 6c), and 2'deoxyguanosine (2'dG) (FIG. 6d).

Figure 6E:
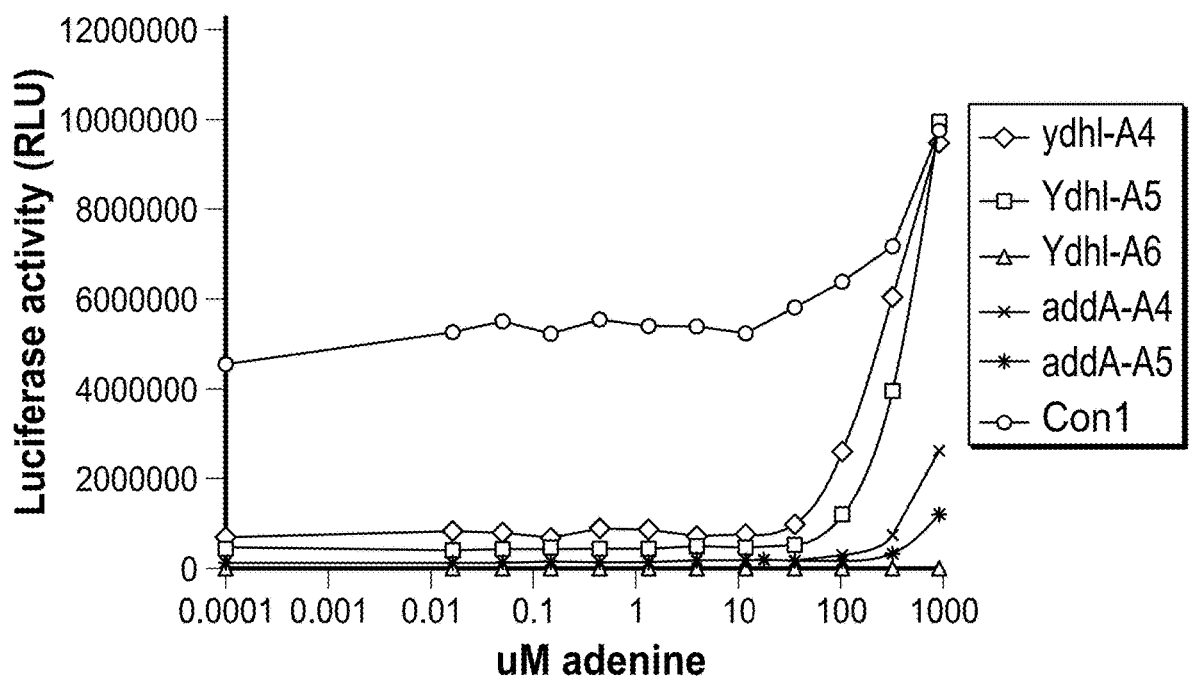

A number of adenine riboswitches (FIG. 6a) were generated, and also demonstrated gene regulation functionality (FIG. 6e).

The differences in the regulation of gene expression for the different aptamer containing constructs tested could reflect differences in aptamer/ligand binding affinity and aptamer secondary structure that may affect the accessibility of 5' ss, alternative exon inclusion, and therefore target gene expression. The Intron-Exon-Intron gene regulation cassette can be optimized by changing aptamer sequences to achieve desired level of gene regulation.

Example 7. The on/Off State of Target Gene Expression Regulated by Mammalian Guanine Riboswitch Experimental Procedures The intron-mtDHFR-aptamer-intron cassette was PCR amplified and cloned using Golden Gate cloning strategy (NEB) into pEGFP-C1 vector. To obtain a cell line stably expressing EGFP with riboswitch, HEK-293 cells were electroporated with 20 ng of plasmid DNA. Forty eight hours after electroporation, cell culture was selected with 800 µg/ml G418 for 2 weeks for cells that stably express the cassette. Cells were trypsinized and cell suspension was subjected to flow cytometric analysis of intensity of GFP fluorescence using a Guava EasyCyte 8HT machine. The resulting data was analyzed using GuavaSoft2.2.2.

Results

Figure 7A:
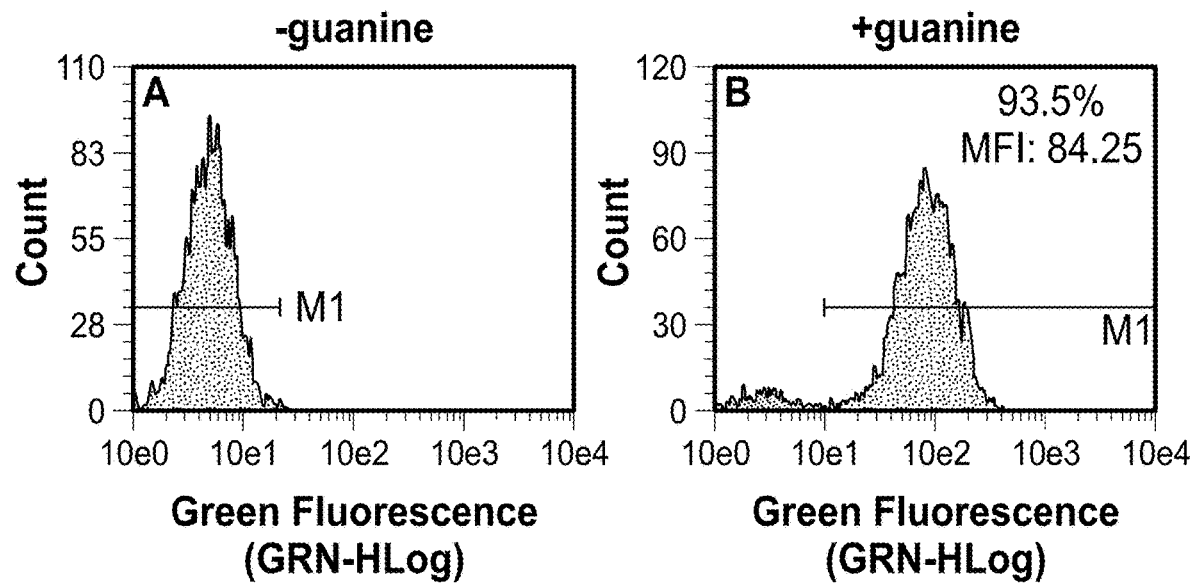
FIG. 7a. Induction of EGFP with the xpt-G17 containing regulatory cassette by guanine. The Intron-Exon-Intron cassette with xpt-G17 riboswitch was cloned into EGFP gene. HEK 293 cells stably transfected with the construct were treated with 500 µM guanine and assayed by flow cytometry analysis for GFP expression 6 hr after treatment. Guanine treatment resulted in increased EGFP expression, FIG. 7a, (B).
Figure 7B:
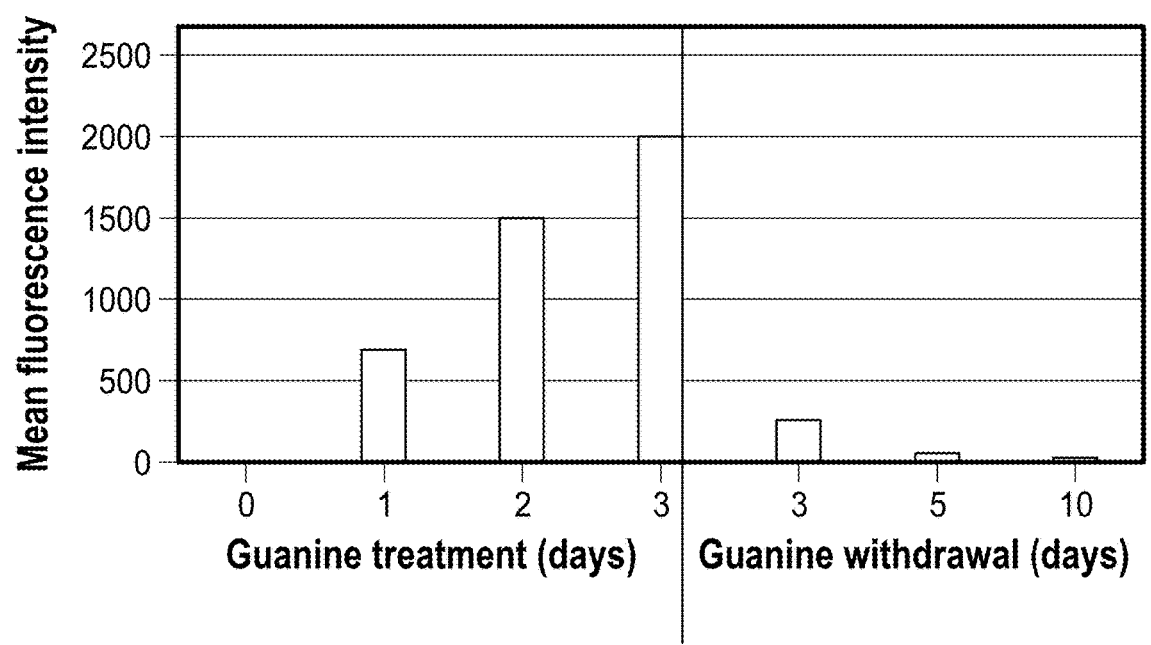
FIG. 7b. Target gene expression responds to the presence or absence of ligand. HEK 293 cells stably transfected EGFP with Intron-Exon-Intron cassette containing xpt-G17 riboswitch were treated for 3 days with 500 µM guanine, and assayed by flow cytometry analysis every 24 hr for 3 days. Guanine containing media was washed from the cells, and they continued to be grown without guanine treatment for a further 10 days, and the EGFP expression was monitored. EGFP expression increased when guanine was present in the cell culture media. On withdrawal of guanine EGFP, expression was lost.

To further demonstrate that expression of a target gene containing our Intron-Exon-Intron regulatory cassette can be regulated by exposure to the ligand specific to the aptamer contained within the riboswitch, the intron-mtDHFR-intron cassette containing the xpt-G17 riboswitch (SEQ ID NO.: 15) was inserted into the EGFP gene, and stably transfected HEK 293 cells. In the presence of guanine, EGFP expression was switched on (FIG. 7a). The fluorescence was detected as early as 6 hours after guanine treatment and increased over 3 days of guanine treatment, reaching close to 300-fold induction compared to untreated cells (FIG. 7b), indicating the "on" status of target gene expression in the presence of aptamer ligand. When guanine was withdrawn from the cell culture medium, EGFP expression diminished, indicating the "off" status of the target gene expression in the absence of the aptamer specific ligand (FIG. 7b). Thus, we have created a gene regulation platform, comprised of an Intron-Exon-Intron cassette containing a synthetic riboswitch, through which the expression of a target gene is regulated, in mammalian cells, by the presence or absence of a specific aptamer ligand.

Example 8. Effects of Multiple Regulation Cassettes on Regulating Target Gene Expression Experimental Procedures Constructs were made using Golden Gate cloning strategy (NEB). HEK 293 cells were transfected with the indicated constructs, treated with the 500 µM of guanine or 1 mM guanosine (Sigma) 4 hr after transfection. Luciferase activity was assayed as described in Example 5.

Results

Figure 8A:
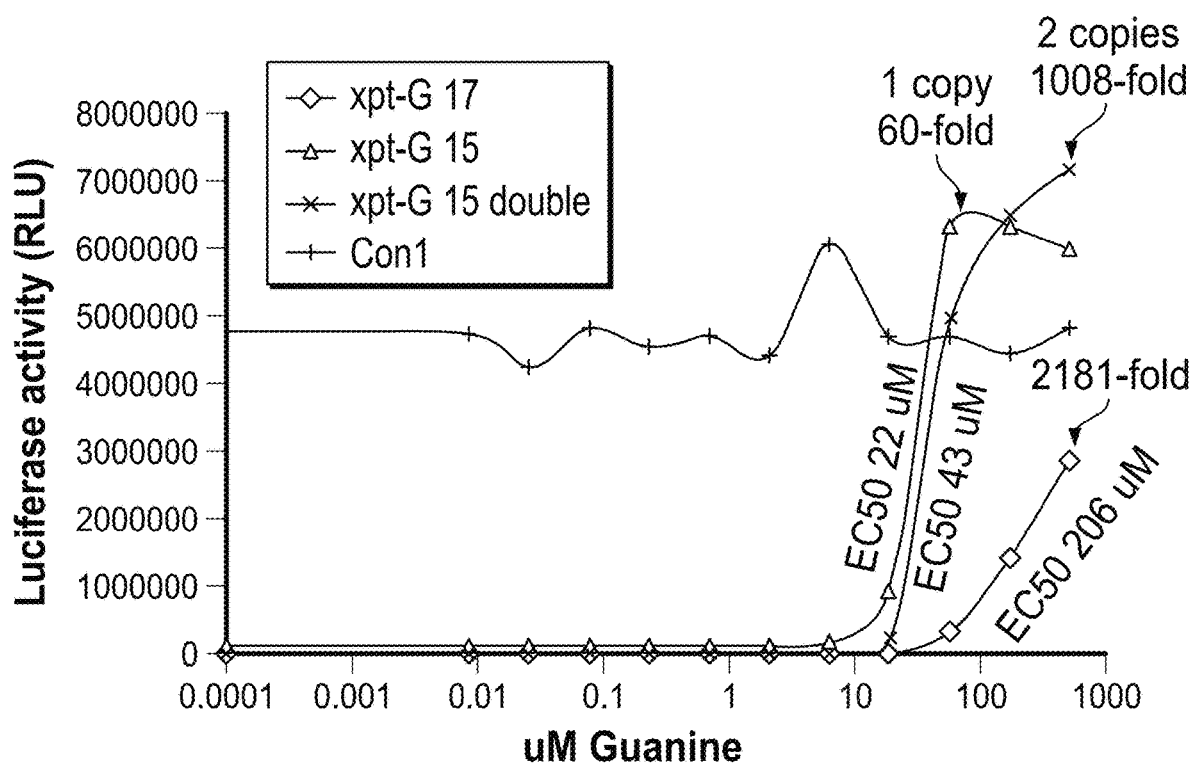
FIG. 8a. Luciferase expression regulated by two copies of the xpt-G15 containing regulatory cassette. The graph shows the guanine dose response of constructs with a single xpt-G17 or xpt-G15 containing regulatory cassette inserted into the target gene, and a construct with two copies of xpt-G15 containing regulatory cassette (xpt-G15 double).

The construct with the xpt-G15 (SEQ ID NO.: 46) containing regulatory cassette (DHFR_G15; Example 5), showed 60-fold induction of luciferase expression in response to guanine treatment, compared to the un-induced basal expression level and reached nearly 100% of level of luciferase expressed by Con 1 (FIG. 8a). This is a useful feature when regulating a therapeutic protein that is required at high levels.

In contrast, the construct with the xpt-G17 containing regulatory cassette (DHFR_G17) had significantly higher fold induction of 2181-fold, due to the lower un-induced baseline expression, but a considerably lower maximal level of expression upon induction compared to Con1 (FIG. 8a).

To test whether two copies of the xpt-G15 containing regulatory cassette (xpt-G15 double; SEQ ID NO.: 64) could reduce basal levels of expression, without compromising the maximal expression level of luciferase upon induction, two copies of the xpt-G15 containing regulatory cassette were embedded into the luciferase gene, each copy at a different location in the gene sequence. When two copies of xpt-G15 containing regulatory cassette were present, the un-induced baseline expression was decreased resulting in a significantly higher induction fold (from 60-fold to 1008-fold), without compromising the maximum expression level (FIG. 8a).

The EC50 of guanine for the xpt-G15 double cassette (xpt-G15 double; SEQ ID NO.: 64) was 5 times lower than the EC50 of guanine for the construct containing a single copy of the the more stringent xpt-G17 containing cassette (43 µM v.s. 206 µM), thus increasing the sensitivity of ligand response (FIG. 8a).

Figure 8B:
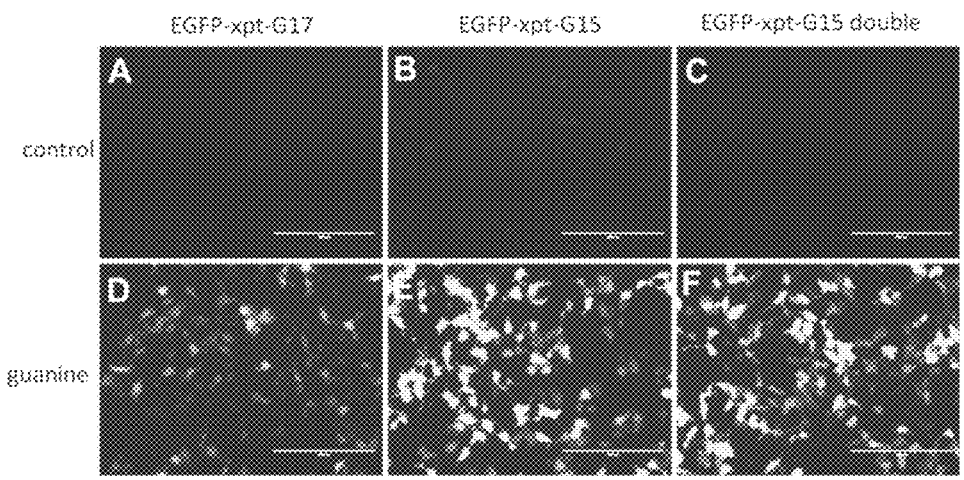
FIG. 8b. EGFP expression in tissue culture cells regulated by different regulatory cassettes. One copy of the xpt-G17 containing cassette (EGFP-xpt-G17) results in low un-induced baseline expression (A), and reaches a lower induced level of expression compared to the cells containing the EGFP-xpt-G15 construct (D). One copy of the xpt-G15 containing cassette (EGFP-xpt-G15) gives higher un-induced baseline expression (B) as well as higher induced expression (E). With the construct containing two copies of the xpt-G15 containing cassettes (EGFP-xpt-G15 double), the background un-induced expression is reduced (C) without reducing the induced level of expression (F), thus the fold induction is increased. Cells were treated with guanine and imaged 24 hr after treatment.
Figure 8C:
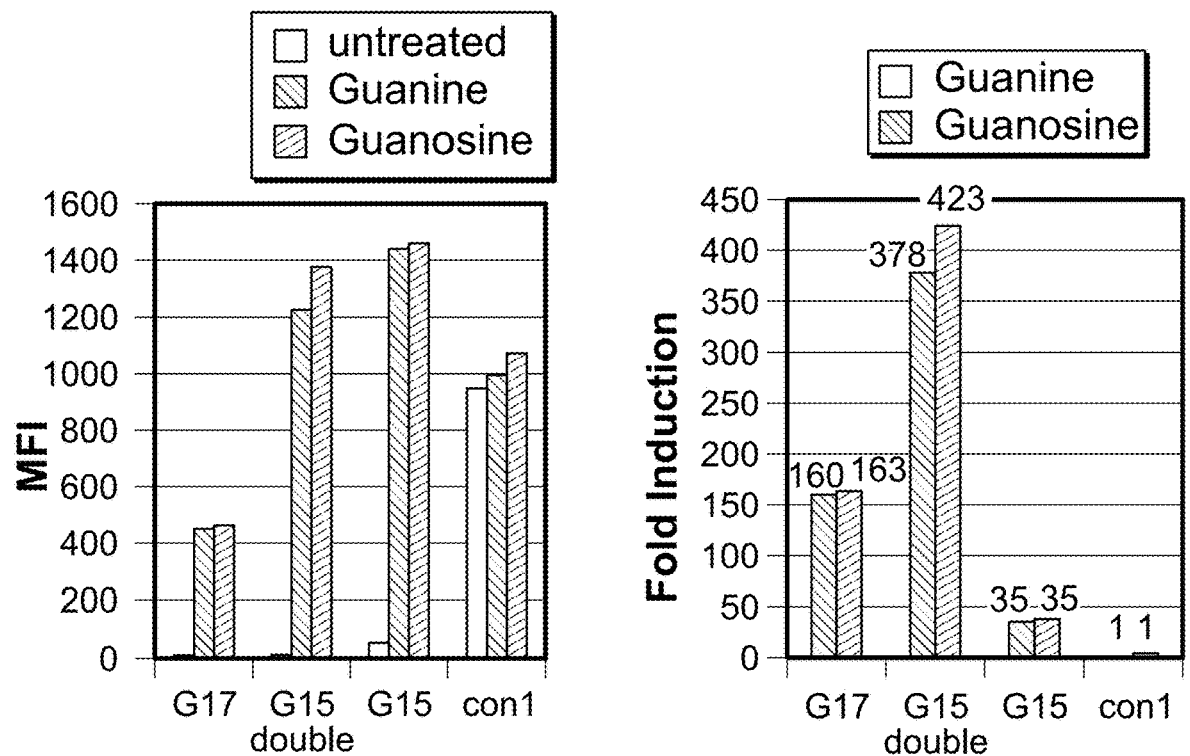
FIG. 8c. Regulatory cassettes containing the xpt-G15 and xpt-G17 riboswitches respond to both guanine and guanosine. Quantification of EGFP expression (mean fluorescence intensity) was analysed by flow cytometry, and the fold induction was calculated as mean fluorescent intensity (MFI) obtained with guanine or guanosine treatment divided by MFI obtained without treatment. Treatment with guanine and guanosine gave similar levels and fold induction.

The strategy of using two copies of a less stringent regulatory cassette to enhance fold induction and maximal induced gene expression, was also applied to the EGFP gene. As shown in FIGS. 8b and 8c, consistent with the results for luciferase regulation (FIG. 8a), a single copy of the xpt-G15 regulatory cassette in the EGFP gene (EGFP-xpt-G15) generated higher un-induced baseline level of EGFP expression when compared with the xpt-G17 regulatory cassette containing construct (EGFP-xpt-G17). However, when two copies of xpt-G15 regulation cassette were inserted into the EGFP gene at different locations (EGFP-xpt-G15 double), the un-induced baseline expression level of was decreased to that of EGFP-xpt-G17 with the induced level of EGFP even higher than Con1-EGFP control (FIG. 8c).

Figure 8D:
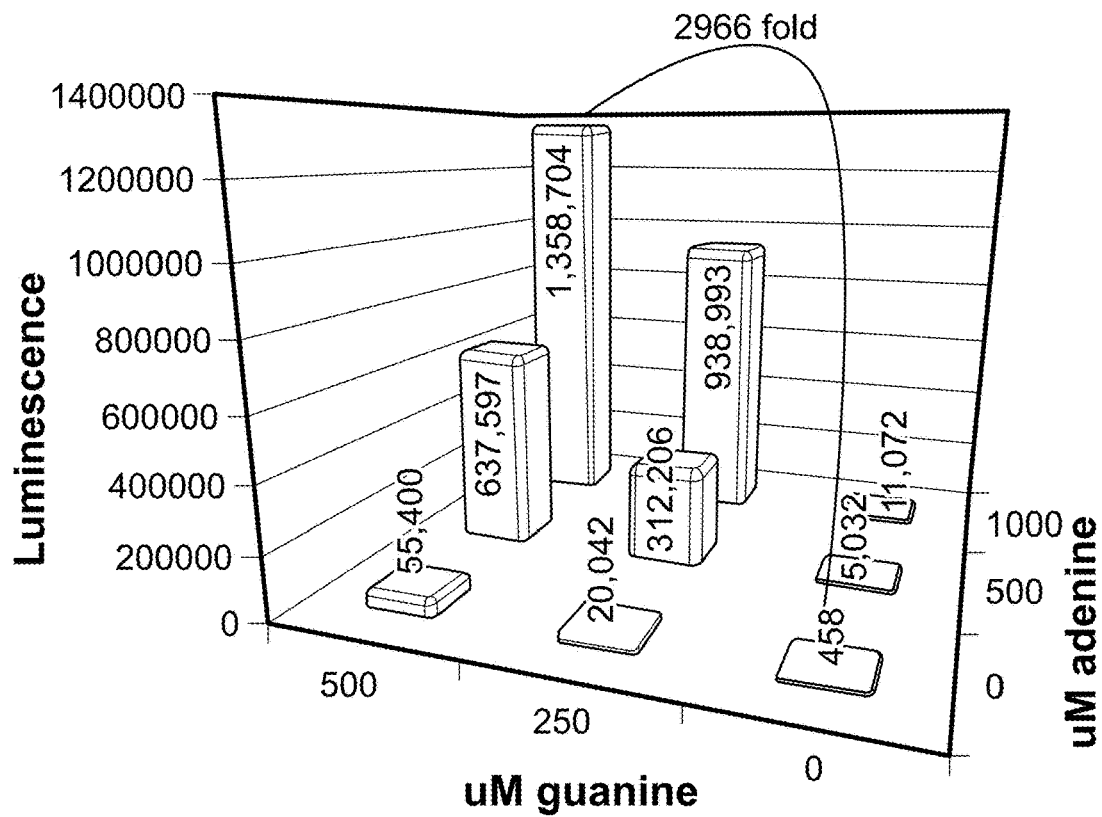
FIG. 8d. Luciferase expression from a construct containing one copy of the xpt-G17 containing regulatory cassette in addition to one copy of the Ydhl-A5 containing regulatory cassette. HEK 293 cells transfected with this construct were treated with either guanine or adenine, or both. The highest induction of luciferase was seen with combined use of both ligands at their highest concentrations.

Further, one copy of the xpt-G17 containing regulatory cassette and one copy of a Ydhl-A5 adenine riboswitch containing regulatory cassette were embedded into the luciferase gene. Luciferase expression was induced by either addition of adenine (25-fold) or addition of guanine (120-fold) alone, however, a significantly higher level of induction was achieved (up to 2966-fold) with the combined use of adenine and guanine at each of their highest concentration used (FIG. 8d). These results demonstrate the modularity of the alternative splicing based riboswitches in regulating target gene expression.

In order to reduce recombination and increase the ease of production of viral vectors containing two or more regulatory cassettes, regulatory cassettes with different intron and exon sequences may be used in a single target gene, and these may contain either the same or different ligand responsive aptamers.

Example 9. Effects of Intron Size and Sequence on Regulating Target Gene Expression Via Aptamer-Mediated Alternative Splicing Experimental Procedures The Con1 construct was used as a template for PCR amplification of intron fragments that have either upstream or downstream intron deletions. To generate constructs that have single intron deletions, PCR products were cloned into the constructs containing the xpt-G17 riboswitch using Golden Gate cloning strategy (NEB). To generate constructs with both upstream and downstream intron deletions, fragments released by EcoRI and BamHI from constructs with single deletions in the downstream intron sequence were cloned into EcoRI and BamHI-digested constructs with single deletions in the upstream intron sequence.

Results

Introns contain elements that may either promote (intronic splicing enhancer, ISE) or suppress (intronic splicing suppressor, ISS) exon splicing. Among all the riboswitches we have generated, xpt-G17 demonstrated the best regulating ability in terms of both the induction fold and the level of induced gene expression. Using the xpt-G17 riboswitch in the Intron-Exon-Intron cassette, we made a series of modification in the intron sequences and intron length and in the splice sites to further optimize the system.

Figure 9A:
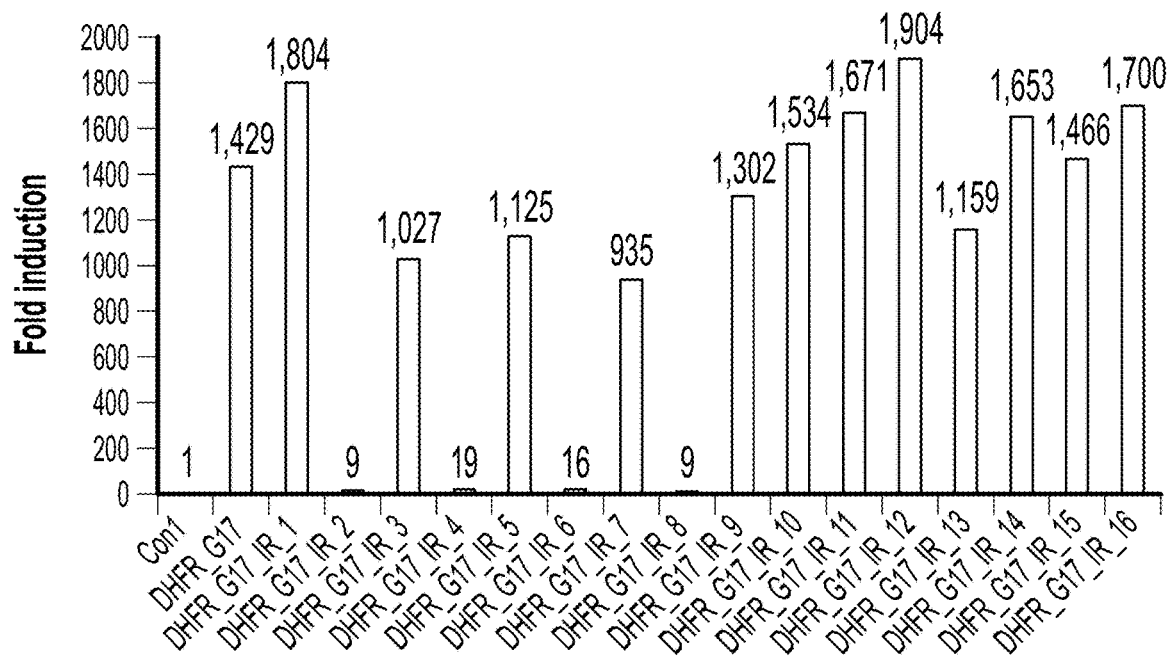
FIGS. 9a and 9b. The effects of intron truncations on luciferase expression regulated by the Intron-Exon-Intron regulatory cassette containing the xpt-G17 riboswitch.
Figure 9B:
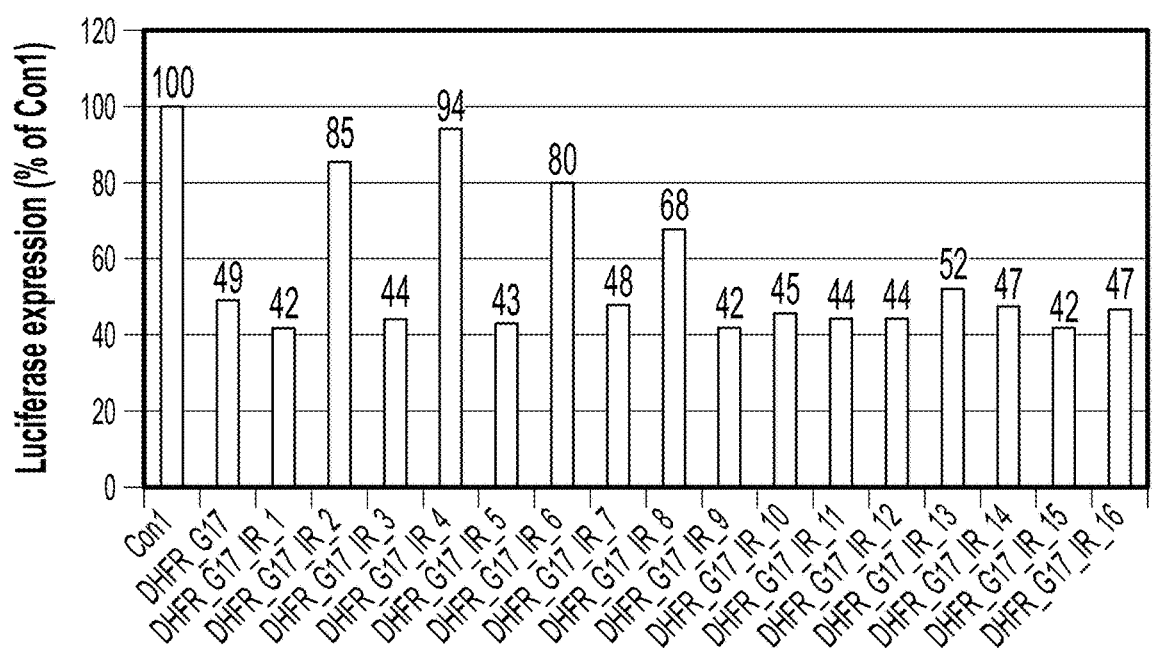
Figure 9C:
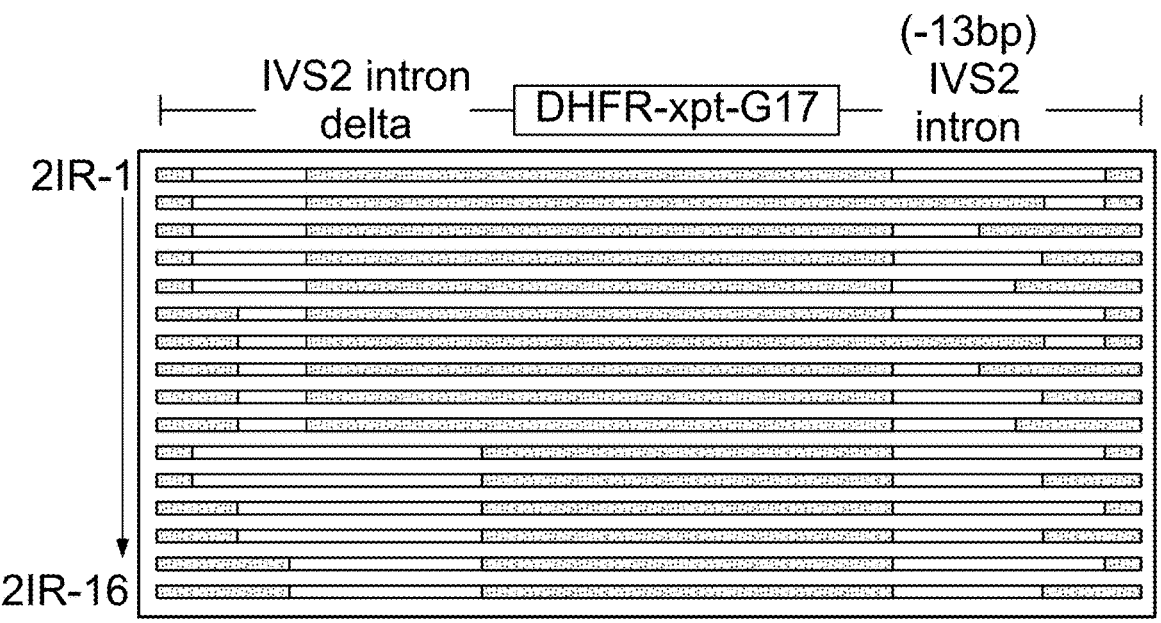
FIG. 9c. Diagram of sequences deleted from the Intron-Exon-Intron regulatory construct DHFR_G17. The deleted sequence is depicted by the open bar, remaining sequence depicted by the solid bar.
Figure 9D:
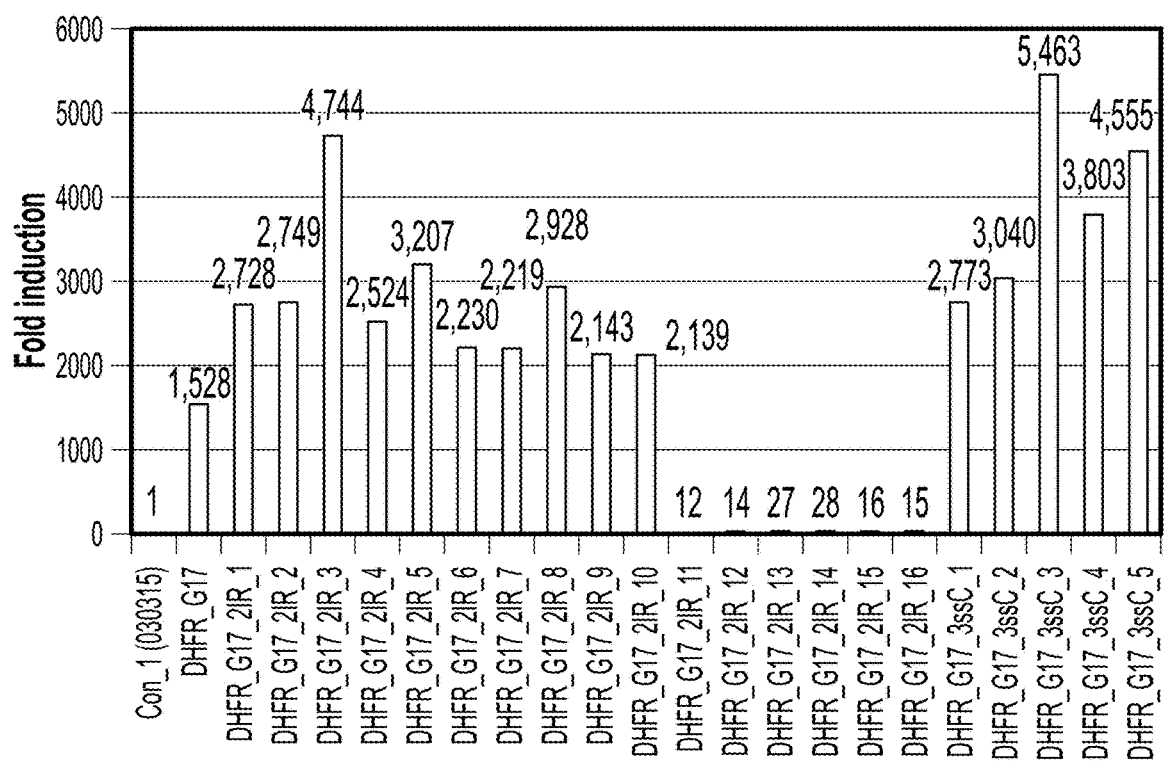
FIGS. 9d and 9e. The effect of different intron deletions, depicted in FIG. 9c, on gene regulation. Sequences within the introns flanking the alternative DHFR exon modified exon splicing and relative gene regulation. For example, DHFR-G17_2IR 3 shows intron deletions that result in a significant increase in the fold of target gene expression.
Figure 9E:
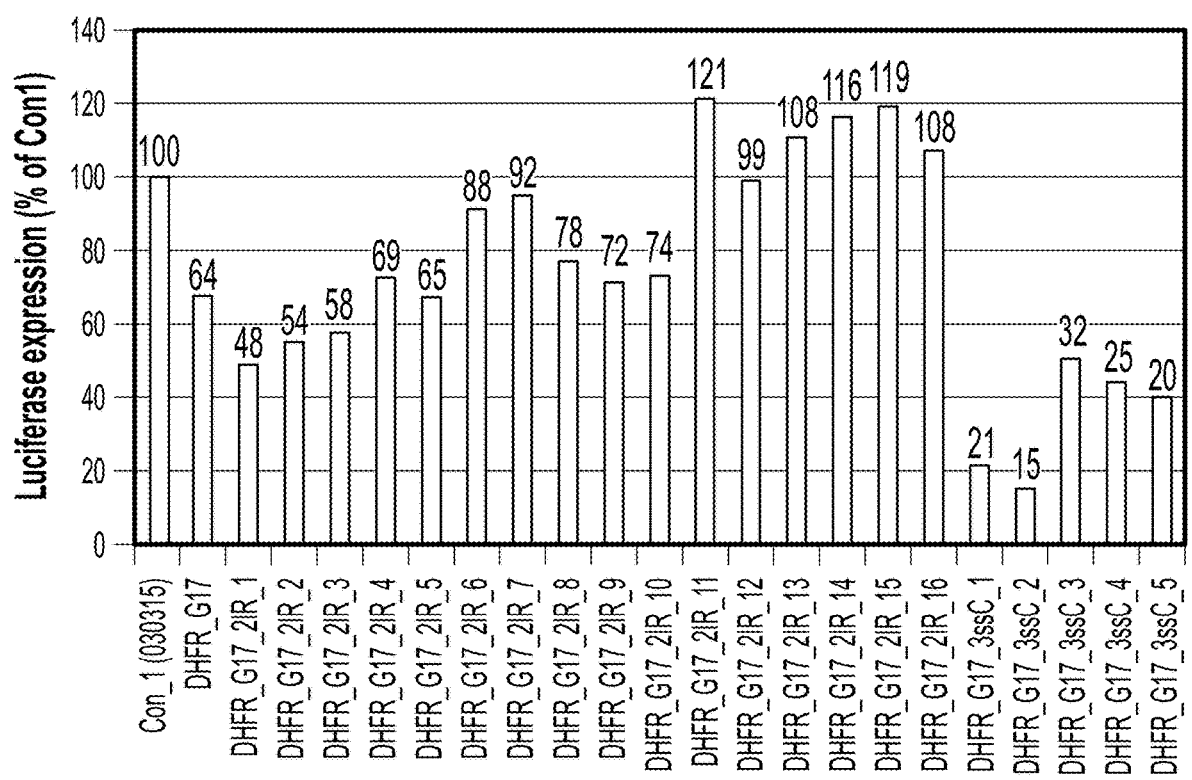

First, the effect of intron modification was tested by introducing single deletions in intron sequences either upstream or downstream of the mtDHFR exon (FIG. 9a, 9b) 16 constructs with the xpt-G17 containing riboswitch were generated xpt-G17-IR-1 through xpt-G17-IR-16 (sequences of 13 of these constructs are given in Table 5, SEQ ID NOS: 16-28). Then, upstream and downstream intron deletions were combined to generate larger intron deletions, as depicted in FIG. 9c. As shown in FIGS. 9d and 9e, of the 16 constructs made with two intron deletions (2IR), constructs 2IR-1 through 2IR-10 (SEQ ID NOS.: 29-38) showed significantly higher induction folds, without compromising the induced expression level of luciferase, with 2IR-3 having the greatest improvement in fold induction (4744-fold). In addition, we also made constructs with a mutated 3' ss upstream of mtDHFR exon and also reduced the size of the downstream intron. As shown in FIGS. 9d and 9e (constructs DHFR_3ssC_1 to 5) these modifications further improved the relative fold induction, however in this case a reduction in the level of induced expression was observed (from 64% to 32% for 3ssC_3).

These results indicate that the gene regulating ability of the Intron-Exon-aptamer-Intron cassette can be optimized through modifying the intron sequences flanking the alternative exon in order to achieve the desired level of gene regulation.

Example 10. The Use of Multiple Natural Exons as Well as Synthetic Exons in the Gene Regulation Cassette Experimental Procedures Sequences of mutant human Wilms tumor 1 exon 5 (mutWT1-e5, SEQ ID NO.: 61), SIRT1 exon 6 (SIRT1-e6, SEQ ID NO.: 62), mouse calcium/calmodulin-dependent protein kinase II delta exon 16, or 17 (Camk2d-e16 or e17, SEQ ID NOs.: 59, 60), and synthetic exon ENEEE (SEQ ID NO.: 63) were synthesized (IDT) and cloned into the DHFR-G17 vector in place of the DHFR exon using Gibson Cloning kit (NEB). Plasmid DNA was transfected into HEK 293 cells, treated with 500 µM guanine, and luciferase assay performed as described in Example 1. The sequences of each exon with 5' and 3' splice sites are shown with exonic sequences in uppercase letters (Table 5, SEQ ID NOS.: 59 to 63).

Results

Figure 10A:
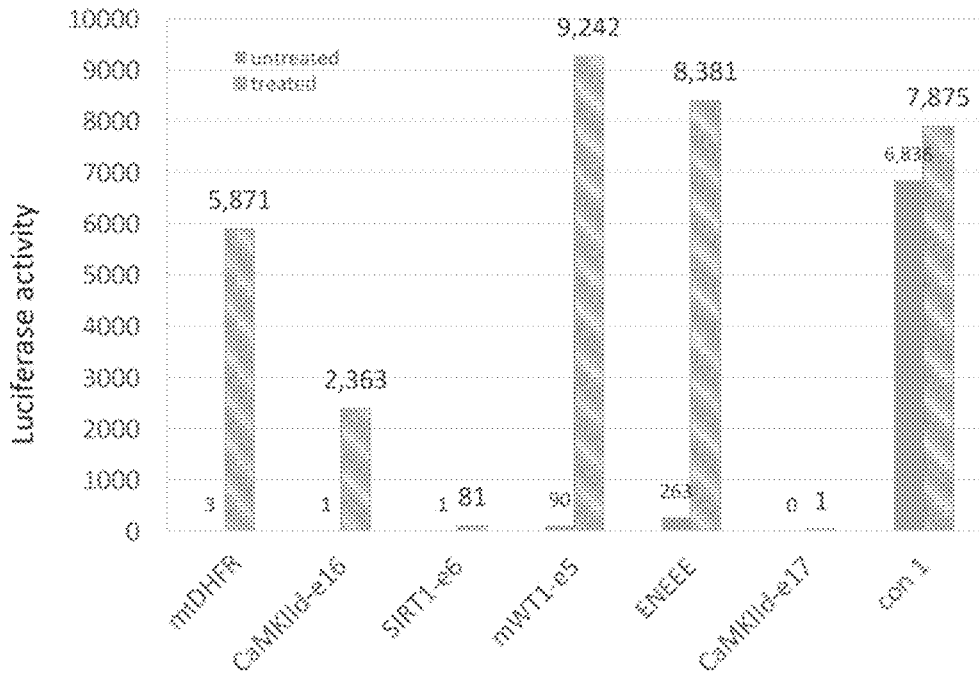
FIGS. 10a and 10b. Different exons can act as the alternative exon in the Intron-Exon-Intron regulatory cassette to regulate gene expression.
Figure 10B:
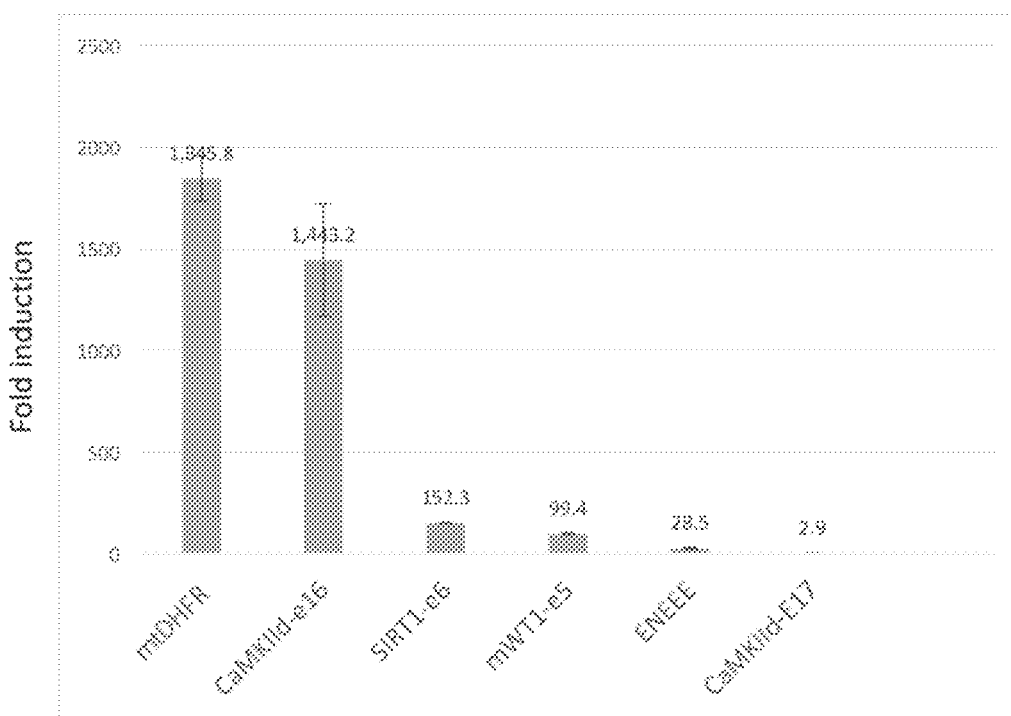

In order to determine that the regulating function of our Intron-Exon-aptamer-Intron cassette is not limited to a specific exon sequence, we replaced the mtDHFR exon in the construct containing the guanine xpt-G17 riboswitch (DHFR-xpt-G17), with multiple different natural and mutant exons as well as synthetic exons that contain known exonic splice enhancer sequences (ESE). As shown in FIG. 10, the regulation cassette with the CamkIId-e16 exon generates nearly equivalent fold induction compared to DHFR-xpt-G17 but with a lower level of both basal and induced luciferase expression. Cassettes containing other exons also showed variable levels of both basal and induced luciferase expression. Thus, the aptamer-mediated alternative splicing gene regulation cassette is not exon-specific, and not limited to the mDHFR-e2 exon.

Exons that can generate efficient alternative splicing events are suitable for the aptamer-mediated gene regulation cassette. These results further indicate that the gene regulating capability of this Intron-Exon-aptamer-Intron cassette can be optimized by modifying the sequences in the alternative exon as well as surrounding intron sequences, for example the splicing strength of the 5'ss and 3' ss sequences of the alternative exon as well as ESE and ESS sequences in the alternative exon as described herein.

Example 11. Regulation of Target Gene Expression by Aptamer-Mediated Alternative Splicing In Vivo in Mice Experimental Procedures Hydrodynamic DNA delivery and drug treatment: 5 µg or 10 µg of endotoxin-free plasmid DNA containing the luciferase gene with two copies of the xpt-G15 containing regulatory cassette (xpt-G15 double, SEQ ID NO.: 64; Example 8, FIG. 8a), diluted in saline (Qiagen Endofree kit) was injected through tail vein in a volume of 10% body weight over 5 to 10 seconds to 6-7 weeks old CD-1 female mice. Guanosine (Sigma) was suspended in 0.5% methylcellulose/ 0.25% Tween 80 (Sigma) in water freshly and administrated orally at 2 hr and 12 hr post DNA injection, or, delivered through intraperitoneal injection (IP) at 5 hr, 12 hr, 16 hr and 24 hr post DNA delivery.

Noninvasive live animal bioluminescence imaging: before imaging, mice were anesthesized with 2% isoflurane, and injected with 150 gm/kg body weight of luciferin, and images were taken within 2 to 5 minutes after luciferin injection using Bruker Xtreme system at the indicated time point post DNA injection. Luciferase activity was expressed as mean photon/sec±s.d. The induction fold was calculated as the quotient of photon/sec obtained in mice treated with guanosine divided by value obtained in mice without guanosine treatment.

Results

We assessed the gene regulating function of the Intron-Exon-Intron regulatory cassette in mice, in vivo. Endotoxin-free plasmid DNA of a construct containing two copies of xpt-G15 riboswitch in the luciferase gene (xpt-G15 double) was delivered to the liver in mice through hydrodynamic injection, and guanosine was administrated intraperitoneally. We tested two routes of guanosine delivery. In one experiment (FIGS. 11a and 11b) mice were administered with different doses of guanosine orally 2 hr and 12 hr after DNA delivery, then were imaged. As shown in FIG. 11a, mice treated with guanosine showed higher luciferase expression at 9 hours post DNA. The luciferase expression in guanosine treated mice increased over time reaching the highest level at 48 hours post DNA injection, after which expression declined.

In a separate experiment (FIG. 11c and FIG. 11d), guanosine was administered intraperitoneally. At 4 hours post DNA injection (P.I.) and before guanosine treatment, mice in each group showed similar level of basal luciferase activity (FIG. 11). Then, mice were treated with either vehicle as control, or guanosine. At 11 hours P.I., luciferase activity increased in all the mice, consistent with the report that luciferase gene expression peaks 12 hours post hydrodynamic DNA injection in the liver. However, in mice treated with guanosine, there is a significantly higher level of luciferase expression compared to that in untreated mice, 4.7-fold and 16.2-fold induction compared to the uninduced baseline expression was seen with 100 mg/kg and 300 mg/kg of guanosine, respectively.

Thus, the splicing-based gene regulation cassette was shown to regulate gene expression in vivo in animals, in a dose dependent manner, in response to the administration of the ligand specific for the aptamer contained within the regulatory cassette.

Example 12. Delivery of Riboswitch Constructs to the Murine Retina Via Adeno Associated Viral (AAV) Vectors Experimental Procedures AAV Plasmid constructs: Two riboswitch expression constructs (described in the table below) were adapted via molecular cloning into a format able to be packaged as an AAV genome.

TABLE 4

| Name | Riboswitch inducible element | Promotor | Transgene reporter |
| --- | --- | --- | --- |
| GTX5 | None (control) | CMV | Enhanced Green Fluorescent Protein (eGFP) |
| GTX7 | G15 | CMV | Enhanced Green Fluorescent Protein (eGFP) |

Expression constructs based around the EGFP transgene (GTX 5-7) were digested with restriction enzymes MfeI and NheI releasing an ~1400 bp DNA fragment containing the Riboswitch inducible element and EGFP transgene. A pD10 AAV genome plasmid was also digested with MfeI and NheI, releasing a 4475 bp fragment containing the AAV ITRs, CMV promotor and SV40 polyadenylation signal. The two fragments were ligated using T4 DNA ligase resulting in plasmids containing sequence with the following structure, able be packaged as an AAV2 genome:

[ITR]-[CMV]-[5' EGFP]-[Riboswitch Element]-[3' EGFP]-[SV40]-[ITR]

All resulting plasmid constructs were verified by DNA sequencing and named according to the following convention: pD10-GTX #.

AAV Vector Production and titration: Adeno-associated virus (AAV) was produced in vitro by transient transfection of HEK-293T cells with three plasmids.

(i) Viral Genomic plasmid based upon pD10 backbone
(ii) AAV Packaging plasmid containing the AAV2 Rep78 gene and a viral capsid gene. Many different serotypes of AAV can be produced by varying the capsid gene sequence but in this case an AAV8 capsid was used.
(iii) Helper plasmid (pHGTI-Adeno1). This plasmid provides a near minimal set of the Adenovirus genes that AAV requires to package and assemble.

These plasmids were transfected into HEK-293T cells in the ratio 1:1:3, with a total of 50 µg of plasmid DNA was transfected per 80-90% confluent 150 cm$^2$ plate. A typical production run consisted of 20 such plates. The transfection reagent used was polyethylenimine (PEI) at a PEI to DNA ratio of 2.25:1 (w/w). Seventy-two hours after transfection, cells were physically detached from the plates and pelleted by centrifugation; the resulting cell pellet was resuspended in 20 mL of TRIS density buffer. The pellet was then lysed by repeated Freeze/Thaw/Vortex cycles and any non-packaged DNA remaining in the lysate was destroyed by Benzonase digestion. The lysate was then clarified by dead-end filtration and centrifugation before being diluted up to a total volume of 50 mL.

Clarified lysate was then purified via an affinity based FPLC procedure using an AVB column on an AKTA Pure instrument (both GE Healthcare) run according to pre-programmed protocols. The final AAV containing eluate from the FPLC column was concentrated down to a volume of ~200 µL by centrifugation at 5000×g in a 10,000 MW cut off Vivaspin 4 centrifugal concentrator (GE Healthcare), 2 mL of PBS-MK was added (to dilute out high salt elution buffer), and the eluate re-concentrated back to ~200 µL using the same concentrator. This material constituted the purified AAV virus, and was aliquoted as appropriate and stored at −80° C.

Vector titer was established using qPCR (targeted against the SV40 polyadenylation signal) directly upon a sample of purified vector. The resulting cycle threshold value was compared against a known standard curve and the number of vector genomes per mL was calculated.

Riboswitch AAV vectors were named according to the following convention: AAV2/[capsid serotype #]-GTX #

Murine subretinal injections: Injections of vector into the subretinal space were performed upon mice under general anesthesia using a manually guided 10 mm, 34-gauge needle mounted on a 5 µL Hamilton syringe. Needle tip was guided into injection position by observation of the retina via an operating microscope. In all eyes receiving vector, 2×2 µL injections were performed, with one injection placed in the superior hemisphere of the eye and another in the inferior hemisphere. After injection, the quality of the resulting retinal detachment and any reflux of injected material was recorded.

Fluorescent fundus photography: Following subretinal injection, EGFP transgene expression was periodically assessed by Fundus photography using a slit lamp (SC-16, Keeler) with an attached Leica DC500 digital camera. Animals were placed under general anesthesia and their pupils dilated with 1% topical tropicamide. Corneal refractive power was neutralized by placing a coverslip on the cornea covered with a coupling medium solution (Viscotears). Under bright white light, the instrument was adjusted and the animal positioned so that the retina was in sharp focus and the optic disk was centered in the field of view, a bright field image was then taken using a 200 ms exposure time. Transgene (EGFP) fluorescence was assessed by filtering the light source (475±25 nm) and taking two further images with 10 and 30 s exposures.

Results

The riboswitch constructs (Table 4) were successfully cloned into a format able to be packaged as an AAV genome as shown by DNA sequencing of the ligation products. Of the resulting constructs, pd10-GTX7 and pd10-GTX5 were further produced as AAV2/8 viral vectors. The vectors produced were shown to have the following titers by qPCR:

AAV2/8-GTX7: $1.17 \times 10^{13}$ Vector Genomes/mL
AAV2/8-GTX5: $1.73 \times 10^{13}$ Vector Genomes/mL These two vectors were then injected subretinally and left for 8 days for EGFP transgene expression to develop before assessing expression by fluorescent fundus photography. FIG. 12 shows that EGFP is expressed in a retina injected with AAV2/8-GTX7. Transgene expression is low, but substantial expression from AAV2/8-GTX7 would only be expected after induction via aptamer-mediated alternative splicing in response to ligand (which was not added).

Example 13. Regulation of Target Gene Expression by Regulation Cassette-Mediated Alternative Splicing In Vivo in the Murine Retina Following AAV Delivery Procedures Quantification of Fluorescent fundus photography (EGFP signal): All manipulation and analysis of images was performed using GNU Image Manipulation Program (GIMP, open source). As described above, three images of each retina were taken at each point of imaging: White light (200 ms), 475±25 nm (10 s) and 475±25 nm (30 s). First these three images were superimposed as layers, and using the white light image as a guide, a region of interest (ROI) was defined to encompass the entire retina visible through the pupil. Upon the two 475±25 nm (EGFP fluorescence) images the threshold tool was used to highlight only those pixels with an intensity value above a defined threshold. The threshold value was selected upon the basis of defining clean separation of EGFP signal from background, and to provide an appropriate dynamic range for analysis. The number of pixels above threshold within the ROI was recorded for each image. To correct for variable dilation of the pupil leading to variation in the area of retina visible between eyes the number of pixels above threshold was divided by the total number of pixels within the ROI.

Induction: Riboswitch-mediated induction of target gene expression was carried out via two routes of administration as described below:

Intraperitoneal injection (I.P.): A volume of 100 μL of [75 mg/ml guanosine +0.5% w/v Methyl Cellulose+0.25% v/v Tween 80 in Water] was injected into the intraperitoneal cavity using a 13 mm, 30-gauge needle. This equates to a dose of guanosine of 300 mg/kg in an adult mouse weighing 25 g.

Intravitreal injection (I-Vit.): A volume of 2 μL of [1 mM guanosine+2.5% DMSO in PBS-MK] was injected intravitreally using a manually guided 10 mm, 34-gauge needle. The needle tip position upon injection was below the lens directly above the optic disk, having been guided into this position by observation of the retina via an operating microscope.

Results

A total of 9 eyes were injected subretinally as described in Example 12 as follows on day 00:

6 eyes with AAV2/8-GTX7 (EGFP transgene expression from the CMV promotor regulated by the G15 riboswitch element)

3 eyes with AAV2/8-GTX5 (Positive control construct, unregulated EGFP transgene expression from the CMV promotor)

Fluorescent fundus photography as described in Example 12 was performed on days 02, 08, 09, 10 and 12.

All eyes received induction via Intraperitoneal injection after fluorescent fundus photography on days 08, 09 and 10. All eyes received induction via Intravitreal injection on day 11. Fluorescent signal was quantified as described above and example images are shown in FIG. 13a.

No induction was carried out during the first 8 days post vector injection as gene expression from AAV2/8 is known to take up to 7 days to become maximal. The expression level on day 8 was therefore taken as the pre-induction base line. On day 10 post vector injection after 2 rounds of I.P. induction, transgene expression had increased by ~3.5× compared to this baseline ($P \leq 0.05$, 1-way ANOVA, Dunnetts) as shown in FIG. 13c and FIG. 13a (L vs N).

On day 12 post vector injection, 24 hrs following intravitreal induction and 48 hrs after the last I.P. induction, transgene expression had increased by ~9× compared to baseline ($P \leq 0.001$, 1-way ANOVA, Dunnetts) as shown in FIG. 13c and FIG. 13a (L vs O). This much larger induction following intravitreal induction implies (but does not definitively show) that this route of induction might be more effective than intraperitoneal injection.

Higher resolution images showing the difference in EGFP transgene expression pre and post induction are shown in FIG. 13b.

Over the same time period and under the same induction regime the EGFP expression levels mediated by the unregulated control vector AAV2/8-GTX5 did not vary significantly (1-way ANOVA, Bonferroni), remaining roughly constant as shown in FIG. 13d. Due to the large difference in expression level mediated by GTX7 vs GTX5, each set of images required a different exposure time (30 s and 10 s respectively) and threshold (50 and 190 respectively).

This data clearly shows that transgene expression from the G15 based GTX7 construct was being regulated via aptamer-mediated alternative splicing in the murine retina. The maximum level of transgene expression induced from GTX7 was lower than that mediated by the uninducable positive control construct GTX5

TABLE 5

Description and associated sequences. Exon sequence is in uppercase letters and intron sequence in in lowercase letters unless otherwise stated.

| SEQ ID NO. | Description | Sequence |
|---|---|---|
| SEQ ID NO.: 1 | Luci-IVSΔ-Luci in construct Con1 Human beta-globin intron 2 containing a deletion ("IVS2Δ") is in lowercase and flanking luciferase sequence is in uppercase. | GAGGTTCCATCTGCCAGGTATCAGGgtgagtctatgggac ccttgatgttttctttcccttcttttctatggttaagtt catgtcataggaaggggagaagtaacagggtacacatatt gaccaaatcagggtaattttgcatttgtaattttaaaaaa tgctttcttcttttaatatactttttgtttatcttattt ctaatactttccctaatctctttctttcagggcaataatg atacaatgtatcatgcctctttgcaccattctaaagaata acagtgataatttctgggttaaggcaatagcaatatttct gcatataaatatttctgcatataaattgtaactgatgtaa gaggtttcatattgctaatagcagctacaatccagctacc attctgcttttatttatggttgggataaggctggattat tctgagtccaagctaggccctttgctaatcatgttcata cctcttatcttcctcccacagCAAGGATATGGGCTCACTG AGACTACATCAGCTATTCT |

TABLE 5-continued

Description and associated sequences. Exon
sequence is in uppercase letters and intron
sequence in in lowercase letters unless
otherwise stated.

| SEQ ID NO. | Description | Sequence |
|---|---|---|
| SEQ ID NO.: 2 | Luci-IVSΔ-Luci in construct Con2 | GATTACACCCGAGGGGATGATAAAGtaagcctatgggac ccttgatgttttctttcccttcttttctatggttaagtt catgtcataggaaggggagaagtaacagggtacacatatt gaccaaatcagggtaattttgcatttgtaattttaaaaaa tgctttcttcttttaatatactttttgtttatcttattt ctaatactttccctaatctctttctttcagggcaataatg atacaatgtatcatgcctctttgcaccattctaaagaata acagtgataatttctgggttaaggcaatagcaatatttct gcatataaatatttctgcatataaattgtaactgatgtaa gaggtttcatattgctaatagcagctacaatccagctacc attctgcttttatttatggttgggataaggctggattat tctgagtccaagctaggccctttgctaatcatgttcata cctcttatcttcctcccacagCCGGGCGCGGTCGGTAAAG T |
| SEQ ID NO.: 3 | Luci-IVSΔ-Luci in construct Con3 | TTCTTCGCCAAAAGCAgtaagtctatgggaccccttgatgt tttctttcccttcttttctatggttaagttcatgtcata ggaaggggagaagtaacagggtacacatattgaccaaatc agggtaattttgcatttgtaattttaaaaaatgctttctt cttttaatatactttttgtttatcttatttctaatactt tccctaatctctttctttcagggcaataatgatacaatgt atcatgcctctttgcaccattctaaagaataacagtgata atttctgggttaaggcaatagcaatatttctgcatataaa tatttctgcatataaattgtaactgatgtaagaggtttca tattgctaatagcagctacaatccagctaccattctgctt ttatttatggttgggataaggctggattattctgagtcc aagctaggccctttgctaatcatgttcatacctcttatc ttcctcccacagCTCTGATTGACAAATACG |
| SEQ ID NO.: 4 | Luci-IVSΔ-Luci in construct Con4 | AAGAGCTGTTTCTGAGGAGgtgtggctatgggaccccttga tgttttctttcccttcttttctatggttaagttcatgtc ataggaaggggagaagtaacagggtacacatattgaccaa atcagggtaattttgcatttgtaattttaaaaaatgcttt cttcttttaatatactttttgtttatcttatttctaata ctttccctaatctctttctttcagggcaataatgatacaa tgtatcatgcctctttgcaccattctaaagaataacagtg ataatttctgggttaaggcaatagcaatatttctgcatat aaatatttctgcatataaattgtaactgatgtaagaggtt tcatattgctaatagcagctacaatccagctaccattctg cttttatttatggttgggataaggctggattattctgag tccaagctaggccctttgctaatcatgttcatacctctt atcttcctcccacagCCTTCAGGATTACAAGATTCAA |
| SEQ ID NO.: 5 | Luci-IVSΔ-Luci in construct Con5 | CATCTGCCAGGTATCAGGgtgagtctatgggaccccttgat gttttctttcccttcttttctatggttaagttcatgtca taggaaggggagaagtaacagggtacacatattgaccaaa tcagggtaattttgcatttgtaattttaaaaaatgctttc ttcttttaatatactttttgtttatcttatttctaatac tttccctaatctctttctttcagggcaataatgatacaat gtatcatgcctctttgcaccattctaaagaataacagtga taatttctgggttaaggcaatagcaatatttctgcatata aatatttctgcatataaattgtaactgatgtaagaggttt catattgctaatagcagctacaatccagctaccattctgc ttttatttatggttgggataaggctggattattctgagt ccaagctaggccctttgctaatcatgttcatacccttta cttctatgactgtagCAAGGATATGGGCTCACTGAGACT |
| SEQ ID NO.: 6 | Luci-IVSΔ-Luci in construct Con6 | TCCATCTGCCAGGTATCAGGgtgagtctatgggaccccttg atgttttctttcccttcttttctatggttaagttcatgt catagggaaggggagaagtaacagggtacacatattgacca aatcagggtaattttgcatttgtaattttaaaaaatgctt tcttcttttaatatactttttgtttatcttatttctaat actttccctaatctctttctttcagggcaataatgataca atgtatcatgcctctttgcaccattctaaagaataacagt gataatttctgggttaaggcaatagcaatatttctgcata taaatatttctgcatataaattgtaactgatgtaagaggt ttcatattgctaatagcagctacaatccagctaccattct gcttttatttatggttgggataaggctggattattctga gtccaagctaggccctttgctaatcatgttcataccgtg actgtgtgtatgcacagCAAGGATATGGGCTCACTGAGAC T |

TABLE 5-continued

Description and associated sequences. Exon sequence is in uppercase letters and intron sequence in in lowercase letters unless otherwise stated.

| SEQ ID NO. | Description | Sequence |
|---|---|---|
| SEQ ID NO.: 7 | Luci-IVSΔ-Luci in construct Con7 | ATCTGCCAGGTATCAGGgtgagtctatgggacccttgatgttttctttcccttcttttctatggttaagttcatgtcataggaaggggagaagtaacagggtacacatattgaccaaatcagggtaattttgcatttgtaattttaaaaaatgctttcttcttttaatatactttttttgtttatcttatttctaatactttccctaatctctttctttcagggcaataatgatacaatgtatcatgcctctttgcaccattctaaagaataacagtgataatttctgggttaaggcaatagcaatatttctgcatataaatatttctgcatataaattgtaactgatgtaagaggttcatattgctaatagcagctacaatccagctaccattctgcttttatttatggttgggataaggctggattattctgagtccaagctaggcccttttgctaatcatgttcataccattgtatcgcagccaatagCAAGGATATGGGCTCACTGAGACT |
| SEQ ID NO.: 8 | DHFR exon 2 with flanking intronic sequence | gagtaacgctgtttctctaacttgtagGAATGAATTCAGATATTTCCAGAGAATGACCACAACCCTCTTCAGTAGAAGgtaatgtg |
| SEQ ID NO.: 9 | Theophylline aptamer | ggcgataccagccgaaaggcccttggcagcgtc |
| SEQ ID NO.: 10 | Xpt-guanine aptamer | cactcatataatcgcgtggatatggcacgcaagtttctaccgggcaccgtaaatgtccgactatgggtg |
| SEQ ID NO.: 11 | Ydh1-Guanine aptamer | ttgtataaccctcaataatatggtttgagggtgtctaccaggaaccgtaaaatcctgactacaa |
| SEQ ID NO.: 12 | Ydh1-Adenine aptamer | ttgtataaccctcaataatatggtttgagggtgtctaccaggaaccgtaaaatcctgattacaa |
| SEQ ID NO.: 13 | addA-Guanine aptamer | tcatataatcctaatgatatggtttgggagtttctaccaagagccttaaactcttgactatga |
| SEQ ID NO.: 14 | addA-Adenine aptamer | tcatataatcctaatgatatggtttgggagtttctaccaagagccttaaactcttgattatga |
| SEQ ID NO.: 15 | xpt-G17 riboswitch The aptamer (SEQ ID NO: 65) is underlined and the stem is double underlined. A modified DHFR exon 2 is in capital letters. | gtgagtctatgggacccttgatgttttctttcccttcttttctatggttaagttcatgtcataggaaggggagaagtaacagggtacacatattgaccaaatcagggtaattttgcatttgtaattttaaaaaatgctttcttcttttaatatactttttttgtttatcttatttctaatactttccctaatctctttctttcagggcaataatgatacaatgtatcatgccgagtaacgctgtttctctaacttgtagGAATGAATTCAGATATTTCCAGAGAATGAAAAAAAAATCTTCAGTAGAAG<u>gtaatgtataa</u><u>tcgcgtggatatggcacgcaagtttctaccgggcaccgta</u><u>aatgtccgact</u>acattacgcaccattctaaagaataacagtgataatttctgggttaaggcaatagcaatatttctgcataaatatttctgcatataaattgtaactgatgtaagaggtttcatattgctaatagcagctacaatccagctaccattctgcttttatttatggttgggataaggctggattattctgagtccaagctaggcccttttgctaatcatgttcataccctcttatcttcctcccacag |
| SEQ ID NO.: 16 | xpt-G17-IR-1 | gtgagtctatgggacccttgatgttttctttccctgctcaaatcagggtaattttgcatttgtaattttaaaaaatgcttcttcttttaatatactttttttgtttatcttatttctaatactttccctaatctctttctttcagggcaataatgatacaatgtatcatgccgagtaacgctgtttctctaacttgtagGAATGAATTCAGATATTTCCAGAGAATGAAAAAAAAATCTTCAGTAGAAGgtaatgtataatcgcgtggatatggcacgcaagtttctaccgggcaccgtaaatgtccgactacattacgcaccattctaaagaataacagtgataatttctgggttaaggcaatagcaatatttctgcatataaatatttctgcatataaattgtaactgatgtaagaggtttcatattgctaatagcagctacaatccagctaccattctgcttttatttatggttgggataaggctggattattctgagtccaagctaggcccttttgctaatcatgttcataccctcttatcttcctcccacag |
| SEQ ID NO.: 17 | xpt-G17-IR-2 | gtgagtctatgggacccttgatgttttctttccctgctcttcagggcaataatgatacaatgtatcatgccgagtaacgctgtttctctaacttgtagGAATGAATTCAGATATTTCCA |

TABLE 5-continued

Description and associated sequences. Exon sequence is in uppercase letters and intron sequence in in lowercase letters unless otherwise stated.

| SEQ ID NO. | Description | Sequence |
|---|---|---|
| | | GAGAATGAAAAAAAAATCTTCAGTAGAAGgtaatgtataa<br>tcgcgtggatatggcacgcaagtttctaccgggcaccgta<br>aatgtccgactacattacgcaccattctaaagaataacag<br>tgataatttctgggttaaggcaatagcaatatttctgcat<br>ataaatatttctgcatataaattgtaactgatgtaagagg<br>tttcatattgctaatagcagctacaatccagctaccattc<br>tgcttttattttatggttgggataaggctggattattctg<br>agtccaagctaggccttttgctaatcatgttcatacctc<br>ttatcttcctcccacag |
| SEQ ID NO.: 18 | xpt-G17-IR-3 | gtgagtctatgggaccttgatgttttctttcccccttctt<br>ttctatggttaagttcatgtgctcaaatcagggtaatttt<br>gcatttgtaattttaaaaaatgctttcttcttttaatata<br>cttttttgtttatcttatttctaatactttccctaatctc<br>tttctttcagggcaataatgatacaatgtatcatgccgag<br>taacgctgtttctctaacttgtagGAATGAATTCAGATAT<br>TCCAGAGAATGAAAAAAAAATCTTCAGTAGAAGgtaatg<br>tataatcgcgtggatatggcacgcaagtttctaccgggca<br>ccgtaaatgtccgactacattacgcaccattctaaagaat<br>aacagtgataatttctgggttaaggcaatagcaatatttc<br>tgcatataaatatttctgcatataaattgtaactgatgta<br>agaggtttcatattgctaatagcagctacaatccagctac<br>cattctgcttttattttatggttgggataaggctggatta<br>ttctgagtccaagctaggccttttgctaatcatgttcat<br>acctcttatcttcctcccacag |
| SEQ ID NO.: 19 | xpt-G17-IR-4 | gtgagtctatgggaccttgatgttttctttcccccttctt<br>ttctatggttaagttcatgtgctctttcagggcaataatg<br>atacaatgtatcatgccgagtaacgctgtttctctaactt<br>gtagGAATGAATTCAGATATTCCAGAGAATGAAAAAAAA<br>ATCTTCAGTAGAAGgtaatgtataatcgcgtggatatggc<br>acgcaagtttctaccgggcaccgtaaatgtccgactacat<br>tacgcaccattctaaagaataacagtgataatttctgggt<br>taaggcaatagcaatatttctgcatataaatatttctgca<br>tataaattgtaactgatgtaagaggtttcatattgctaat<br>agcagctacaatccagctaccattctgcttttattttatg<br>gttgggataaggctggattattctgagtccaagctaggcc<br>ttttgctaatcatgttcatacctcttatcttcctcccac<br>ag |
| SEQ ID NO.: 20 | xpt-G17-IR-5 | gtgagtctatgggaccttgatgttttctttcccccttctt<br>ttctatggttaagttcatgtcataggaaggggagaagtaa<br>cagggtactgctcaaatcagggtaattttgcatttgtaat<br>tttaaaaaatgctttcttcttttaatatacttttttgttt<br>atcttatttctaatactttccctaatctctttctttcagg<br>gcaataatgatacaatgtatcatgccgagtaacgctgttt<br>ctctaacttgtagGAATGAATTCAGATATTCCAGAGAAT<br>GAAAAAAAAATCTTCAGTAGAAGgtaatgtataatcgcgt<br>ggatatggcacgcaagtttctaccgggcaccgtaaatgtc<br>cgactacattacgcaccattctaaagaataacagtgataa<br>tttctgggttaaggcaatagcaatatttctgcatataaat<br>atttctgcatataaattgtaactgatgtaagaggtttcat<br>attgctaatagcagctacaatccagctaccattctgcttt<br>tattttatggttgggataaggctggattattctgagtcca<br>agctaggccttttgctaatcatgttcatacctcttatct<br>tcctcccacag |
| SEQ ID NO.: 21 | xpt-G17-IR-6 | gtgagtctatgggaccttgatgttttctttcccccttctt<br>ttctatggttaagttcatgtcataggaaggggagaagtaa<br>cagggtactgctctttcagggcaataatgatacaatgtat<br>catgccgagtaacgctgtttctctaacttgtagGAATGAA<br>TTCAGATATTCCAGAGAATGAAAAAAAAATCTTCAGTAG<br>AAGgtaatgtataatcgcgtggatatggcacgcaagtttc<br>taccgggcaccgtaaatgtccgactacattacgcaccatt<br>ctaaagaataacagtgataatttctgggttaaggcaatag<br>caatatttctgcatataaatatttctgcatataaattgta<br>actgatgtaagaggtttcatattgctaatagcagctacaa<br>tccagctaccattctgcttttattttatggttgggataag<br>gctggattattctgagtccaagctaggccttttgctaat<br>catgttcatacctcttatcttcctcccacag |

TABLE 5-continued

Description and associated sequences. Exon
sequence is in uppercase letters and intron
sequence in in lowercase letters unless
otherwise stated.

| SEQ ID NO. | Description | Sequence |
|---|---|---|
| SEQ ID NO.: 22 | xpt-G17-IR-7 | gtgagtctatgggacccttgatgttttctttcccttctt<br>ttctatggttaagttcatgtcataggaagtgctcaaatca<br>gggtaattttgcatttgtaattttaaaaaatgctttcttc<br>ttttaatatacttttttgtttatcttatttctaatacttt<br>ccctaatctcttctttcagggcaataatgatacaatgta<br>tcatgccgagtaacgctgtttctctaacttgtagGAATGA<br>ATTCAGATATTTCCAGAGAATGAAAAAAAAATCTTCAGTA<br>GAAGgtaatgtataatcgcgtggatatggcacgcaagttt<br>ctaccgggcaccgtaaatgtccgactacattacgccat<br>tctaaagaataacagtgataatttctgggttaaggcaata<br>gcaatatttctgcatataaatatttctgcatataaattgt<br>aactgatgtaagaggtttcatattgctaatagcagctaca<br>atccagctaccattctgcttttattttatggttgggataa<br>ggctggattattctgagtccaagctaggcccttttgctaa<br>tcatgttcatacctcttatcttcctcccacag |
| SEQ ID NO.: 23 | xpt-G17-IR-8 | gtgagtctatgggacccttgatgttttctttcccttctt<br>ttctatggttaagttcatgtcataggaagtgctctttcag<br>ggcaataatgatacaatgtatcatgccgagtaacgctgtt<br>tctctaacttgtagGAATGAATTCAGATATTTCCAGAGAA<br>TGAAAAAAAAATCTTCAGTAGAAGgtaatgtataatcgcg<br>tggatatggcacgcaagtttctaccgggcaccgtaaatgt<br>ccgactacattacgccattctaaagaataacagtgata<br>atttctgggttaaggcaatagcaatatttctgcatataaa<br>tatttctgcatataaattgtaactgatgtaagaggtttca<br>tattgctaatagcagctacaatccagctaccattctgctt<br>ttattttatggtgggataaggctggattattctgagtcc<br>aagctaggcccttttgctaatcatgttcatacctcttatc<br>ttcctcccacag |
| SEQ ID NO.: 24 | xpt-G17-IR-9 | gtgagtctatgggacccttgatgttttctttcccttctt<br>ttctatggttaagttcatgtcataggaaggggagaagtaa<br>cagggtacacatattgaccaaatcagggtaattttgcatt<br>tgtaattttaaaaaatgctttcttcttttaatatactttt<br>ttgtttatcttatttctaatactttccctaatctcttct<br>ttcagggcaataatgatacaatgtatcatgccgagtaacg<br>ctgtttctctaacttgtagGAATGAATTCAGATATTTCCA<br>GAGAATGAAAAAAAAATCTTCAGTAGAAGgtaatgtataa<br>tcgcgtggatatggcacgcaagtttctaccgggcaccgta<br>aatgtccgactacattacgccattctaaagaataacag<br>tgataatttctgggttaaggcaatagctgctgctggatta<br>ttctgagtccaagctaggcccttttgctaatcatgttcat<br>acctcttatcttcctcccacag |
| SEQ ID NO.: 25 | xpt-G17-IR-10 | gtgagtctatgggacccttgatgttttctttcccttctt<br>ttctatggttaagttcatgtcataggaaggggagaagtaa<br>cagggtacacatattgaccaaatcagggtaattttgcatt<br>tgtaattttaaaaaatgctttcttcttttaatatactttt<br>ttgtttatcttatttctaatactttccctaatctcttct<br>ttcagggcaataatgatacaatgtatcatgccgagtaacg<br>ctgtttctctaacttgtagGAATGAATTCAGATATTTCCA<br>GAGAATGAAAAAAAAATCTTCAGTAGAAGgtaatgtataa<br>tcgcgtggatatggcacgcaagtttctaccgggcaccgta<br>aatgtccgactacattacgccattctaaagaataacag<br>tgataatttctgggttaaggcaatagcaatatttctgcat<br>ataaatatttctgcatataaattgtaactgatgtaagagg<br>tttcatattgctaatagcagctacaatccagctgctgctg<br>gattattctgagtccaagctaggcccttttgctaatcatg<br>ttcatacctcttatcttcctcccacag |
| SEQ ID NO.: 26 | xpt-G17-IR-11 | gtgagtctatgggacccttgatgttttctttcccttctt<br>ttctatggttaagttcatgtcataggaaggggagaagtaa<br>cagggtacacatattgaccaaatcagggtaattttgcatt<br>tgtaattttaaaaaatgctttcttcttttaatatactttt<br>ttgtttatcttatttctaatactttccctaatctcttct<br>ttcagggcaataatgatacaatgtatcatgccgagtaacg<br>ctgtttctctaacttgtagGAATGAATTCAGATATTTCCA<br>GAGAATGAAAAAAAAATCTTCAGTAGAAGgtaatgtataa<br>tcgcgtggatatggcacgcaagtttctaccgggcaccgta<br>aatgtccgactacattacgccattctaaagaataacag<br>tgataatttctgggttaaggcaatagctgctgaggtttca |

TABLE 5-continued

Description and associated sequences. Exon sequence is in uppercase letters and intron sequence in in lowercase letters unless otherwise stated.

| SEQ ID NO. | Description | Sequence |
|---|---|---|
| | | tattgctaatagcagctacaatccagctaccattctgctt<br>ttattttatggttgggataaggctggattattctgagtcc<br>aagctaggccctttgctaatcatgttcatacctcttatc<br>ttcctcccacag |
| SEQ ID NO.: 27 | xpt-G17-IR-13 | gtgagtctatgggacccttgatgttttctttcccttctt<br>ttctatggttaagttcatgtcataggaaggggagaagtaa<br>cagggtacacatattgaccaaatcagggtaattttgcatt<br>tgtaattttaaaaaatgctttcttcttttaatatacttt<br>ttgtttatcttatttctaatactttccctaatctctttct<br>ttcagggcaataatgatacaatgtatcatgccgagtaacg<br>ctgtttctctaacttgtagGAATGAATTCAGATATTTCCA<br>GAGAATGAAAAAAAAATCTTCAGTAGAAGgtaatgtataa<br>tcgcgtggatatggcacgcaagtttctaccgggcaccgta<br>aatgtccgactacattacgcaccattctaaagaataacag<br>tgataatttctggttaaggcaatagctgctctaccattc<br>tgcttttattttatggttgggataaggctggattattctg<br>agtccaagctaggccctttgctaatcatgttcatacct<br>ttatcttcctcccacag |
| SEQ ID NO.: 28 | xpt-G17-IR-15 | gtgagtctatgggacccttgatgttttctttcccttctt<br>ttctatggttaagttcatgtcataggaaggggagaagtaa<br>cagggtacacatattgaccaaatcagggtaattttgcatt<br>tgtaattttaaaaaatgctttcttcttttaatatacttt<br>ttgtttatcttatttctaatactttccctaatctctttct<br>ttcagggcaataatgatacaatgtatcatgccgagtaacg<br>ctgtttctctaacttgtagGAATGAATTCAGATATTTCCA<br>GAGAATGAAAAAAAAATCTTCAGTAGAAGgtaatgtataa<br>tcgcgtggatatggcacgcaagtttctaccgggcaccgta<br>aatgtccgactacattacgcaccattctaaagaataacag<br>tgataatttctggttaaggcaatagctgctgcagctaca<br>atccagctaccattctgcttttattttatggttgggataa<br>ggctggattattctgagtccaagctaggccctttgctaa<br>tcatgttcatacctcttatcttcctcccacag |
| SEQ ID NO.: 29 | xpt-G17-2IR-1 | gtgagtctatgggacccttgatgttttctttccctgctca<br>aatcagggtaattttgcatttgtaattttaaaaaatgctt<br>tcttcttttaatatacttttttgtttatcttatttctaat<br>actttccctaatctctttctttcagggcaataatgataca<br>atgtatcatgccgagtaacgctgtttctctaacttgtagG<br>AATGAATTCAGATATTTCCAGAGAATGAAAAAAAAATCTT<br>CAGTAGAAGgtaatgtataatcgcgtggatatggcacgca<br>agtttctaccgggcaccgtaaatgtccgactacattacgc<br>accattctaaagaataacagtgataatttctggttaagg<br>caatagctgctgctggattattctgagtccaagctaggcc<br>ttttgctaatcatgttcatacctcttatcttcctcccac<br>ag |
| SEQ ID NO.: 30 | xpt-G17-2IR-2 | gtgagtctatgggacccttgatgttttctttccctgctca<br>aatcagggtaattttgcatttgtaattttaaaaaatgctt<br>tcttcttttaatatacttttttgtttatcttatttctaat<br>actttccctaatctctttctttcagggcaataatgataca<br>atgtatcatgccgagtaacgctgtttctctaacttgtagG<br>AATGAATTCAGATATTTCCAGAGAATGAAAAAAAAATCTT<br>CAGTAGAAGgtaatgtataatcgcgtggatatggcacgca<br>agtttctaccgggcaccgtaaatgtccgactacattacgc<br>accattctaaagaataacagtgataatttctggttaagg<br>caatagcaatatttctgcatataaatatttctgcatataa<br>attgtaactgatgtaagaggtttcatattgctaatagcag<br>ctacaatccagctgctgctggattattctgagtccaagct<br>aggccctttgctaatcatgttcatacctcttatcttcct<br>cccacag |
| SEQ ID NO.: 31 | xpt-G17-2IR-3 | gtgagtctatgggacccttgatgttttctttccctgctca<br>aatcagggtaattttgcatttgtaattttaaaaaatgctt<br>tcttcttttaatatacttttttgtttatcttatttctaat<br>actttccctaatctctttctttcagggcaataatgataca<br>atgtatcatgccgagtaacgctgtttctctaacttgtagG<br>AATGAATTCAGATATTTCCAGAGAATGAAAAAAAAATCTT<br>CAGTAGAAGgtaatgtataatcgcgtggatatggcacgca<br>agtttctaccgggcaccgtaaatgtccgactacattacgc<br>accattctaaagaataacagtgataatttctggttaagg |

TABLE 5-continued

Description and associated sequences. Exon
sequence is in uppercase letters and intron
sequence in in lowercase letters unless
otherwise stated.

| SEQ ID NO. | Description | Sequence |
|---|---|---|
| | | caatagctgctgaggtttcatattgctaatagcagctaca<br>atccagctaccattctgcttttatttatggttgggataa<br>ggctggattattctgagtccaagctaggcccttttgctaa<br>tcatgttcatacctcttatcttcctcccacag |
| SEQ ID NO.: 32 | xpt-G17-2IR-4 | gtgagtctatgggacccttgatgttttctttccctgctca<br>aatcagggtaattttgcatttgtaattttaaaaaatgctt<br>tcttcttttaatatacttttttgtttatcttatttctaat<br>actttccctaatctctttctttcagggcaataatgataca<br>atgtatcatgccgagtaacgctgtttctctaacttgtagG<br>AATGAATTCAGATATTTCCAGAGAATGAAAAAAAAATCTT<br>CAGTAGAAGgtaatgtataatcgcgtggatatggcacgca<br>agtttctaccgggcaccgtaaatgtccgactacattacgc<br>accattctaaagaataacagtgataatttctgggttaagg<br>caatagctgctctaccattctgcttttatttatggttgg<br>gataaggctggattattctgagtccaagctaggcccttttt<br>gctaatcatgttcatacctcttatcttcctcccacag |
| SEQ ID NO.: 33 | xpt-G17-2IR-5 | gtgagtctatgggacccttgatgttttctttccctgctca<br>aatcagggtaattttgcatttgtaattttaaaaaatgctt<br>tcttcttttaatatacttttttgtttatcttatttctaat<br>actttccctaatctctttctttcagggcaataatgataca<br>atgtatcatgccgagtaacgctgtttctctaacttgtagG<br>AATGAATTCAGATATTTCCAGAGAATGAAAAAAAAATCTT<br>CAGTAGAAGgtaatgtataatcgcgtggatatggcacgca<br>agtttctaccgggcaccgtaaatgtccgactacattacgc<br>accattctaaagaataacagtgataatttctgggttaagg<br>caatagctgctgcagctacaatccagctaccattctgctt<br>ttatttatggttgggataaggctggattattctgagtcc<br>aagctaggcccttttgctaatcatgttcatacctcttatc<br>ttcctcccacag |
| SEQ ID NO.: 34 | xpt-G17-2IR-6 | gtgagtctatgggacccttgatgttttctttcccttctt<br>ttctatggttaagttcatgtgctcaaatcagggtaatttt<br>gcatttgtaattttaaaaaatgctttcttcttttaatata<br>cttttttgtttatcttatttctaatactttccctaatctc<br>tttctttcagggcaataatgatacaatgtatcatgccgag<br>taacgctgtttctctaacttgtagGAATGAATTCAGATAT<br>TTCCAGAGAATGAAAAAAAAATCTTCAGTAGAAGgtaatg<br>tataatcgcgtggatatggcacgcaagtttctaccgggca<br>ccgtaaatgtccgactacattacgcaccattctaaagaat<br>aacagtgataatttctgggttaaggcaatagctgctgctg<br>gattattctgagtccaagctaggcccttttgctaatcatg<br>ttcatacctcttatcttcctcccacag |
| SEQ ID NO.: 35 | xpt-G17-2IR-7 | gtgagtctatgggacccttgatgttttctttcccttctt<br>ttctatggttaagttcatgtgctcaaatcagggtaatttt<br>gcatttgtaattttaaaaaatgctttcttcttttaatata<br>cttttttgtttatcttatttctaatactttccctaatctc<br>tttctttcagggcaataatgatacaatgtatcatgccgag<br>taacgctgtttctctaacttgtagGAATGAATTCAGATAT<br>TTCCAGAGAATGAAAAAAAAATCTTCAGTAGAAGgtaatg<br>tataatcgcgtggatatggcacgcaagtttctaccgggca<br>ccgtaaatgtccgactacattacgcaccattctaaagaat<br>aacagtgataatttctgggttaaggcaatagcaatatttc<br>tgcatataaatatttctgcatataaattgtaactgatgta<br>agaggtttcatattgctaatagcagctacaatccagctgc<br>tgctggattattctgagtccaagctaggcccttttgctaa<br>tcatgttcatacctcttatcttcctcccacag |
| SEQ ID NO.: 36 | xpt-G17-2IR-8 | gtgagtctatgggacccttgatgttttctttcccttctt<br>ttctatggttaagttcatgtgctcaaatcagggtaatttt<br>gcatttgtaattttaaaaaatgctttcttcttttaatata<br>cttttttgtttatcttatttctaatactttccctaatctc<br>tttctttcagggcaataatgatacaatgtatcatgccgag<br>taacgctgtttctctaacttgtagGAATGAATTCAGATAT<br>TTCCAGAGAATGAAAAAAAAATCTTCAGTAGAAGgtaatg<br>tataatcgcgtggatatggcacgcaagtttctaccgggca<br>ccgtaaatgtccgactacattacgcaccattctaaagaat<br>aacagtgataatttctgggttaaggcaatagctgctgagg<br>tttcatattgctaatagcagctacaatccagctaccattc<br>tgcttttatttatggttgggataaggctggattattctg |

TABLE 5-continued

Description and associated sequences. Exon sequence is in uppercase letters and intron sequence in in lowercase letters unless otherwise stated.

| SEQ ID NO. | Description | Sequence |
|---|---|---|
|  |  | agtccaagctaggcccttttgctaatcatgttcatacctc<br>ttatcttcctcccacag |
| SEQ ID NO.: 37 | xpt-G17-2IR-9 | gtgagtctatgggacccttgatgttttctttcccttctt<br>ttctatggttaagttcatgtgctcaaatcagggtaatttt<br>gcatttgtaattttaaaaaatgctttcttcttttaatata<br>cttttttgtttatcttatttctaatactttccctaatctc<br>tttctttcagggcaataatgatacaatgtatcatgccgag<br>taacgctgtttctctaacttgtagGAATGAATTCAGATAT<br>TTCCAGAGAATGAAAAAAAAATCTTCAGTAGAAGgtaatg<br>tataatcgcgtggatatggcacgcaagtttctaccgggca<br>ccgtaaatgtccgactacattacgcaccattctaaagaat<br>aacagtgataatttctgggttaaggcaatagctgctctac<br>cattctgcttttattttatggttgggataaggctggatta<br>ttctgagtccaagctaggcccttttgctaatcatgttcat<br>acctcttatcttcctcccacag |
| SEQ ID NO.: 38 | xpt-G17-2IR-10 | gtgagtctatgggacccttgatgttttctttcccttctt<br>ttctatggttaagttcatgtgctcaaatcagggtaatttt<br>gcatttgtaattttaaaaaatgctttcttcttttaatata<br>cttttttgtttatcttatttctaatactttccctaatctc<br>tttctttcagggcaataatgatacaatgtatcatgccgag<br>taacgctgtttctctaacttgtagGAATGAATTCAGATAT<br>TTCCAGAGAATGAAAAAAAAATCTTCAGTAGAAGgtaatg<br>tataatcgcgtggatatggcacgcaagtttctaccgggca<br>ccgtaaatgtccgactacattacgcaccattctaaagaat<br>aacagtgataatttctgggttaaggcaatagctgctgcag<br>ctacaatccagctaccattctgcttttattttatggttgg<br>gataaggctggattattctgagtccaagctaggccctttt<br>gctaatcatgttcatacctcttatcttcctcccacag |
| SEQ ID NO.: 39 | xpt-G17-2IR-11 | gtgagtctatgggacccttgatgttttctttccctgctct<br>ttcagggcaataatgatacaatgtatcatgccgagtaacg<br>ctgtttctctaacttgtagGAATGAATTCAGATATTTCCA<br>GAGAATGAAAAAAAAATCTTCAGTAGAAGgtaatgtataa<br>tcgcgtggatatggcacgcaagtttctaccgggcaccgta<br>aatgtccgactacattacgcaccattctaaagaataacag<br>tgataatttctgggttaaggcaatagctgctgctggatta<br>ttctgagtccaagctaggcccttttgctaatcatgttcat<br>acctcttatcttcctcccacag |
| SEQ ID NO.: 40 | xpt-G17-2IR-12 | gtgagtctatgggacccttgatgttttctttccctgctct<br>ttcagggcaataatgatacaatgtatcatgccgagtaacg<br>ctgtttctctaacttgtagGAATGAATTCAGATATTTCCA<br>GAGAATGAAAAAAAAATCTTCAGTAGAAGgtaatgtataa<br>tcgcgtggatatggcacgcaagtttctaccgggcaccgta<br>aatgtccgactacattacgcaccattctaaagaataacag<br>tgataatttctgggttaaggcaatagctgctctaccattc<br>tgcttttattttatggtgggataaggctggattattctg<br>agtccaagctaggcccttttgctaatcatgttcatacctc<br>ttatcttcctcccacag |
| SEQ ID NO.: 41 | xpt-G17-2IR-13 | gtgagtctatgggacccttgatgttttctttcccttctt<br>ttctatggttaagttcatgtgctctttcagggcaataatg<br>atacaatgtatcatgccgagtaacgctgtttctctaactt<br>gtagGAATGAATTCAGATATTTCCAGAGAATGAAAAAAAA<br>ATCTTCAGTAGAAGgtaatgtataatcgcgtggatatggc<br>acgcaagtttctaccgggcaccgtaaatgtccgactacat<br>tacgcaccattctaaagaataacagtgataatttctgggt<br>taaggcaatagctgctgctggattattctgagtccaagct<br>aggcccttttgctaatcatgttcatacctcttatcttcct<br>cccacag |
| SEQ ID NO.: 42 | xpt-G17-2IR-14 | gtgagtctatgggacccttgatgttttctttcccttctt<br>ttctatggttaagttcatgtgctctttcagggcaataatg<br>atacaatgtatcatgccgagtaacgctgtttctctaactt<br>gtagGAATGAATTCAGATATTTCCAGAGAATGAAAAAAAA<br>ATCTTCAGTAGAAGgtaatgtataatcgcgtggatatggc<br>acgcaagtttctaccgggcaccgtaaatgtccgactacat<br>tacgcaccattctaaagaataacagtgataatttctgggt<br>taaggcaatagctgctctaccattctgcttttattttatg<br>gttgggataaggctggattattctgagtccaagctaggcc |

TABLE 5-continued

Description and associated sequences. Exon
sequence is in uppercase letters and intron
sequence in in lowercase letters unless
otherwise stated.

| SEQ ID NO. | Description | Sequence |
|---|---|---|
|  |  | cttttgctaatcatgttcatacctcttatcttcctcccac<br>ag |
| SEQ ID NO.: 43 | xpt-G17-2IR-15 | gtgagtctatgggacccttgatgttttctttcccttctt<br>ttctatggttaagttcatgtcataggaaggggagaagtaa<br>cagggtactgctctttcagggcaataatgatacaatgtat<br>catgccgagtaacgctgtttctctaacttgtagGAATGAA<br>TTCAGATATTTCCAGAGAATGAAAAAAAAATCTTCAGTAG<br>AAGgtaatgtataatcgcgtggatatggcacgcaagtttc<br>taccgggcaccgtaaatgtccgactacattacgcaccatt<br>ctaaagaataacagtgataatttctgggttaaggcaatag<br>ctgctgctggattattctgagtccaagctaggcccttttg<br>ctaatcatgttcatacctcttatcttcctcccacag |
| SEQ ID NO.: 44 | xpt-G17-2IR-16 | gtgagtctatgggacccttgatgttttctttcccttctt<br>ttctatggttaagttcatgtcataggaaggggagaagtaa<br>cagggtactgctctttcagggcaataatgatacaatgtat<br>catgccgagtaacgctgtttctctaacttgtagGAATGAA<br>TTCAGATATTTCCAGAGAATGAAAAAAAAATCTTCAGTAG<br>AAGgtaatgtataatcgcgtggatatggcacgcaagtttc<br>taccgggcaccgtaaatgtccgactacattacgcaccatt<br>ctaaagaataacagtgataatttctgggttaaggcaatag<br>ctgctctaccattctgcttttattttatggttgggataag<br>gctggattattctgagtccaagctaggccccttttgctaat<br>catgttcatacctcttatcttcctcccacag |
| SEQ ID NO.: 45 | xpt-G17-3ssC-1 | gtgagtctatgggacccttgatgttttctttcccttctt<br>ttctatggttaagttcatgtcataggaaggggagaagtaa<br>cagggtacacatattgaccaaatcagggtaattttgcatt<br>tgtaattttaaaaaatgctttcttcttttaatatacttttt<br>ttgtttatcttatttctaatactttccctaatctctttct<br>ttcagggcaataatgatacaatgtatcatgccgagtaacg<br>ctgtttctctaacttccccGAATGAATTCAGATATTTCCA<br>GAGAATGAAAAAAAAATCTTCAGTAGAAGgtaatgtataa<br>tcgcgtggatatggcacgcaagtttctaccgggcaccgta<br>aatgtccgactacattacgcaccattctaaagaataacag<br>tgataatttctgggttaaggcaatagcaatatttctgcat<br>ataaatatttctgcatataaattgtaactgatgtaagagg<br>tttcatattgctaatagcagctacaatccagctaccattc<br>tgcttttattttatggttgggataaggctggattattctg<br>agtccaagctaggccccttttgctaatcatgttcatacctc<br>ttatcttcctcccacag |
| SEQ ID NO.: 46 | xpt-G15 riboswitch | gtgagtctatgggacccttgatgttttctttcccttctt<br>ttctatggttaagttcatgtcataggaaggggagaagtaa<br>cagggtacacatattgaccaaatcagggtaattttgcatt<br>tgtaattttaaaaaatgctttcttcttttaatatacttttt<br>ttgtttatcttatttctaatactttccctaatctctttct<br>ttcagggcaataatgatacaatgtatcatgccgagtaacg<br>ctgtttctctaacttgtagGAATGAATTCAGATATTTCCA<br>GAGAATGAAAAAAAAATCTTCAGTAGAAGgtaatgtgtat<br>aatcgcgtggatatggcacgcaagtttctaccgggcaccg<br>taaatgtccgactacacattacgcaccattctaaagaata<br>acagtgataatttctgggttaaggcaatagcaatatttct<br>gcatataaatatttctgcatataaattgtaactgatgtaa<br>gaggtttcatattgctaatagcagctacaatccagctacc<br>attctgcttttattttatggttgggataaggctggattat<br>tctgagtccaagctaggccccttttgctaatcatgttcata<br>cctcttatcttcctcccacag |
| SEQ ID NO.: 47 | DHFR WildType 5'<br>single-strand | gagtaacgctgtttctctaacttgtagGAATGAATTCAGA<br>TATTTCCAGAGAATGACCACAACCTCTTCAGTAGAAGgta<br>atgtg |
| SEQ ID NO.: 48 | DHFR 5' single-<br>strandC | gagtaacgctgtttctctaacttgtagGAATGAATTCAGA<br>TATTTCCAGAGAATGACCACAACCTCTTCAGTAGAAGccc<br>ctgtg |
| SEQ ID NO.: 49 | DHFR-Con1 5'<br>single-strand | gagtaacgctgtttctctaacttgtagGAATGAATTCAGA<br>TATTTCCAGAGAATGACCACAACCTCTTCAGTAGAGGgtg<br>agttg |

TABLE 5-continued

Description and associated sequences. Exon sequence is in uppercase letters and intron sequence in in lowercase letters unless otherwise stated.

| SEQ ID NO. | Description | Sequence |
|---|---|---|
| SEQ ID NO.: 50 | DHFR-Con4 5' single-strand | gagtaacgctgtttctctaacttgtagGAATGAATTCAGA TATTTCCAGAGAATGACCACAACCTCTTCAGTAGGAGgtg tggtg |
| SEQ ID NO.: 51 | DHFR WildType mtSRp40 | gagtaacgctgtttctctaacttgtagGAATGAATTCAGA TATTTCCAGAGAATGAAAAAAAAATCTTCAGTAGAAGgta atgtg |
| SEQ ID NO.: 52 | DHFR WildType strongSC35 | gagtaacgctgtttctctaacttgtagGAATGGCCCCTGA TATTTCCAGAGAATGACCACAACCTCTTCAGTAGAAGgta atgtg |
| SEQ ID NO.: 53 | DHFR WildType SC35hnRNPA1 | gagtaacgctgtttctctaacttgtagGAATGTAGGGAGA TATTTCCAGAGAATGACCACAACCTCTTCAGTAGAAGgta atgtg |
| SEQ ID NO.: 54 | DHFR-Con1 5' single-strand HP15 | gagtaacgctgtttctctaacttgtagGAATGAATTCAGA TATTTCCAGAGAATGACCACAACCTCTTCAGTAGGGgtg agttggcgaaagccaactcaccctct |
| SEQ ID NO.: 55 | DHFR-Con1 5' single-strand HP15x | gagtaacgctgtttctctaacttgtagGAATGAATTCAGA TATTTCCAGAGAATGACCACAACCTCTTCAGTAGGGgtg agttggcgaaaaacagcataaagtat |
| SEQ ID NO.: 56 | DHFR WildType mtSRp40 HP 15 | gagtaacgctgtttctctaacttgtagGAATGAATTCAGA TATTTCCAGAGAATGAAAAAAAAATCTTCAGTAGAAGgta atgtggcgaaagccacattaccttct |
| SEQ ID NO.: 57 | DHFR WildType mtSRp40 HP15X | gagtaacgctgtttctctaacttgtagGAATGAATTCAGA TATTTCCAGAGAATGAAAAAAAAATCTTCAGTAGAAGgta atgtggcgaaaaacagaactgagtat |
| SEQ ID NO.: 58 | Mutant DHFR-e2 (mtDHFR) | gagtaacgctgtttctctaacttgtagGAATGAATTCAGA TATTTCCAGAGAATGAAAAAAAAATCTTCAGTAGAAGgta atgt |
| SEQ ID NO.: 59 | Camk2d-e16 | gagtaacgctgtttctctaacttgtagTGAGCCCCAAACT ACTGTAATCCACAACCCTGACGGAAACAAGgtaatgt |
| SEQ ID NO.: 60 | Camk2d-e17 | gagtaacgctgtttctctaacttgtagGAGTCAACTGAGA GCTCAAACACCACCATTGAGGATGAAGACGTGAAAGgtaa tgt |
| SEQ ID NO.: 61 | MutWT1-e5 | gagtaacgctgtttctctaacttgtagAGTTGCTGCTGAG AGCTCCAGCTCAGTGAAATGGACAGAAGGGCAGAGCAAgt aatgt |
| SEQ ID NO :62 | SIRT1-e6 | tgtggtgtgttcaagaaacagaaatacttctttaataaag catatatatgttgtttgttttagGTTCCTTTGCAACAGC ATCTTGCCTGATTTGTAAATACAAAGTTGACTGTGAAGCT GTACGAGGAGATATTTTTAATCAGgtaatgt |
| SEQ ID NO. 63 | ENEEE synthetic exon | GagtaacgctgtttctctaacttgtagACAATCCTCGAAC CAAACAACCAAACAACCAAACAATCCTCGAACCAAACAAT CCTCGAACCAAACAATCCTCGAACCAAgtaatgt |
| SEQ ID NO. 64 | xpt-G15-double | GCCAAGAGGTTCCATCTGCCAGGTATCAGGgtgagtctatg ggacccttgatgttttctttcccttcttttctatggtta agttcatgtcataggaaggggagaagtaacagggtacaca tattgaccaaatcagggtaattttgcatttgtaattttaa aaaatgctttcttcttttaatatactttttttgtttatctt atttctaatactttccctaatctctttcttttcagggcaat aatgatacaatgtatcatgccgagtaacgctgtttctcta acttgtagGAATGAATTCAGATATTTCCAGAGAATGAAAA AAAAATCTTCAGTAGAAGgtaatgtgtataatcgcgtgga tatggcacgcaagtttctaccgggcaccgtaaatgtccga ctacacattacgcaccattctaaagaataacagtgataat ttctgggttaaggcaatagcaatatttctgcatataaata tttctgcatataaattgtaactgatgtaagaggtttcata ttgctaatagcagctacaatccagctaccattctgctttt attttatggtgggataaggctggattattctgagtccaa gctaggccctttttgctaatcatgttcatacctcttatctt |

TABLE 5-continued

Description and associated sequences. Exon sequence is in uppercase letters and intron sequence in in lowercase letters unless otherwise stated.

| SEQ ID NO. | Description | Sequence |
|---|---|---|
| | | cctcccacagCAAGGATATGGGCTCACTGAGACTACATCA GCTATTCTGATTACACCCGAGGGGATGATAAACCGGGCG CGGTCGGTAAAGTTGTTCCATTTTTTGAAGCGAAGGTTGT GGATCTGGATACCGGGAAAACGCTGGGCGTTAATCAAAGA GGCGAACTGTGTGTGAGAGGTCCTATGATTATGTCCGGTT ATGTAAACAATCCGGAAGCGACCAACGCCTTGATTGACAA GGATGGATGGCTACATTCTGGAGACATAGCTTACTGGGAC GAAGACGAACACTTCTTCATCGTTGACCGCCTGAAGTCTC TGATTAAGTACAAAGGgtgagtctatgggacccttgatgt tttctttccccttcttttctatggttaagttcatgtcata ggaagggagaagtaacagggtacacatattgaccaaatc agggtaattttgcatttgtaattttaaaaaatgctttctt cttttaatatacttttttgtttatcttatttctaatactt tcctaatctctttcttcagggcaataatgatacaatgt atcatgccgagtaacgctgtttctctaacttgtagGAATG AATTCAGATATTTCCAGAGAATGAAAAAAAAATCTTCAGT AGAAGgtaatgtgtataatcgcgtggatatggcacgcaag tttctaccgggcaccgtaaatgtccgactacacattacgc accattctaaagaataacagtgataatttctgggttaagg caatagcaatatttctgcatataaatatttctgcatataa attgtaactgatgtaagaggtttcatattgctaatagcag ctacaatccagctaccattctgcttttatttatggttgg gataaggctggattattctgagtccaagctaggcccttt gctaatcatgttcatacctcttatcttcctcccacagCTA TCAGGTGGCTCCCGCTGAATTGGAATCCATCTTGCTCC |

---

The invention claimed is:

1. A polynucleotide cassette for the regulation of the expression of a target gene comprising:
   a. a riboswitch;
   b. an alternatively-spliced exon, flanked by a 5' intron and a 3' intron,
   wherein the riboswitch comprises (i) an effector region comprising a stem that includes the 5' splice site sequence of the 3' intron, and (ii) an aptamer;
   wherein the 5' splice site sequence of the 3' intron comprises the sequence (i) GTAATG, (ii) GTRAGT, wherein R can be A or G, (iii) GTAAGC, or (iv) GTGTGG; and
   wherein the alternatively-spliced exon comprises a stop codon that is in-frame with the target gene when the alternatively-spliced exon is spliced into the target gene mRNA.

2. The polynucleotide cassette of claim 1, wherein the 5' splice site sequence of the 3' intron comprises the sequence GTAATG.

3. The polynucleotide cassette of claim 1, wherein the 5' splice site sequence of the 3' intron comprises the sequence (i) GTRAGT, wherein R can be A or G, (ii) GTAAGC, or (iii) GTGTGG.

4. The polynucleotide cassette of claim 1, wherein the alternatively-spliced exon:
   a. is derived from exon 2 of the human dihydrofolate reductase gene, human Wilms tumor 1 exon 5, mouse calcium/calmodulin-dependent protein kinase II delta exon 16, or SIRT1 exon 6; or
   b. is synthetic.

5. The polynucleotide cassette of claim 1, wherein the alternatively-spliced exon has been modified by one or more of the group consisting of altering the sequence of an exon splice enhancer, altering the sequence of exon splice silencer, adding an exon splice enhancer, and adding an exon splice silencer.

6. The polynucleotide cassette of claim 1, wherein the aptamer binds a small molecule ligand.

7. The polynucleotide cassette of claim 1, wherein the 5' intron comprises a stop codon in-frame with the target gene.

8. The polynucleotide cassette of claim 1, wherein the 5' and 3' introns:
   a. are derived from an endogenous intron from the target gene;
   b. are exogenous to the target gene; or
   c. are derived from intron 2 of the human β-globin gene.

9. The polynucleotide cassette of claim 1, wherein the 5' and 3' introns are each independently from about 50 to about 300 nucleotides in length.

10. The polynucleotide cassette of claim 9, wherein the 5' and 3' introns are each independently from about 125 to about 240 nucleotides in length.

11. The polynucleotide cassette of claim 1, wherein the effector region stem is about 7 to about 20 base pairs in length.

12. The polynucleotide cassette of claim 11, wherein the effector region stem is 8 to 11 base pairs in length.

13. The polynucleotide cassette of claim 1, wherein the polynucleotide cassette comprises a sequence selected from the group consisting of SEQ ID NOs: 15, 16, 18, 20-22, 24-38, 45, and 46, wherein the aptamer sequence comprising TAATCGCGTGGATATGGCACGCAAGTTTC-TACCGGGCACCGTAAATGTCCGAC (SEQ ID NO:65) is replaced with a different aptamer sequence.

14. The polynucleotide cassette of claim 13, wherein the polynucleotide cassette comprises the sequence of SEQ ID NO:15, wherein the aptamer sequence comprising TAATCGCGTGGATATGGCACGCAAGTTTC-TACCGGGCACCGTAAATGTCCGAC (SEQ ID NO:65) is replaced with a different aptamer sequence.

15. The polynucleotide cassette of claim 13, wherein the polynucleotide cassette comprises the sequence of SEQ ID NO:46, wherein the aptamer sequence comprising TAATCGCGTGGATATGGCACGCAAGTTTC-TACCGGGCACCGTAAATGTCCGAC (SEQ ID NO:65) is replaced with a different aptamer sequence.

16. A recombinant polynucleotide comprising a target gene containing the polynucleotide cassette of claim 1.

17. The recombinant polynucleotide of claim 16, wherein the polynucleotide cassette is located in the protein coding sequence of the target gene.

18. A vector comprising a recombinant polynucleotide of claim 16.

19. The vector of claim 18, wherein the vector is a viral vector.

20. The vector of claim 19, wherein the viral vector is selected from the group consisting of adenoviral vector, adeno-associated virus vector, and lentiviral vector.

21. The vector of claim 18, wherein the vector is a non-viral vector.

22. A polynucleotide cassette for the regulation of the expression of a target gene comprising:
   a. a riboswitch;
   b. an alternatively-spliced exon, flanked by a 5' intron and a 3' intron,
   wherein the riboswitch comprises (i) an effector region comprising a stem that includes the 5' splice site sequence of the 3' intron, and (ii) an aptamer;
   wherein the alternatively-spliced exon comprises a stop codon that is in-frame with the target gene when the alternatively-spliced exon is spliced into the target gene mRNA; and
   wherein the alternatively-spliced exon comprises the exon sequence of any one of SEQ ID NOs: 47, 49, 51, 52, 59, 61, 62, or 63.

23. The polynucleotide cassette of claim 22, wherein the aptamer binds a small molecule ligand.

24. The polynucleotide cassette of claim 22, wherein the 5' intron comprises a stop codon in-frame with the target gene.

25. The polynucleotide cassette of claim 22, wherein the 5' and 3' introns:
   a. are derived from an endogenous intron from the target gene;
   b. are exogenous to the target gene; or
   c. are derived from intron 2 of the human β-globin gene.

26. The polynucleotide cassette of claim 22, wherein the 5' and 3' introns are each independently from about 50 to about 300 nucleotides in length.

27. The polynucleotide cassette of claim 22, wherein the 5' and 3' introns are each independently from about 125 to about 240 nucleotides in length.

28. The polynucleotide cassette of claim 22, wherein the effector region stem is about 7 to about 20 base pairs in length.

29. The polynucleotide cassette of claim 28, wherein the effector region stem is 8 to 11 base pairs in length.

30. A recombinant polynucleotide comprising a target gene containing the polynucleotide cassette of claim 22.

31. The recombinant polynucleotide of claim 30, wherein the polynucleotide cassette is located in the protein coding sequence of the target gene.

32. A vector comprising a recombinant polynucleotide of claim 30.

33. The vector of claim 32, wherein the vector is a viral vector.

34. The vector of claim 33, wherein the viral vector is selected from the group consisting of adenoviral vector, adeno-associated virus vector, and lentiviral vector.

35. The vector of claim 32, wherein the vector is a non-viral vector.

36. A method of modulating the expression of a target gene comprising:
   a. exposing a cell to the vector according to claim 18, and
   b. exposing the cell to a small molecule ligand that specifically binds the aptamer in an amount effective to induce expression of the target gene.

37. A method of modulating the expression of a target gene comprising:
   a. exposing a cell to the vector according to claim 32, and
   b. exposing the cell to a small molecule ligand that specifically binds the aptamer in an amount effective to induce expression of the target gene.

38. A method of modulating expression of a target gene in the eye of a mammal, the method comprising:
   a. introducing into the eye the vector according to claim 18; and
   b. providing to the mammal a small molecule ligand in an amount effective to induce expression of the target gene.

39. A method of modulating expression of a target gene in the eye of a mammal, the method comprising:
   a. introducing into the eye the vector according to claim 32; and
   b. providing to the mammal a small molecule ligand in an amount effective to induce expression of the target gene.

40. The method of claim 36, wherein the expression of the target gene is greater than about 5-fold higher or is greater than about 10-fold higher when the small molecule ligand is present than the expression levels when the small molecule ligand is absent.

41. The method of claim 36, wherein two or more of the polynucleotide cassettes are inserted into the target gene.

42. The method of claim 41, wherein the two or more polynucleotide cassettes comprise different aptamers that specifically bind to different small molecule ligands or wherein the two or more polynucleotide cassettes comprise the same aptamer.

43. The method of claim 38, wherein the vector is intended to be introduced into the eye by intraocular injection.

* * * * *

SEQUENCE LISTING

<160> NUMBER OF SEQ ID NOS: 120

<210> SEQ ID NO 1
<211> LENGTH: 539
<212> TYPE: DNA
<213> ORGANISM: Artificial Sequence
<220> FEATURE:
<223> OTHER INFORMATION: Luci-IVS-Luci in construct Con1 Human beta-globin intron 2 containing a deletion (IVS2) is in lowercase and flanking luciferase sequence is in uppercase.

<400> SEQUENCE: 1
gaggttccat ctgccaggta tcagggtgag tctatgggac ccttgatgtt ttctttcccc    60
ttcttttcta tggttaagtt catgtcatag gaagggggaga agtaacaggg tacacatatt   120
gaccaaatca gggtaatttt gcatttgtaa ttttaaaaaa tgctttcttc ttttaatata   180
cttttttgtt tatcttattt ctaatactt ccctaatctc tttctttcag ggcaataatg   240
atacaatgta tcatgcctct tgcaccatt ctaaagaata acagtgataa tttctgggtt   300
aaggcaatag caatatttct gcatataaat atttctgcat ataaattgta actgatgtaa   360
gaggtttcat attgctaata gcagctacaa tccagctacc attctgcttt tattttatgg   420
ttgggataag gctggattat tctgagtcca agctaggccc ttttgctaat catgttcata   480
cctcttatct tcctcccaca gcaaggatat gggctcactg agactacatc agctattct    539

<210> SEQ ID NO 2
<211> LENGTH: 521
<212> TYPE: DNA
<213> ORGANISM: Artificial Sequence
<220> FEATURE:
<223> OTHER INFORMATION: Luci-IVS-Luci in construct Con2

<400> SEQUENCE: 2

```
gattacaccc gaggggatg ataaagtaag cctatgggac ccttgatgtt ttcttttccc    60
ttcttttcta tggttaagtt catgtcatag gaaggggaga agtaacaggg tacacatatt   120
gaccaaatca gggtaatttt gcatttgtaa ttttaaaaaa tgctttcttc ttttaatata   180
cttttttgtt tatcttattt ctaatacttt ccctaatctc tttctttcag ggcaataatg   240
atacaatgta tcatgcctct ttgcaccatt ctaaagaata acagtgataa tttctgggtt   300
aaggcaatag caatatttct gcatataaat atttctgcat ataaattgta actgatgtaa   360
gaggtttcat attgctaata gcagctacaa tccagctacc attctgcttt tattttatgg   420
ttgggataag gctggattat tctgagtcca agctaggccc ttttgctaat catgttcata   480
cctcttatct tcctcccaca gccgggcgcg gtcggtaaag t                       521
```

<210> SEQ ID NO 3
<211> LENGTH: 510
<212> TYPE: DNA
<213> ORGANISM: Artificial Sequence
<220> FEATURE:
<223> OTHER INFORMATION: Luci-IVS-Luci in construct Con3

<400> SEQUENCE: 3

```
ttcttcgcca aaagcagtaa gtctatggga cccttgatgt tttctttccc cttcttttct    60
atggttaagt tcatgtcata ggaaggggag aagtaacagg gtacacatat tgaccaaatc   120
agggtaattt tgcatttgta attttaaaaa atgctttctt cttttaatat acttttttgt   180
ttatcttatt tctaatactt tccctaatct ctttctttca gggcaataat gatacaatgt   240
atcatgcctc tttgcaccat tctaaagaat aacagtgata atttctgggt taaggcaata   300
gcaatatttc tgcatataaa tatttctgca tataaattgt aactgatgta agaggtttca   360
tattgctaat agcagctaca atccagctac cattctgctt ttattttatg gttgggataa   420
ggctggatta ttctgagtcc aagctaggcc ttttgctaa tcatgttcat acctcttatc   480
ttcctcccac agctctgatt gacaaatacg                                    510
```

<210> SEQ ID NO 4
<211> LENGTH: 517
<212> TYPE: DNA
<213> ORGANISM: Artificial Sequence
<220> FEATURE:
<223> OTHER INFORMATION: Luci-IVS-Luci in construct Con4

<400> SEQUENCE: 4

```
aagagctgtt tctgaggagg tgtggctatg ggacccttga tgttttcttt ccccttcttt    60
tctatggtta agttcatgtc ataggaaggg gagaagtaac agggtacaca tattgaccaa   120
atcagggtaa ttttgcattt gtaattttaa aaaatgcttt cttcttttaa tacttttt    180
tgtttatctt atttctaata ctttccctaa tctctttctt tcagggcaat aatgatacaa   240
tgtatcatgc ctctttgcac cattctaaag aataacagtg ataatttctg ggttaaggca   300
atagcaatat ttctgcatat aaatatttct gcatataaat tgtaactgat gtaagaggtt   360
tcatattgct aatagcagct acaatccagc taccattctg cttttatttt atggttggga   420
taaggctgga ttattctgag tccaagctag gccttttgc taatcatgtt catacctctt   480
atcttcctcc cacagccttc aggattacaa gattcaa                            517
```

<210> SEQ ID NO 5
<211> LENGTH: 519

```
<212> TYPE: DNA
<213> ORGANISM: Artificial Sequence
<220> FEATURE:
<223> OTHER INFORMATION: Luci-IVS-Luci in construct Con5

<400> SEQUENCE: 5
catctgccag gtatcagggt gagtctatgg gacccttgat gttttctttc cccttctttt      60
ctatggttaa gttcatgtca taggaagggg agaagtaaca gggtacacat attgaccaaa     120
tcagggtaat tttgcatttg taattttaaa aaatgctttc ttcttttaat atactttttt     180
gtttatctta tttctaatac tttccctaat ctctttcttt cagggcaata atgatacaat     240
gtatcatgcc tctttgcacc attctaaaga ataacagtga taatttctgg gttaaggcaa     300
tagcaatatt tctgcatata aatatttctg catataaatt gtaactgatg taagaggttt     360
catattgcta atagcagcta caatccagct accattctgc ttttatttta tggttgggat     420
aaggctggat tattctgagt ccaagctagg ccctttttgct aatcatgttc atacccttta     480
cttctatgac tgtagcaagg atatgggctc actgagact                            519

<210> SEQ ID NO 6
<211> LENGTH: 521
<212> TYPE: DNA
<213> ORGANISM: Artificial Sequence
<220> FEATURE:
<223> OTHER INFORMATION: Luci-IVS-Luci in construct Con6

<400> SEQUENCE: 6
tccatctgcc aggtatcagg gtgagtctat gggacccttg atgttttctt tccccttctt      60
ttctatggtt aagttcatgt cataggaagg ggagaagtaa cagggtacac atattgacca     120
aatcagggta ttttgcatt tgtaatttta aaaaatgctt tcttcttta atatactttt      180 ttgtttatct tatttctaat actttcccta atctctttct ttcagggcaa taatgataca     240
atgtatcatg cctctttgca ccattctaaa gaataacagt gataatttct gggttaaggc     300
aatagcaata tttctgcata taatatattc tgcatataaa ttgtaactga tgtaagaggt     360
ttcatattgc taatagcagc tacaatccag ctaccattct gcttttattt tatggttggg     420
ataaggctgg attattctga gtccaagcta ggccctttttg ctaatcatgt tcataccgtg     480
actgtgtgta tgcacagcaa ggatatgggc tcactgagac t                          521

<210> SEQ ID NO 7
<211> LENGTH: 518
<212> TYPE: DNA
<213> ORGANISM: Artificial Sequence
<220> FEATURE:
<223> OTHER INFORMATION: Luci-IVS-Luci in construct Con7

<400> SEQUENCE: 7
atctgccagg tatcagggtg agtctatggg acccttgatg ttttctttcc cttcttttc      60 tatggttaag ttcatgtcat aggaagggga gaagtaacag ggtacacata ttgaccaaat     120
cagggtaatt ttgcatttgt aattttaaaa atgctttct tcttttaata cttttttg     180 tttatcttat ttctaatact ttccctaatc tctttcttc agggcaataa tgatacaatg     240
tatcatgcct ctttgcacca ttctaaagaa taacagtgat aatttctggg ttaaggcaat     300
agcaatattt ctgcatataa atatttctgc atataaattg taactgatgt aagaggtttc     360
atattgctaa tagcagctac aatccagcta ccattctgct tttattttat ggtgggata     420 aggctggatt attctgagtc caagctaggc cctttttgcta atcatgttca taccattgtg     480
```
atcgcagcca atagcaagga tatgggctca ctgagact                                518

<210> SEQ ID NO 8
<211> LENGTH: 85
<212> TYPE: DNA
<213> ORGANISM: Artificial Sequence
<220> FEATURE:
<223> OTHER INFORMATION: DHFR exon 2 with flanking intronic sequence

<400> SEQUENCE: 8
gagtaacgct gtttctctaa cttgtaggaa tgaattcaga tatttccaga gaatgaccac        60
aacctcttca gtagaaggta atgtg                                              85

<210> SEQ ID NO 9
<211> LENGTH: 33
<212> TYPE: DNA
<213> ORGANISM: Artificial Sequence
<220> FEATURE:
<223> OTHER INFORMATION: Theophylline aptamer

<400> SEQUENCE: 9
ggcgatacca gccgaaaggc ccttggcagc gtc                                     33

<210> SEQ ID NO 10
<211> LENGTH: 69
<212> TYPE: DNA
<213> ORGANISM: Artificial Sequence
<220> FEATURE:
<223> OTHER INFORMATION: Xpt-guanine aptamer

<400> SEQUENCE: 10
cactcatata atcgcgtgga tatggcacgc aagtttctac cgggcaccgt aaatgtccga        60
ctatgggtg                                                                69

<210> SEQ ID NO 11
<211> LENGTH: 63
<212> TYPE: DNA
<213> ORGANISM: Artificial Sequence
<220> FEATURE:
<223> OTHER INFORMATION: Ydhl-Guanine aptamer

<400> SEQUENCE: 11
ttgtataacc tcaataatat ggtttgaggg tgtctaccag gaaccgtaaa atcctgacta        60
caa                                                                      63

<210> SEQ ID NO 12
<211> LENGTH: 63
<212> TYPE: DNA
<213> ORGANISM: Artificial Sequence
<220> FEATURE:
<223> OTHER INFORMATION: Ydhl-Adenine aptamer

<400> SEQUENCE: 12
ttgtataacc tcaataatat ggtttgaggg tgtctaccag gaaccgtaaa atcctgatta        60
caa                                                                      63

<210> SEQ ID NO 13
<211> LENGTH: 63
<212> TYPE: DNA
<213> ORGANISM: Artificial Sequence
<220> FEATURE:
<223> OTHER INFORMATION: addA-Guanine aptamer

<400> SEQUENCE: 13
tcatataatc ctaatgatat ggtttgggag tttctaccaa gagccttaaa ctcttgacta       60
tga                                                                   63

<210> SEQ ID NO 14
<211> LENGTH: 63
<212> TYPE: DNA
<213> ORGANISM: Artificial Sequence
<220> FEATURE:
<223> OTHER INFORMATION: addA-Adenine aptamer

<400> SEQUENCE: 14
tcatataatc ctaatgatat ggtttgggag tttctaccaa gagccttaaa ctcttgatta       60
tga                                                                   63

<210> SEQ ID NO 15
<211> LENGTH: 617
<212> TYPE: DNA
<213> ORGANISM: Artificial Sequence
<220> FEATURE:
<223> OTHER INFORMATION: xpt-G17 riboswitch

<400> SEQUENCE: 15
gtgagtctat gggacccttg atgttttctt tccccttctt ttctatggtt aagttcatgt       60
cataggaagg ggagaagtaa cagggtacac atattgacca aatcaggta attttgcatt      120 tgtaatttta aaaatgctt tcttctttta atatactttt ttgtttatct tatttctaat      180
actttcccta atctctttct ttcagggcaa taatgataca atgtatcatg ccgagtaacg      240
ctgtttctct aacttgtagg aatgaattca gatatttcca gagaatgaaa aaaaaatctt      300
cagtagaagg taatgtataa tcgcgtggat atggcacgca agtttctacc gggcaccgta      360
aatgtccgac tacattacgc accattctaa agaataacag tgataatttc tgggttaagg      420
caatagcaat atttctgcat ataaatattt ctgcatataa attgtaactg atgtaagagg      480
tttcatattg ctaatagcag ctacaatcca gctaccattc tgcttttatt ttatggttgg      540
gataaggctg gattattctg agtccaagct aggccctttt gctaatcatg ttcatacctc      600
ttatcttcct cccacag                                                   617

<210> SEQ ID NO 16
<211> LENGTH: 557
<212> TYPE: DNA
<213> ORGANISM: Artificial Sequence
<220> FEATURE:
<223> OTHER INFORMATION: xpt-G17-IR-1

<400> SEQUENCE: 16
gtgagtctat gggacccttg atgttttctt tccctgctca aatcaggta attttgcatt       60 tgtaatttta aaaatgctt tcttctttta atatactttt ttgtttatct tatttctaat      120
actttcccta atctctttct ttcagggcaa taatgataca atgtatcatg ccgagtaacg      180
ctgtttctct aacttgtagg aatgaattca gatatttcca gagaatgaaa aaaaaatctt      240
cagtagaagg taatgtataa tcgcgtggat atggcacgca agtttctacc gggcaccgta      300
aatgtccgac tacattacgc accattctaa agaataacag tgataatttc tgggttaagg      360
caatagcaat atttctgcat ataaatattt ctgcatataa attgtaactg atgtaagagg      420
tttcatattg ctaatagcag ctacaatcca gctaccattc tgcttttatt ttatggttgg      480
gataaggctg gattattctg agtccaagct aggccctttt gctaatcatg ttcatacctc      540

```
ttatcttcct cccacag                                                    557
```

<210> SEQ ID NO 17
<211> LENGTH: 457
<212> TYPE: DNA
<213> ORGANISM: Artificial Sequence
<220> FEATURE:
<223> OTHER INFORMATION: xpt-G17-IR-2

<400> SEQUENCE: 17

```
gtgagtctat gggacccttg atgttttctt tccctgctct ttcagggcaa taatgataca     60
atgtatcatg ccgagtaacg ctgtttctct aacttgtagg aatgaattca gatatttcca    120
gagaatgaaa aaaaaatctt cagtagaagg taatgtataa tcgcgtggat atggcacgca    180
agtttctacc gggcaccgta aatgtccgac tacattacgc accattctaa agaataacag    240
tgataatttc tgggttaagg caatagcaat atttctgcat ataaatattt ctgcatataa    300
attgtaactg atgtaagagg tttcatattg ctaatagcag ctacaatcca gctaccattc    360
tgcttttatt ttatggttgg gataaggctg gattattctg agtccaagct aggccctttt    420
gctaatcatg ttcatacctc ttatcttcct cccacag                             457
```

<210> SEQ ID NO 18
<211> LENGTH: 582
<212> TYPE: DNA
<213> ORGANISM: Artificial Sequence
<220> FEATURE:
<223> OTHER INFORMATION: xpt-G17-IR-3

<400> SEQUENCE: 18

```
gtgagtctat gggacccttg atgttttctt tccccttctt ttctatggtt aagttcatgt     60
gctcaaatca gggtaatttt gcatttgtaa ttttaaaaaa tgctttcttc ttttaatata    120
cttttttgtt tatcttattt ctaatacttt ccctaatctc tttctttcag ggcaataatg    180
atacaatgta tcatgccgag taacgctgtt tctctaactt gtaggaatga attcagatat    240
ttccagagaa tgaaaaaaaa atcttcagta gaaggtaatg tataatcgcg tggatatggc    300
acgcaagttt ctaccgggca ccgtaaatgt ccgactacat tacgcaccat tctaaagaat    360
aacagtgata atttctgggt taaggcaata gcaatatttc tgcatataaa tatttctgca    420
tataaattgt aactgatgta agaggtttca tattgctaat agcagctaca atccagctac    480
cattctgctt ttattttatg gttgggataa ggctggatta ttctgagtcc aagctaggcc    540
cttttgctaa tcatgttcat acctcttatc ttcctcccac ag                       582
```

<210> SEQ ID NO 19
<211> LENGTH: 482
<212> TYPE: DNA
<213> ORGANISM: Artificial Sequence
<220> FEATURE:
<223> OTHER INFORMATION: xpt-G17-IR-4

<400> SEQUENCE: 19

```
gtgagtctat gggacccttg atgttttctt tccccttctt ttctatggtt aagttcatgt     60
gctctttcag ggcaataatg atacaatgta tcatgccgag taacgctgtt tctctaactt    120
gtaggaatga attcagatat ttccagagaa tgaaaaaaaa atcttcagta gaaggtaatg    180
tataatcgcg tggatatggc acgcaagttt ctaccgggca ccgtaaatgt ccgactacat    240
tacgcaccat tctaaagaat aacagtgata atttctgggt taaggcaata gcaatatttc    300
tgcatataaa tatttctgca tataaattgt aactgatgta agaggtttca tattgctaat    360
```

| | |
|---|---|
| agcagctaca atccagctac cattctgctt ttattttatg gttgggataa ggctggatta | 420 |
| ttctgagtcc aagctaggcc ttttgctaa tcatgttcat acctcttatc ttcctcccac | 480 |
| ag | 482 |

<210> SEQ ID NO 20
<211> LENGTH: 611
<212> TYPE: DNA
<213> ORGANISM: Artificial Sequence
<220> FEATURE:
<223> OTHER INFORMATION: xpt-G17-IR-5

<400> SEQUENCE: 20

| | |
|---|---|
| gtgagtctat gggacccttg atgttttctt tccccttctt ttctatggtt aagttcatgt | 60 |
| cataggaagg ggagaagtaa cagggtactg ctcaaatcag ggtaattttg catttgtaat | 120 |
| tttaaaaaat gctttcttct tttaatatac ttttttgttt atcttatttc taatactttc | 180 |
| cctaatctct ttctttcagg gcaataatga tacaatgtat catgccgagt aacgctgttt | 240 |
| ctctaacttg taggaatgaa ttcagatatt ccagagaat gaaaaaaaaa tcttcagtag | 300 |
| aaggtaatgt ataatcgcgt ggatatggca cgcaagtttc taccgggcac cgtaaatgtc | 360 |
| cgactacatt acgcaccatt ctaaagaata acagtgataa tttctgggtt aaggcaatag | 420 |
| caatatttct gcatataaat atttctgcat ataaattgta actgatgtaa gaggtttcat | 480 |
| attgctaata gcagctacaa tccagctacc attctgcttt tattttatgg ttgggataag | 540 |
| gctggattat tctgagtcca agctaggccc ttttgctaat catgttcata cctcttatct | 600 |
| tcctcccaca g | 611 |

<210> SEQ ID NO 21
<211> LENGTH: 511
<212> TYPE: DNA
<213> ORGANISM: Artificial Sequence
<220> FEATURE:
<223> OTHER INFORMATION: xpt-G17-IR-6

<400> SEQUENCE: 21

| | |
|---|---|
| gtgagtctat gggacccttg atgttttctt tccccttctt ttctatggtt aagttcatgt | 60 |
| cataggaagg ggagaagtaa cagggtactg ctctttcagg gcaataatga tacaatgtat | 120 |
| catgccgagt aacgctgttt ctctaacttg taggaatgaa ttcagatatt ccagagaat | 180 |
| gaaaaaaaaa tcttcagtag aaggtaatgt ataatcgcgt ggatatggca cgcaagtttc | 240 |
| taccgggcac cgtaaatgtc cgactacatt acgcaccatt ctaaagaata acagtgataa | 300 |
| tttctgggtt aaggcaatag caatatttct gcatataaat atttctgcat ataaattgta | 360 |
| actgatgtaa gaggtttcat attgctaata gcagctacaa tccagctacc attctgcttt | 420 |
| tattttatgg ttgggataag gctggattat tctgagtcca agctaggccc ttttgctaat | 480 |
| catgttcata cctcttatct tcctcccaca g | 511 |

<210> SEQ ID NO 22
<211> LENGTH: 592
<212> TYPE: DNA
<213> ORGANISM: Artificial Sequence
<220> FEATURE:
<223> OTHER INFORMATION: xpt-G17-IR-7

<400> SEQUENCE: 22

| | |
|---|---|
| gtgagtctat gggacccttg atgttttctt tccccttctt ttctatggtt aagttcatgt | 60 |

```
cataggaagt gctcaaatca gggtaatttt gcatttgtaa ttttaaaaaa tgctttcttc    120
ttttaatata cttttttgtt tatcttattt ctaatacttt ccctaatctc tttcttcag     180 ggcaataatg atacaatgta tcatgccgag taacgctgtt tctctaactt gtaggaatga    240
attcagatat ttccagagaa tgaaaaaaaa atcttcagta gaaggtaatg tataatcgcg    300
tggatatggc acgcaagttt ctaccgggca ccgtaaatgt ccgactacat tacgcaccat    360
tctaaagaat aacagtgata atttctgggt taaggcaata gcaatatttc tgcatataaa    420
tatttctgca tataaattgt aactgatgta agaggtttca tattgctaat agcagctaca    480
atccagctac cattctgctt ttattttatg gttgggataa ggctggatta ttctgagtcc    540
aagctaggcc ttttgctaa tcatgttcat acctcttatc ttcctcccac ag             592
```

<210> SEQ ID NO 23
<211> LENGTH: 492
<212> TYPE: DNA
<213> ORGANISM: Artificial Sequence
<220> FEATURE:
<223> OTHER INFORMATION: xpt-G17-IR-8

<400> SEQUENCE: 23

```
gtgagtctat gggacccttg atgttttctt tccccttctt ttctatggtt aagttcatgt     60
cataggaagt gctctttcag ggcaataatg atacaatgta tcatgccgag taacgctgtt    120
tctctaactt gtaggaatga attcagatat ttccagagaa tgaaaaaaaa atcttcagta    180
gaaggtaatg tataatcgcg tggatatggc acgcaagttt ctaccgggca ccgtaaatgt    240
ccgactacat tacgcaccat tctaaagaat aacagtgata atttctgggt taaggcaata    300
gcaatatttc tgcatataaa tatttctgca tataaattgt aactgatgta agaggtttca    360
tattgctaat agcagctaca atccagctac cattctgctt ttattttatg gttgggataa    420
ggctggatta ttctgagtcc aagctaggcc ttttgctaa tcatgttcat acctcttatc    480
ttcctcccac ag                                                        492
```

<210> SEQ ID NO 24
<211> LENGTH: 502
<212> TYPE: DNA
<213> ORGANISM: Artificial Sequence
<220> FEATURE:
<223> OTHER INFORMATION: xpt-G17-IR-9

<400> SEQUENCE: 24

```
gtgagtctat gggacccttg atgttttctt tccccttctt ttctatggtt aagttcatgt     60
cataggaagg ggagaagtaa cagggtacac atattgacca aatcagggta attttgcatt    120
tgtaatttta aaaatgctt tcttctttta atatactttt ttgttatct tatttctaat     180 actttcccta atctctttct tcagggcaa taatgataca atgtatcatg ccgagtaacg    240
ctgtttctct aacttgtagg aatgaattca gatatttcca gagaatgaaa aaaaatctt    300 cagtagaagg taatgtataa tcgcgtggat atggcacgca agtttctacc gggcaccgta    360
aatgtccgac tacattacgc accattctaa agaataacag tgataatttc tgggttaagg    420
caatagctgc tgctggatta ttctgagtcc aagctaggcc ttttgctaa tcatgttcat    480 acctcttatc ttcctcccac ag                                              502
```

<210> SEQ ID NO 25
<211> LENGTH: 587
<212> TYPE: DNA
<213> ORGANISM: Artificial Sequence
<220> FEATURE:
<223> OTHER INFORMATION: xpt-G17-IR-10

<400> SEQUENCE: 25

```
gtgagtctat gggacccttg atgttttctt tccccttctt ttctatggtt aagttcatgt      60
cataggaagg ggagaagtaa cagggtacac atattgacca aatcagggta attttgcatt     120
tgtaatttta aaaaatgctt tcttctttta atatactttt ttgtttatct tatttctaat     180
actttcccta atctctttct ttcagggcaa taatgataca atgtatcatg ccgagtaacg     240
ctgtttctct aacttgtagg aatgaattca gatatttcca gagaatgaaa aaaaaatctt     300
cagtagaagg taatgtataa tcgcgtggat atggcacgca agtttctacc gggcaccgta     360
aatgtccgac tacattacgc accattctaa agaataacag tgataatttc tgggttaagg     420
caatagcaat atttctgcat ataaatattt ctgcatataa attgtaactg atgtaagagg     480
tttcatattg ctaatagcag ctacaatcca gctgctgctg gattattctg agtccaagct     540
aggcccttt gctaatcatg ttcataccctc ttatcttcct cccacag                  587
```

<210> SEQ ID NO 26
<211> LENGTH: 572
<212> TYPE: DNA
<213> ORGANISM: Artificial Sequence
<220> FEATURE:
<223> OTHER INFORMATION: xpt-G17-IR-11

<400> SEQUENCE: 26

```
gtgagtctat gggacccttg atgttttctt tccccttctt ttctatggtt aagttcatgt      60
cataggaagg ggagaagtaa cagggtacac atattgacca aatcagggta attttgcatt     120
tgtaatttta aaaaatgctt tcttctttta atatactttt ttgtttatct tatttctaat     180
actttcccta atctctttct ttcagggcaa taatgataca atgtatcatg ccgagtaacg     240
ctgtttctct aacttgtagg aatgaattca gatatttcca gagaatgaaa aaaaaatctt     300
cagtagaagg taatgtataa tcgcgtggat atggcacgca agtttctacc gggcaccgta     360
aatgtccgac tacattacgc accattctaa agaataacag tgataatttc tgggttaagg     420
caatagctgc tgaggtttca tattgctaat agcagctaca atccagctac cattctgctt     480
ttattttatg gttgggataa ggctggatta ttctgagtcc aagctaggcc ttttgctaa      540
tcatgttcat acctcttatc ttcctcccac ag                                   572
```

<210> SEQ ID NO 27
<211> LENGTH: 537
<212> TYPE: DNA
<213> ORGANISM: Artificial Sequence
<220> FEATURE:
<223> OTHER INFORMATION: xpt-G17-IR-13

<400> SEQUENCE: 27

```
gtgagtctat gggacccttg atgttttctt tccccttctt ttctatggtt aagttcatgt      60
cataggaagg ggagaagtaa cagggtacac atattgacca aatcagggta attttgcatt     120
tgtaatttta aaaaatgctt tcttctttta atatactttt ttgtttatct tatttctaat     180
actttcccta atctctttct ttcagggcaa taatgataca atgtatcatg ccgagtaacg     240
ctgtttctct aacttgtagg aatgaattca gatatttcca gagaatgaaa aaaaaatctt     300
cagtagaagg taatgtataa tcgcgtggat atggcacgca agtttctacc gggcaccgta     360
aatgtccgac tacattacgc accattctaa agaataacag tgataatttc tgggttaagg     420
```
caatagctgc tctaccattc tgcttttatt ttatggttgg gataaggctg gattattctg    480
agtccaagct aggccctttt gctaatcatg ttcatacctc ttatcttcct cccacag        537

<210> SEQ ID NO 28
<211> LENGTH: 552
<212> TYPE: DNA
<213> ORGANISM: Artificial Sequence
<220> FEATURE:
<223> OTHER INFORMATION: xpt-G17-IR-15

<400> SEQUENCE: 28
gtgagtctat gggacccttg atgttttctt tcccctt ctt ttctatggtt aagttcatgt     60
cataggaagg ggagaagtaa cagggtacac atattgacca aatcagggta attttgcatt    120
tgtaatttta aaaatgcttt cttctttta atatactttt ttgtttatct tatttctaat     180
actttcccta atctctttct ttcagggcaa taatgataca atgtatcatg ccgagtaacg    240
ctgtttctct aacttgtagg aatgaattca gatatttcca gagaatgaaa aaaaaatctt    300
cagtagaagg taatgtataa tcgcgtggat atggcacgca gtttctacc gggcaccgta     360 aatgtccgac tacattacgc accattctaa agaataacag tgataatttc tgggttaagg    420
caatagctgc tgcagctaca atccagctac cattctgctt ttattttatg gttgggataa    480
ggctggatta ttctgagtcc aagctaggcc ttttgctaa tcatgttcat acctcttatc     540
ttcctcccac ag                                                         552

<210> SEQ ID NO 29
<211> LENGTH: 442
<212> TYPE: DNA
<213> ORGANISM: Artificial Sequence
<220> FEATURE:
<223> OTHER INFORMATION: xpt-G17-2IR-1

<400> SEQUENCE: 29
gtgagtctat gggacccttg atgttttctt tccctgctca aatcagggta attttgcatt     60
tgtaatttta aaaatgcttt cttctttta atatactttt ttgtttatct tatttctaat    120
actttcccta atctctttct ttcagggcaa taatgataca atgtatcatg ccgagtaacg    180
ctgtttctct aacttgtagg aatgaattca gatatttcca gagaatgaaa aaaaaatctt    240
cagtagaagg taatgtataa tcgcgtggat atggcacgca gtttctacc gggcaccgta     300 aatgtccgac tacattacgc accattctaa agaataacag tgataatttc tgggttaagg    360
caatagctgc tgctggatta ttctgagtcc aagctaggcc ttttgctaa tcatgttcat     420 acctcttatc ttcctcccac ag                                              442

<210> SEQ ID NO 30
<211> LENGTH: 527
<212> TYPE: DNA
<213> ORGANISM: Artificial Sequence
<220> FEATURE:
<223> OTHER INFORMATION: xpt-G17-2IR-2

<400> SEQUENCE: 30
gtgagtctat gggacccttg atgttttctt tccctgctca aatcagggta attttgcatt     60
tgtaatttta aaaatgcttt cttctttta atatactttt ttgtttatct tatttctaat    120
actttcccta atctctttct ttcagggcaa taatgataca atgtatcatg ccgagtaacg    180
ctgtttctct aacttgtagg aatgaattca gatatttcca gagaatgaaa aaaaaatctt    240
cagtagaagg taatgtataa tcgcgtggat atggcacgca gtttctacc gggcaccgta     300

```
aatgtccgac tacattacgc accattctaa agaataacag tgataatttc tgggttaagg      360
caatagcaat atttctgcat ataaatattt ctgcatataa attgtaactg atgtaagagg      420
tttcatattg ctaatagcag ctacaatcca gctgctgctg gattattctg agtccaagct      480 aggcccttt gctaatcatg ttcataccte ttatcttcct cccacag                    527

<210> SEQ ID NO 31
<211> LENGTH: 512
<212> TYPE: DNA
<213> ORGANISM: Artificial Sequence
<220> FEATURE:
<223> OTHER INFORMATION: xpt-G17-2IR-3

<400> SEQUENCE: 31
gtgagtctat gggacccttg atgttttctt tccctgctca aatcagggta attttgcatt       60
tgtaatttta aaaatgctt tcttctttta atatactttt ttgtttatct tatttctaat      120
actttcccta atctctttct ttcagggcaa taatgataca atgtatcatg ccgagtaacg      180
ctgtttctct aacttgtagg aatgaattca gatatttcca gagaatgaaa aaaaaatctt      240
cagtagaagg taatgtataa tcgcgtggat atggcacgca agtttctacc gggcaccgta      300
aatgtccgac tacattacgc accattctaa agaataacag tgataatttc tgggttaagg      360
caatagctgc tgaggtttca tattgctaat agcagctaca atccagctac cattctgctt      420
ttattttatg gttgggataa ggctggatta ttctgagtcc aagctaggcc cttttgctaa      480
tcatgttcat acctcttatc ttcctcccac ag                                    512

<210> SEQ ID NO 32
<211> LENGTH: 477
<212> TYPE: DNA
<213> ORGANISM: Artificial Sequence
<220> FEATURE:
<223> OTHER INFORMATION: xpt-G17-2IR-4

<400> SEQUENCE: 32
gtgagtctat gggacccttg atgttttctt tccctgctca aatcagggta attttgcatt       60
tgtaatttta aaaatgctt tcttctttta atatactttt ttgtttatct tatttctaat      120
actttcccta atctctttct ttcagggcaa taatgataca atgtatcatg ccgagtaacg      180
ctgtttctct aacttgtagg aatgaattca gatatttcca gagaatgaaa aaaaaatctt      240
cagtagaagg taatgtataa tcgcgtggat atggcacgca agtttctacc gggcaccgta      300
aatgtccgac tacattacgc accattctaa agaataacag tgataatttc tgggttaagg      360
caatagctgc tctaccattc tgcttttatt ttatggttgg gataaggctg gattattctg      420
agtccaagct aggcccttt gctaatcatg ttcataccte ttatcttcct cccacag         477

<210> SEQ ID NO 33
<211> LENGTH: 492
<212> TYPE: DNA
<213> ORGANISM: Artificial Sequence
<220> FEATURE:
<223> OTHER INFORMATION: xpt-G17-2IR-5

<400> SEQUENCE: 33
gtgagtctat gggacccttg atgttttctt tccctgctca aatcagggta attttgcatt       60
tgtaatttta aaaatgctt tcttctttta atatactttt ttgtttatct tatttctaat      120
actttcccta atctctttct ttcagggcaa taatgataca atgtatcatg ccgagtaacg      180
```

| | |
|---|---|
| ctgtttctct aacttgtagg aatgaattca gatatttcca gagaatgaaa aaaaaatctt | 240 |
| cagtagaagg taatgtataa tcgcgtggat atggcacgca agtttctacc gggcaccgta | 300 |
| aatgtccgac tacattacgc accattctaa agaataacag tgataatttc tgggttaagg | 360 |
| caatagctgc tgcagctaca atccagctac cattctgctt ttattttatg gttgggataa | 420 |
| ggctggatta ttctgagtcc aagctaggcc ttttgctaa tcatgttcat acctcttatc | 480 |
| ttcctcccac ag | 492 |

<210> SEQ ID NO 34
<211> LENGTH: 467
<212> TYPE: DNA
<213> ORGANISM: Artificial Sequence
<220> FEATURE:
<223> OTHER INFORMATION: xpt-G17-2IR-6

<400> SEQUENCE: 34

| | |
|---|---|
| gtgagtctat gggacccttg atgttttctt tccccttctt ttctatggtt aagttcatgt | 60 |
| gctcaaatca gggtaatttt gcatttgtaa ttttaaaaaa tgctttcttc ttttaatata | 120 |
| cttttttgtt tatcttattt ctaatacttt ccctaatctc tttctttcag gcaataatg | 180 |
| atacaatgta tcatgccgag taacgctgtt tctctaactt gtaggaatga attcagatat | 240 |
| ttccagagaa tgaaaaaaaa atcttcagta gaaggtaatg tataatcgcg tggatatggc | 300 |
| acgcaagttt ctaccgggca ccgtaaatgt ccgactacat tacgcaccat tctaaagaat | 360 |
| aacagtgata atttctgggt taaggcaata gctgctgctg gattattctg agtccaagct | 420 |
| aggccctttt gctaatcatg ttcataccctc ttatcttcct cccacag | 467 |

<210> SEQ ID NO 35
<211> LENGTH: 552
<212> TYPE: DNA
<213> ORGANISM: Artificial Sequence
<220> FEATURE:
<223> OTHER INFORMATION: xpt-G17-2IR-7

<400> SEQUENCE: 35

| | |
|---|---|
| gtgagtctat gggacccttg atgttttctt tccccttctt ttctatggtt aagttcatgt | 60 |
| gctcaaatca gggtaatttt gcatttgtaa ttttaaaaaa tgctttcttc ttttaatata | 120 |
| cttttttgtt tatcttattt ctaatacttt ccctaatctc tttctttcag gcaataatg | 180 |
| atacaatgta tcatgccgag taacgctgtt tctctaactt gtaggaatga attcagatat | 240 |
| ttccagagaa tgaaaaaaaa atcttcagta gaaggtaatg tataatcgcg tggatatggc | 300 |
| acgcaagttt ctaccgggca ccgtaaatgt ccgactacat tacgcaccat tctaaagaat | 360 |
| aacagtgata atttctgggt taaggcaata gcaatatttc tgcatataaa tatttctgca | 420 |
| tataaattgt aactgatgta agaggtttca tattgctaat agcagctaca atccagctgc | 480 |
| tgctggatta ttctgagtcc aagctaggcc ttttgctaa tcatgttcat acctcttatc | 540 |
| ttcctcccac ag | 552 |

<210> SEQ ID NO 36
<211> LENGTH: 537
<212> TYPE: DNA
<213> ORGANISM: Artificial Sequence
<220> FEATURE:
<223> OTHER INFORMATION: xpt-G17-2IR-8

<400> SEQUENCE: 36

| | |
|---|---|
| gtgagtctat gggacccttg atgttttctt tccccttctt ttctatggtt aagttcatgt | 60 |

```
gctcaaatca gggtaatttt gcatttgtaa ttttaaaaaa tgctttcttc ttttaatata    120
cttttttgtt tatcttattt ctaatacttt ccctaatctc tttctttcag ggcaataatg    180
atacaatgta tcatgccgag taacgctgtt tctctaactt gtaggaatga attcagatat    240
ttccagagaa tgaaaaaaaa atcttcagta gaaggtaatg tataatcgcg tggatatggc    300
acgcaagttt ctaccgggca ccgtaaatgt ccgactacat tacgcaccat tctaaagaat    360
aacagtgata atttctgggt taaggcaata gctgctgagg tttcatattg ctaatagcag    420
ctacaatcca gctaccattc tgcttttatt ttatggttgg gataaggctg gattattctg    480
agtccaagct aggcccttt gctaatcatg ttcatacctc ttatcttcct cccacag      537
```

<210> SEQ ID NO 37
<211> LENGTH: 502
<212> TYPE: DNA
<213> ORGANISM: Artificial Sequence
<220> FEATURE:
<223> OTHER INFORMATION: xpt-G17-2IR-9

<400> SEQUENCE: 37

```
gtgagtctat gggacccttg atgttttctt tccccttctt ttctatggtt aagttcatgt     60
gctcaaatca gggtaatttt gcatttgtaa ttttaaaaaa tgctttcttc ttttaatata    120
cttttttgtt tatcttattt ctaatacttt ccctaatctc tttctttcag ggcaataatg    180
atacaatgta tcatgccgag taacgctgtt tctctaactt gtaggaatga attcagatat    240
ttccagagaa tgaaaaaaaa atcttcagta gaaggtaatg tataatcgcg tggatatggc    300
acgcaagttt ctaccgggca ccgtaaatgt ccgactacat tacgcaccat tctaaagaat    360
aacagtgata atttctgggt taaggcaata gctgctctac cattctgctt ttatttatg    420 gttgggataa ggctggatta ttctgagtcc aagctaggcc ttttgctaa tcatgttcat    480 acctcttatc ttcctcccac ag                                            502
```

<210> SEQ ID NO 38
<211> LENGTH: 517
<212> TYPE: DNA
<213> ORGANISM: Artificial Sequence
<220> FEATURE:
<223> OTHER INFORMATION: xpt-G17-2IR-10

<400> SEQUENCE: 38

```
gtgagtctat gggacccttg atgttttctt tccccttctt ttctatggtt aagttcatgt     60
gctcaaatca gggtaatttt gcatttgtaa ttttaaaaaa tgctttcttc ttttaatata    120
cttttttgtt tatcttattt ctaatacttt ccctaatctc tttctttcag ggcaataatg    180
atacaatgta tcatgccgag taacgctgtt tctctaactt gtaggaatga attcagatat    240
ttccagagaa tgaaaaaaaa atcttcagta gaaggtaatg tataatcgcg tggatatggc    300
acgcaagttt ctaccgggca ccgtaaatgt ccgactacat tacgcaccat tctaaagaat    360
aacagtgata atttctgggt taaggcaata gctgctgcag ctacaatcca gctaccattc    420
tgcttttatt ttatggttgg gataaggctg gattattctg agtccaagct aggccctttt    480
gctaatcatg ttcatacctc ttatcttcct cccacag                             517
```

<210> SEQ ID NO 39
<211> LENGTH: 342
<212> TYPE: DNA
<213> ORGANISM: Artificial Sequence
<220> FEATURE:

<223> OTHER INFORMATION: xpt-G17-2IR-11

<400> SEQUENCE: 39

| gtgagtctat gggacccttg atgttttctt tccctgctct ttcagggcaa taatgataca | 60 |
| atgtatcatg ccgagtaacg ctgtttctct aacttgtagg aatgaattca gatatttcca | 120 |
| gagaatgaaa aaaaaatctt cagtagaagg taatgtataa tcgcgtggat atggcacgca | 180 |
| agtttctacc gggcaccgta aatgtccgac tacattacgc accattctaa agaataacag | 240 |
| tgataaattc tgggttaagg caatagctgc tgctggatta ttctgagtcc aagctaggcc | 300 |
| cttttgctaa tcatgttcat acctcttatc ttcctcccac ag | 342 |

```
<210> SEQ ID NO 40
<211> LENGTH: 377
<212> TYPE: DNA
<213> ORGANISM: Artificial Sequence
<220> FEATURE:
<223> OTHER INFORMATION: xpt-G17-2IR-12
```

<400> SEQUENCE: 40

| gtgagtctat gggacccttg atgttttctt tccctgctct ttcagggcaa taatgataca | 60 |
| atgtatcatg ccgagtaacg ctgtttctct aacttgtagg aatgaattca gatatttcca | 120 |
| gagaatgaaa aaaaaatctt cagtagaagg taatgtataa tcgcgtggat atggcacgca | 180 |
| agtttctacc gggcaccgta aatgtccgac tacattacgc accattctaa agaataacag | 240 |
| tgataaattc tgggttaagg caatagctgc tctaccattc tgcttttatt ttatggttgg | 300 |
| gataaggctg gattattctg agtccaagct aggcccttttt gctaatcatg ttcatacctc | 360 |
| ttatcttcct cccacag | 377 |

```
<210> SEQ ID NO 41
<211> LENGTH: 367
<212> TYPE: DNA
<213> ORGANISM: Artificial Sequence
<220> FEATURE:
<223> OTHER INFORMATION: xpt-G17-2IR-13
```

<400> SEQUENCE: 41

| gtgagtctat gggacccttg atgttttctt tccccttctt ttctatggtt aagttcatgt | 60 |
| gctcttttcag ggcaataatg atacaatgta tcatgccgag taacgctgtt tctctaactt | 120 |
| gtaggaatga attcagatat ttccagagaa tgaaaaaaaa atcttcagta gaaggtaatg | 180 |
| tataatcgcg tggatatggc acgcaagttt ctaccgggca ccgtaaatgt ccgactacat | 240 |
| tacgcaccat tctaaagaat aacagtgata aatttctgggt taaggcaata gctgctgctg | 300 |
| gattattctg agtccaagct aggcccttttt gctaatcatg ttcatacctc ttatcttcct | 360 |
| cccacag | 367 |

```
<210> SEQ ID NO 42
<211> LENGTH: 402
<212> TYPE: DNA
<213> ORGANISM: Artificial Sequence
<220> FEATURE:
<223> OTHER INFORMATION: xpt-G17-2IR-14
```

<400> SEQUENCE: 42

| gtgagtctat gggacccttg atgttttctt tccccttctt ttctatggtt aagttcatgt | 60 |
| gctcttttcag ggcaataatg atacaatgta tcatgccgag taacgctgtt tctctaactt | 120 |
| gtaggaatga attcagatat ttccagagaa tgaaaaaaaa atcttcagta gaaggtaatg | 180 |

| | |
|---|---|
| tataatcgcg tggatatggc acgcaagttt ctaccgggca ccgtaaatgt ccgactacat | 240 |
| tacgcaccat tctaaagaat aacagtgata atttctgggt taaggcaata gctgctctac | 300 |
| cattctgctt ttattttatg gttgggataa ggctggatta ttctgagtcc aagctaggcc | 360 |
| cttttgctaa tcatgttcat acctcttatc ttcctcccac ag | 402 |

<210> SEQ ID NO 43
<211> LENGTH: 396
<212> TYPE: DNA
<213> ORGANISM: Artificial Sequence
<220> FEATURE:
<223> OTHER INFORMATION: xpt-G17-2IR-15

<400> SEQUENCE: 43

| | |
|---|---|
| gtgagtctat gggacccttg atgttttctt tccccttctt ttctatggtt aagttcatgt | 60 |
| cataggaagg ggagaagtaa cagggtactg ctctttcagg gcaataatga tacaatgtat | 120 |
| catgccgagt aacgctgttt ctctaacttg taggaatgaa ttcagatatt tccagagaat | 180 |
| gaaaaaaaaa tcttcagtag aaggtaatgt ataatcgcgt ggatatggca cgcaagtttc | 240 |
| taccgggcac cgtaaatgtc cgactacatt acgcaccatt ctaaagaata acagtgataa | 300 |
| tttctgggtt aaggcaatag ctgctgctgg attattctga gtccaagcta ggcccttttg | 360 |
| ctaatcatgt tcatacctct tatcttcctc ccacag | 396 |

<210> SEQ ID NO 44
<211> LENGTH: 431
<212> TYPE: DNA
<213> ORGANISM: Artificial Sequence
<220> FEATURE:
<223> OTHER INFORMATION: xpt-G17-2IR-16

<400> SEQUENCE: 44

| | |
|---|---|
| gtgagtctat gggacccttg atgttttctt tccccttctt ttctatggtt aagttcatgt | 60 |
| cataggaagg ggagaagtaa cagggtactg ctctttcagg gcaataatga tacaatgtat | 120 |
| catgccgagt aacgctgttt ctctaacttg taggaatgaa ttcagatatt tccagagaat | 180 |
| gaaaaaaaaa tcttcagtag aaggtaatgt ataatcgcgt ggatatggca cgcaagtttc | 240 |
| taccgggcac cgtaaatgtc cgactacatt acgcaccatt ctaaagaata acagtgataa | 300 |
| tttctgggtt aaggcaatag ctgctctacc attctgcttt tattttatgg ttgggataag | 360 |
| gctggattat tctgagtcca agctaggccc ttttgctaat catgttcata cctcttatct | 420 |
| tcctcccaca g | 431 |

<210> SEQ ID NO 45
<211> LENGTH: 617
<212> TYPE: DNA
<213> ORGANISM: Artificial Sequence
<220> FEATURE:
<223> OTHER INFORMATION: xpt-G17-3ssC-1

<400> SEQUENCE: 45

| | |
|---|---|
| gtgagtctat gggacccttg atgttttctt tccccttctt ttctatggtt aagttcatgt | 60 |
| cataggaagg ggagaagtaa cagggtacac atattgacca aatcaggta attttgcatt | 120 |
| tgtaatttta aaaatgctt tcttctttta atatacttt tgtttatct tatttctaat | 180 |
| actttcccta atctctttct ttcagggcaa taatgataca atgtatcatg ccgagtaacg | 240 |
| ctgtttctct aacttccccg aatgaattca gatatttcca gagaatgaaa aaaaatctt | 300 |

```
cagtagaagg taatgtataa tcgcgtggat atggcacgca agtttctacc gggcaccgta    360
aatgtccgac tacattacgc accattctaa agaataacag tgataatttc tggggttaagg   420 caatagcaat atttctgcat ataaatattt ctgcatataa attgtaactg atgtaagagg    480
tttcatattg ctaatagcag ctacaatcca gctaccattc tgcttttatt ttatggttgg    540
gataaggctg gattattctg agtccaagct aggccctttt gctaatcatg ttcatacctc    600
ttatcttcct cccacag                                                   617

<210> SEQ ID NO 46
<211> LENGTH: 621
<212> TYPE: DNA
<213> ORGANISM: Artificial Sequence
<220> FEATURE:
<223> OTHER INFORMATION: xpt-G15 riboswitch

<400> SEQUENCE: 46
gtgagtctat gggacccttg atgttttctt tccccttctt ttctatggtt aagttcatgt     60
cataggaagg ggagaagtaa cagggtacac atattgacca aatcagggta attttgcatt    120
tgtaatttta aaaatgctt tcttctttta atatacttt tgtttatct tatttctaat       180 actttcccta atctctttct ttcagggcaa taatgataca atgtatcatg ccgagtaacg    240
ctgtttctct aacttgtagg aatgaattca gatatttcca gagaatgaaa aaaaaatctt    300
cagtagaagg taatgtgtat aatcgcgtgg atatggcacg caagtttcta ccgggcaccg    360
taaatgtccg actacacatt acgcaccatt ctaaagaata acagtgataa tttctgggtt    420
aaggcaatag caatatttct gcatataaat atttctgcat ataaattgta actgatgtaa    480
gaggtttcat attgctaata gcagctacaa tccagctacc attctgcttt tattttatgg    540
ttgggataag gctggattat tctgagtcca agctaggccc ttttgctaat catgttcata    600
cctcttatct tcctcccaca g                                              621

<210> SEQ ID NO 47
<211> LENGTH: 85
<212> TYPE: DNA
<213> ORGANISM: Artificial Sequence
<220> FEATURE:
<223> OTHER INFORMATION: DHFR WildType 5 single-strand

<400> SEQUENCE: 47
gagtaacgct gtttctctaa cttgtaggaa tgaattcaga tatttccaga gaatgaccac     60
aacctcttca gtagaaggta atgtg                                           85

<210> SEQ ID NO 48
<211> LENGTH: 85
<212> TYPE: DNA
<213> ORGANISM: Artificial Sequence
<220> FEATURE:
<223> OTHER INFORMATION: DHFR 5 single-strandC

<400> SEQUENCE: 48
gagtaacgct gtttctctaa cttgtaggaa tgaattcaga tatttccaga gaatgaccac     60
aacctcttca gtagaagccc ctgtg                                           85

<210> SEQ ID NO 49
<211> LENGTH: 85
<212> TYPE: DNA
<213> ORGANISM: Artificial Sequence
<220> FEATURE:
<223> OTHER INFORMATION: DHFR-Con1 5 single-strand
```

<400> SEQUENCE: 49
gagtaacgct gtttctctaa cttgtaggaa tgaattcaga tatttccaga gaatgaccac    60
aacctcttca gtagagggtg agttg    85

<210> SEQ ID NO 50
<211> LENGTH: 85
<212> TYPE: DNA
<213> ORGANISM: Artificial Sequence
<220> FEATURE:
<223> OTHER INFORMATION: DHFR-Con4 5 single-strand

<400> SEQUENCE: 50
gagtaacgct gtttctctaa cttgtaggaa tgaattcaga tatttccaga gaatgaccac    60
aacctcttca gtaggaggtg tggtg    85

<210> SEQ ID NO 51
<211> LENGTH: 85
<212> TYPE: DNA
<213> ORGANISM: Artificial Sequence
<220> FEATURE:
<223> OTHER INFORMATION: DHFR WildType mtSRp40

<400> SEQUENCE: 51
gagtaacgct gtttctctaa cttgtaggaa tgaattcaga tatttccaga gaatgaaaaa    60
aaaatcttca gtagaaggta atgtg    85

<210> SEQ ID NO 52
<211> LENGTH: 85
<212> TYPE: DNA
<213> ORGANISM: Artificial Sequence
<220> FEATURE:
<223> OTHER INFORMATION: DHFR WildType strongSC35

<400> SEQUENCE: 52
gagtaacgct gtttctctaa cttgtaggaa tggcccctga tatttccaga gaatgaccac    60
aacctcttca gtagaaggta atgtg    85

<210> SEQ ID NO 53
<211> LENGTH: 85
<212> TYPE: DNA
<213> ORGANISM: Artificial Sequence
<220> FEATURE:
<223> OTHER INFORMATION: DHFR WildType SC35hnRNPA1

<400> SEQUENCE: 53
gagtaacgct gtttctctaa cttgtaggaa tgtagggaga tatttccaga gaatgaccac    60
aacctcttca gtagaaggta atgtg    85

<210> SEQ ID NO 54
<211> LENGTH: 106
<212> TYPE: DNA
<213> ORGANISM: Artificial Sequence
<220> FEATURE:
<223> OTHER INFORMATION: DHFR-Con1 5 single-strand HP15

<400> SEQUENCE: 54
gagtaacgct gtttctctaa cttgtaggaa tgaattcaga tatttccaga gaatgaccac    60
aacctcttca gtagagggtg agttggcgaa agccaactca ccctct    106

<210> SEQ ID NO 55

```
<211> LENGTH: 106
<212> TYPE: DNA
<213> ORGANISM: Artificial Sequence
<220> FEATURE:
<223> OTHER INFORMATION: DHFR-Con1 5 single-strand HP15x

<400> SEQUENCE: 55
gagtaacgct gtttctctaa cttgtaggaa tgaattcaga tatttccaga gaatgaccac      60
aacctcttca gtagagggtg agttggcgaa aacagcata aagtat                    106

<210> SEQ ID NO 56
<211> LENGTH: 106
<212> TYPE: DNA
<213> ORGANISM: Artificial Sequence
<220> FEATURE:
<223> OTHER INFORMATION: DHFR WildType mtSRp40 HP15

<400> SEQUENCE: 56
gagtaacgct gtttctctaa cttgtaggaa tgaattcaga tatttccaga gaatgaaaaa      60
aaaatcttca gtagaaggta atgtggcgaa agccacatta ccttct                   106

<210> SEQ ID NO 57
<211> LENGTH: 106
<212> TYPE: DNA
<213> ORGANISM: Artificial Sequence
<220> FEATURE:
<223> OTHER INFORMATION: DHFR WildType mtSRp40 HP15X

<400> SEQUENCE: 57
gagtaacgct gtttctctaa cttgtaggaa tgaattcaga tatttccaga gaatgaaaaa      60
aaaatcttca gtagaaggta atgtggcgaa aacagaact gagtat                    106

<210> SEQ ID NO 58
<211> LENGTH: 84
<212> TYPE: DNA
<213> ORGANISM: Artificial Sequence
<220> FEATURE:
<223> OTHER INFORMATION: Mutant DHFR-e2 (mtDHFR)

<400> SEQUENCE: 58
gagtaacgct gtttctctaa cttgtaggaa tgaattcaga tatttccaga gaatgaaaaa      60
aaaatcttca gtagaaggta atgt                                            84

<210> SEQ ID NO 59
<211> LENGTH: 77
<212> TYPE: DNA
<213> ORGANISM: Artificial Sequence
<220> FEATURE:
<223> OTHER INFORMATION: Camk2d-e16

<400> SEQUENCE: 59
gagtaacgct gtttctctaa cttgtagtga gccccaaact actgtaatcc acaaccctga      60
cggaaacaag gtaatgt                                                    77

<210> SEQ ID NO 60
<211> LENGTH: 83
<212> TYPE: DNA
<213> ORGANISM: Artificial Sequence
<220> FEATURE:
<223> OTHER INFORMATION: Camk2d-e17

<400> SEQUENCE: 60
gagtaacgct gtttctctaa cttgtaggag tcaactgaga gctcaaacac caccattgag      60
```

```
gatgaagacg tgaaaggtaa tgt                                            83
```

<210> SEQ ID NO 61
<211> LENGTH: 85
<212> TYPE: DNA
<213> ORGANISM: Artificial Sequence
<220> FEATURE:
<223> OTHER INFORMATION: mutWT1-e5

<400> SEQUENCE: 61

```
gagtaacgct gtttctctaa cttgtagagt tgctgctgag agctccagct cagtgaaatg    60
gacagaaggg cagagcaagt aatgt                                          85
```

<210> SEQ ID NO 62
<211> LENGTH: 151
<212> TYPE: DNA
<213> ORGANISM: Artificial Sequence
<220> FEATURE:
<223> OTHER INFORMATION: SIRT1-e6

<400> SEQUENCE: 62

```
tgtggtgtgt tcaagaaaca gaaatacttc tttaataaag catatatatg ttgtttgttt    60
ttaggttcct ttgcaacagc atcttgcctg atttgtaaat acaaagttga ctgtgaagct   120
gtacgaggag atattttaa tcaggtaatg t                                   151
```

<210> SEQ ID NO 63
<211> LENGTH: 114
<212> TYPE: DNA
<213> ORGANISM: Artificial Sequence
<220> FEATURE:
<223> OTHER INFORMATION: ENEEE synthetic exon

<400> SEQUENCE: 63

```
gagtaacgct gtttctctaa cttgtagaca atcctcgaac caaacaacca aacaaccaaa    60
caatcctcga accaaacaat cctcgaacca aacaatcctc gaaccaagta atgt         114
```

<210> SEQ ID NO 64
<211> LENGTH: 1639
<212> TYPE: DNA
<213> ORGANISM: Artificial Sequence
<220> FEATURE:
<223> OTHER INFORMATION: xpt-G15-double

<400> SEQUENCE: 64

```
gccaagaggt tccatctgcc aggtatcagg gtgagtctat gggacccttg atgttttctt    60
tccccttctt ttctatggtt aagttcatgt cataggaagg ggagaagtaa cagggtacac   120
atattgacca aatcagggta attttgcatt tgtaatttta aaaatgcttt tcttcttta    180 atatactttt ttgtttatct tatttctaat acttteccta atctetttet ttcagggcaa   240 taatgataca atgtatcatg ccgagtaacg ctgtttctct aacttgtagg aatgaattca   300
gatatttcca gagaatgaaa aaaaaatctt cagtagaagg taatgtgtat aatcgcgtgg   360
atatggcacg caagtttcta ccgggcaccg taaatgtccg actacacatt acgcaccatt   420
ctaaagaata acagtgataa tttctgggtt aaggcaatag caatatttct gcatataaat   480
atttctgcat ataaattgta actgatgtaa gaggtttcat attgctaata gcagctacaa   540
tccagctacc attctgcttt tattttatgg ttgggataag gctggattat tctgagtcca   600
agctaggccc ttttgctaat catgttcata cctcttatct tcctcccaca gcaaggatat   660
```

```
gggctcactg agactacatc agctattctg attacacccg aggggatga taaaccgggc    720 gcggtcggta agttgttcc atttttgaa gcgaaggttg tggatctgga taccgggaaa    780
acgctgggcg ttaatcaaag aggcgaactg tgtgtgagag gtcctatgat tatgtccggt    840
tatgtaaaca atccggaagc gaccaacgcc ttgattgaca aggatggatg gctacattct    900
ggagacatag cttactggga cgaagacgaa cacttcttca tcgttgaccg cctgaagtct    960
ctgattaagt acaaagggtg agtctatggg acccttgatg tttttctttcc ccttcttttc   1020 tatggttaag ttcatgtcat aggaagggga gaagtaacag ggtacacata ttgaccaaat   1080
cagggtaatt ttgcatttgt aatttaaaa aatgctttct tcttttaata tactttttg    1140 tttatcttat ttctaatact ttccctaatc tctttctttc agggcaataa tgatacaatg   1200
tatcatgccg agtaacgctg tttctctaac ttgtaggaat gaattcagat atttccagag   1260
aatgaaaaaa aaatcttcag tagaaggtaa tgtgtataat cgcgtggata tggcacgcaa   1320
gtttctaccg ggcaccgtaa atgtccgact acacattacg caccattcta aagaataaca   1380
gtgataattt ctgggttaag gcaatagcaa tatttctgca tataaatatt tctgcatata   1440
aattgtaact gatgtaagag gtttcatatt gctaatagca gctacaatcc agctaccatt   1500
ctgcttttat tttatggttg ggataaggct ggattattct gagtccaagc taggcccttt   1560
tgctaatcat gttcatacct cttatcttcc tcccacagct atcaggtggc tcccgctgaa   1620
ttggaatcca tcttgctcc                                                1639

<210> SEQ ID NO 65
<211> LENGTH: 53
<212> TYPE: DNA
<213> ORGANISM: Artificial Sequence
<220> FEATURE:
<223> OTHER INFORMATION: synthetic construct

<400> SEQUENCE: 65
taatcgcgtg gatatggcac gcaagtttct accgggcacc gtaaatgtcc gac           53

<210> SEQ ID NO 66
<211> LENGTH: 34
<212> TYPE: DNA
<213> ORGANISM: Artificial Sequence
<220> FEATURE:
<223> OTHER INFORMATION: synthetic construct

<400> SEQUENCE: 66
agagggtgag ttggcgaaag ccaactcacc ctct                                34

<210> SEQ ID NO 67
<211> LENGTH: 34
<212> TYPE: DNA
<213> ORGANISM: Artificial Sequence
<220> FEATURE:
<223> OTHER INFORMATION: synthetic construct

<400> SEQUENCE: 67
agagggtgag ttggcgaaaa acagcataaa gtat                                34

<210> SEQ ID NO 68
<211> LENGTH: 34
<212> TYPE: DNA
<213> ORGANISM: Artificial Sequence
<220> FEATURE:
<223> OTHER INFORMATION: synthetic construct

<400> SEQUENCE: 68
```
agaaggtaat gtggcgaaag ccacattacc ttct        34

<210> SEQ ID NO 69
<211> LENGTH: 34
<212> TYPE: DNA
<213> ORGANISM: Artificial Sequence
<220> FEATURE:
<223> OTHER INFORMATION: synthetic construct

<400> SEQUENCE: 69
agaaggtaat gtggcgaaaa acagaactga gtat        34

<210> SEQ ID NO 70
<211> LENGTH: 32
<212> TYPE: DNA
<213> ORGANISM: Artificial Sequence
<220> FEATURE:
<223> OTHER INFORMATION: synthetic construct

<400> SEQUENCE: 70
ttcagtagaa ggtaatgtgg caccattggc ga        32

<210> SEQ ID NO 71
<211> LENGTH: 28
<212> TYPE: DNA
<213> ORGANISM: Artificial Sequence
<220> FEATURE:
<223> OTHER INFORMATION: synthetic construct

<400> SEQUENCE: 71
gcgccaatgg tgccacatta cgcaccat        28

<210> SEQ ID NO 72
<211> LENGTH: 21
<212> TYPE: DNA
<213> ORGANISM: Artificial Sequence
<220> FEATURE:
<223> OTHER INFORMATION: synthetic construct

<400> SEQUENCE: 72
ttcagtagaa ggtaatgtgg a        21

<210> SEQ ID NO 73
<211> LENGTH: 17
<212> TYPE: DNA
<213> ORGANISM: Artificial Sequence
<220> FEATURE:
<223> OTHER INFORMATION: synthetic construct

<400> SEQUENCE: 73
gccacattac gcaccat        17

<210> SEQ ID NO 74
<211> LENGTH: 20
<212> TYPE: DNA
<213> ORGANISM: Artificial Sequence
<220> FEATURE:
<223> OTHER INFORMATION: synthetic construct

<400> SEQUENCE: 74
ttcagtagaa ggtaatgtga        20

<210> SEQ ID NO 75
<211> LENGTH: 16
<212> TYPE: DNA

<213> ORGANISM: Artificial Sequence
<220> FEATURE:
<223> OTHER INFORMATION: synthetic construct

<400> SEQUENCE: 75
gcacattacg caccat      16

<210> SEQ ID NO 76
<211> LENGTH: 19
<212> TYPE: DNA
<213> ORGANISM: Artificial Sequence
<220> FEATURE:
<223> OTHER INFORMATION: synthetic construct

<400> SEQUENCE: 76
ttcagtagaa ggtaatgta      19

<210> SEQ ID NO 77
<211> LENGTH: 15
<212> TYPE: DNA
<213> ORGANISM: Artificial Sequence
<220> FEATURE:
<223> OTHER INFORMATION: synthetic construct

<400> SEQUENCE: 77
gacattacgc accat      15

<210> SEQ ID NO 78
<211> LENGTH: 32
<212> TYPE: DNA
<213> ORGANISM: Artificial Sequence
<220> FEATURE:
<223> OTHER INFORMATION: synthetic construct

<400> SEQUENCE: 78
gtagaaggta atgtggcacc attcactcat at      32

<210> SEQ ID NO 79
<211> LENGTH: 29
<212> TYPE: DNA
<213> ORGANISM: Artificial Sequence
<220> FEATURE:
<223> OTHER INFORMATION: synthetic construct

<400> SEQUENCE: 79
ctatgggtga atggtgccac attacgcac      29

<210> SEQ ID NO 80
<211> LENGTH: 20
<212> TYPE: DNA
<213> ORGANISM: Artificial Sequence
<220> FEATURE:
<223> OTHER INFORMATION: synthetic construct

<400> SEQUENCE: 80
gtagaaggta atgtggatat      20

<210> SEQ ID NO 81
<211> LENGTH: 17
<212> TYPE: DNA
<213> ORGANISM: Artificial Sequence
<220> FEATURE:
<223> OTHER INFORMATION: synthetic construct

<400> SEQUENCE: 81
ctatccacat tacgcac      17

```
<210> SEQ ID NO 82
<211> LENGTH: 19
<212> TYPE: DNA
<213> ORGANISM: Artificial Sequence
<220> FEATURE:
<223> OTHER INFORMATION: synthetic construct

<400> SEQUENCE: 82
gtagaaggta atgtgatat                                                  19

<210> SEQ ID NO 83
<211> LENGTH: 16
<212> TYPE: DNA
<213> ORGANISM: Artificial Sequence
<220> FEATURE:
<223> OTHER INFORMATION: synthetic construct

<400> SEQUENCE: 83
ctatcacatt acgcac                                                     16

<210> SEQ ID NO 84
<211> LENGTH: 18
<212> TYPE: DNA
<213> ORGANISM: Artificial Sequence
<220> FEATURE:
<223> OTHER INFORMATION: synthetic construct

<400> SEQUENCE: 84
gtagaaggta atgtgtat                                                   18

<210> SEQ ID NO 85
<211> LENGTH: 15
<212> TYPE: DNA
<213> ORGANISM: Artificial Sequence
<220> FEATURE:
<223> OTHER INFORMATION: synthetic construct

<400> SEQUENCE: 85
ctacacatta cgcac                                                      15

<210> SEQ ID NO 86
<211> LENGTH: 17
<212> TYPE: DNA
<213> ORGANISM: Artificial Sequence
<220> FEATURE:
<223> OTHER INFORMATION: synthetic construct

<400> SEQUENCE: 86
gtagaaggta atgttat                                                    17

<210> SEQ ID NO 87
<211> LENGTH: 14
<212> TYPE: DNA
<213> ORGANISM: Artificial Sequence
<220> FEATURE:
<223> OTHER INFORMATION: synthetic construct

<400> SEQUENCE: 87
ctaacattac gcac                                                       14

<210> SEQ ID NO 88
<211> LENGTH: 16
<212> TYPE: DNA
<213> ORGANISM: Artificial Sequence
<220> FEATURE:
```

<223> OTHER INFORMATION: synthetic construct

<400> SEQUENCE: 88
gtagaaggta atgtat                                                        16

<210> SEQ ID NO 89
<211> LENGTH: 13
<212> TYPE: DNA
<213> ORGANISM: Artificial Sequence
<220> FEATURE:
<223> OTHER INFORMATION: synthetic construct

<400> SEQUENCE: 89
ctacattacg cac                                                           13

<210> SEQ ID NO 90
<211> LENGTH: 15
<212> TYPE: DNA
<213> ORGANISM: Artificial Sequence
<220> FEATURE:
<223> OTHER INFORMATION: synthetic construct

<400> SEQUENCE: 90
gtagaaggta atgtt                                                         15

<210> SEQ ID NO 91
<211> LENGTH: 12
<212> TYPE: DNA
<213> ORGANISM: Artificial Sequence
<220> FEATURE:
<223> OTHER INFORMATION: synthetic construct

<400> SEQUENCE: 91
cacattacgc ac                                                            12

<210> SEQ ID NO 92
<211> LENGTH: 15
<212> TYPE: DNA
<213> ORGANISM: Artificial Sequence
<220> FEATURE:
<223> OTHER INFORMATION: synthetic construct

<400> SEQUENCE: 92
gaaggtaatg tgtat                                                         15

<210> SEQ ID NO 93
<211> LENGTH: 18
<212> TYPE: DNA
<213> ORGANISM: Artificial Sequence
<220> FEATURE:
<223> OTHER INFORMATION: synthetic construct

<400> SEQUENCE: 93
ctacacatta cgcaccat                                                      18

<210> SEQ ID NO 94
<211> LENGTH: 14
<212> TYPE: DNA
<213> ORGANISM: Artificial Sequence
<220> FEATURE:
<223> OTHER INFORMATION: synthetic construct

<400> SEQUENCE: 94
gaaggtaatg tgat                                                          14

```
<210> SEQ ID NO 95
<211> LENGTH: 17
<212> TYPE: DNA
<213> ORGANISM: Artificial Sequence
<220> FEATURE:
<223> OTHER INFORMATION: synthetic construct

<400> SEQUENCE: 95
ctcacattac gcaccat                                                    17

<210> SEQ ID NO 96
<211> LENGTH: 13
<212> TYPE: DNA
<213> ORGANISM: Artificial Sequence
<220> FEATURE:
<223> OTHER INFORMATION: synthetic construct

<400> SEQUENCE: 96
gaaggtaatg tat                                                        13

<210> SEQ ID NO 97
<211> LENGTH: 16
<212> TYPE: DNA
<213> ORGANISM: Artificial Sequence
<220> FEATURE:
<223> OTHER INFORMATION: synthetic construct

<400> SEQUENCE: 97
ctacattacg caccat                                                     16

<210> SEQ ID NO 98
<211> LENGTH: 15
<212> TYPE: DNA
<213> ORGANISM: Artificial Sequence
<220> FEATURE:
<223> OTHER INFORMATION: synthetic construct

<400> SEQUENCE: 98
gaaggtaatg tgtat                                                      15

<210> SEQ ID NO 99
<211> LENGTH: 18
<212> TYPE: DNA
<213> ORGANISM: Artificial Sequence
<220> FEATURE:
<223> OTHER INFORMATION: synthetic construct

<400> SEQUENCE: 99
ctacacatta cgcaccat                                                   18

<210> SEQ ID NO 100
<211> LENGTH: 17
<212> TYPE: DNA
<213> ORGANISM: Artificial Sequence
<220> FEATURE:
<223> OTHER INFORMATION: synthetic construct

<400> SEQUENCE: 100
gaaggtaatg tgggtat                                                    17

<210> SEQ ID NO 101
<211> LENGTH: 20
<212> TYPE: DNA
<213> ORGANISM: Artificial Sequence
<220> FEATURE:
<223> OTHER INFORMATION: synthetic construct
```

```
<400> SEQUENCE: 101
ctacccacat tacgcaccat                                          20

<210> SEQ ID NO 102
<211> LENGTH: 16
<212> TYPE: DNA
<213> ORGANISM: Artificial Sequence
<220> FEATURE:
<223> OTHER INFORMATION: synthetic construct

<400> SEQUENCE: 102
gaaggtaatg tggtat                                              16

<210> SEQ ID NO 103
<211> LENGTH: 19
<212> TYPE: DNA
<213> ORGANISM: Artificial Sequence
<220> FEATURE:
<223> OTHER INFORMATION: synthetic construct

<400> SEQUENCE: 103
ctaccacatt acgcaccat                                           19

<210> SEQ ID NO 104
<211> LENGTH: 15
<212> TYPE: DNA
<213> ORGANISM: Artificial Sequence
<220> FEATURE:
<223> OTHER INFORMATION: synthetic construct

<400> SEQUENCE: 104
gaaggtaatg tgtat                                               15

<210> SEQ ID NO 105
<211> LENGTH: 18
<212> TYPE: DNA
<213> ORGANISM: Artificial Sequence
<220> FEATURE:
<223> OTHER INFORMATION: synthetic construct

<400> SEQUENCE: 105
ctacacatta cgcaccat                                            18

<210> SEQ ID NO 106
<211> LENGTH: 17
<212> TYPE: DNA
<213> ORGANISM: Artificial Sequence
<220> FEATURE:
<223> OTHER INFORMATION: synthetic construct

<400> SEQUENCE: 106
gaaggtaatg tggatat                                             17

<210> SEQ ID NO 107
<211> LENGTH: 20
<212> TYPE: DNA
<213> ORGANISM: Artificial Sequence
<220> FEATURE:
<223> OTHER INFORMATION: synthetic construct

<400> SEQUENCE: 107
ttatccacat tacgcaccat                                          20

<210> SEQ ID NO 108
<211> LENGTH: 16
```

```
<212> TYPE: DNA
<213> ORGANISM: Artificial Sequence
<220> FEATURE:
<223> OTHER INFORMATION: synthetic construct

<400> SEQUENCE: 108
gaaggtaatg tggtat                                                    16

<210> SEQ ID NO 109
<211> LENGTH: 19
<212> TYPE: DNA
<213> ORGANISM: Artificial Sequence
<220> FEATURE:
<223> OTHER INFORMATION: synthetic construct

<400> SEQUENCE: 109
ttaccacatt acgcaccat                                                 19

<210> SEQ ID NO 110
<211> LENGTH: 20
<212> TYPE: DNA
<213> ORGANISM: Artificial Sequence
<220> FEATURE:
<223> OTHER INFORMATION: synthetic construct

<400> SEQUENCE: 110
tcttatcttc ctcccacagc                                                20

<210> SEQ ID NO 111
<211> LENGTH: 20
<212> TYPE: DNA
<213> ORGANISM: Artificial Sequence
<220> FEATURE:
<223> OTHER INFORMATION: synthetic construct

<400> SEQUENCE: 111
tcttatcttc ctcccacagc                                                20

<210> SEQ ID NO 112
<211> LENGTH: 20
<212> TYPE: DNA
<213> ORGANISM: Artificial Sequence
<220> FEATURE:
<223> OTHER INFORMATION: synthetic construct

<400> SEQUENCE: 112
tcttatcttc ctcccacagc                                                20

<210> SEQ ID NO 113
<211> LENGTH: 20
<212> TYPE: DNA
<213> ORGANISM: Artificial Sequence
<220> FEATURE:
<223> OTHER INFORMATION: synthetic construct

<400> SEQUENCE: 113
tcttatcttc ctcccacagc                                                20

<210> SEQ ID NO 114
<211> LENGTH: 21
<212> TYPE: DNA
<213> ORGANISM: Artificial Sequence
<220> FEATURE:
<223> OTHER INFORMATION: synthetic construct

<400> SEQUENCE: 114
```

```
ctttacttct atgactgtag c                                              21

<210> SEQ ID NO 115
<211> LENGTH: 21
<212> TYPE: DNA
<213> ORGANISM: Artificial Sequence
<220> FEATURE:
<223> OTHER INFORMATION: synthetic construct

<400> SEQUENCE: 115
gtgactgtgt gtatgcacag c                                              21

<210> SEQ ID NO 116
<211> LENGTH: 21
<212> TYPE: DNA
<213> ORGANISM: Artificial Sequence
<220> FEATURE:
<223> OTHER INFORMATION: synthetic construct

<400> SEQUENCE: 116
attgtgatcg cagccaatag c                                              21

<210> SEQ ID NO 117
<211> LENGTH: 50
<212> TYPE: DNA
<213> ORGANISM: Artificial Sequence
<220> FEATURE:
<223> OTHER INFORMATION: synthetic construct

<400> SEQUENCE: 117
gaatgaattc agatatttcc agagaatgac cacaacctct tcagtagaag               50

<210> SEQ ID NO 118
<211> LENGTH: 50
<212> TYPE: DNA
<213> ORGANISM: Artificial Sequence
<220> FEATURE:
<223> OTHER INFORMATION: synthetic construct

<400> SEQUENCE: 118
gaatgaattc agatatttcc agagaatgaa aaaaaaatct tcagtagaag               50

<210> SEQ ID NO 119
<211> LENGTH: 50
<212> TYPE: DNA
<213> ORGANISM: Artificial Sequence
<220> FEATURE:
<223> OTHER INFORMATION: synthetic construct

<400> SEQUENCE: 119
gaatggcccc tgatatttcc agagaatgac cacaacctct tcagtagaag               50

<210> SEQ ID NO 120
<211> LENGTH: 50
<212> TYPE: DNA
<213> ORGANISM: Artificial Sequence
<220> FEATURE:
<223> OTHER INFORMATION: synthetic construct

<400> SEQUENCE: 120
gaatgtaggg agatatttcc agagaatgac cacaacctct tcagtagaag               50
```